US009791435B2

(12) United States Patent
Sitbon et al.

(10) Patent No.: US 9,791,435 B2
(45) Date of Patent: Oct. 17, 2017

(54) RECEPTOR BINDING LIGANDS, THEIR USE IN THE DETECTION OF CELLS WITH BIOLOGICAL INTEREST

(75) Inventors: Marc Sitbon, Montpellier (FR); Jean-Luc Battini, Montpellier (FR); Naomi Taylor, Montpellier (FR); Cedric Mongellaz, Montpellier (FR)

(73) Assignees: CENTRE NATIONAL DE LA RECHERCHE SCIENTIFIQUE, Paris (FR); UNIVERSITE MONTPELLIER 2, Montpellier (FR)

( * ) Notice: Subject to any disclaimer, the term of this patent is extended or adjusted under 35 U.S.C. 154(b) by 286 days.

(21) Appl. No.: 13/143,657

(22) PCT Filed: Jan. 8, 2010

(86) PCT No.: PCT/EP2010/050139
§ 371 (c)(1),
(2), (4) Date: Sep. 7, 2011

(87) PCT Pub. No.: WO2010/079208
PCT Pub. Date: Jul. 5, 2010

(65) Prior Publication Data
US 2013/0203080 A1 Aug. 8, 2013

Related U.S. Application Data

(60) Provisional application No. 61/143,530, filed on Jan. 9, 2009.

(51) Int. Cl.
*G01N 33/53* (2006.01)
*G01N 33/537* (2006.01)

(52) U.S. Cl.
CPC ............ *G01N 33/53* (2013.01); *G01N 33/537* (2013.01); *G01N 2333/705* (2013.01); *G01N 2400/00* (2013.01)

(58) Field of Classification Search
CPC ................ A61K 38/00; C07K 14/7158; C07K 2319/00; C07K 16/2866
USPC .......................................................... 435/5
See application file for complete search history.

(56) References Cited

U.S. PATENT DOCUMENTS

| 5,897,991 | A | 4/1999 | Burstein et al. |
|---|---|---|---|
| 7,507,526 | B2 | 3/2009 | Miller et al. |
| 9,157,912 | B2 * | 10/2015 | Tirouvanziam ...... G01N 33/564 |
| 2004/0176314 | A1 | 9/2004 | Beseme et al. |

FOREIGN PATENT DOCUMENTS

| EP | 0384566 A2 | 8/1990 |
|---|---|---|
| WO | 88/05783 A1 | 8/1988 |
| WO | 92/13946 A1 | 8/1992 |
| WO | 96/21727 A1 | 7/1996 |
| WO | 96/41193 A1 | 12/1996 |
| WO | 97/15668 A2 | 5/1997 |
| WO | 98/03197 A1 | 1/1998 |
| WO | 99/45920 A2 | 9/1999 |
| WO | 99/59559 A1 | 11/1999 |
| WO | 00/46403 A2 | 8/2000 |
| WO | 01/31021 A1 | 5/2001 |
| WO | 02095400 A2 | 11/2002 |
| WO | WO02095400 | * 11/2002 |
| WO | 03/092582 A2 | 11/2003 |
| WO | WO2004042001 | * 5/2004 |
| WO | 2004/096841 A1 | 11/2004 |
| WO | WO 2004/096841 | * 11/2004 |
| WO | 2005/095442 A1 | 10/2005 |
| WO | WO2008008881 | * 1/2008 |

OTHER PUBLICATIONS

Kinet et al., Isolated receptor binding domains of HTLV-1 and HTLV-2 envelopes bind Glut-1 on activated CD4+ and CD8+ T cells, 2007, Retrovirology, 4:31, PDF pp. 1-9.*
Jones et al., Human T-Cell Leukemia Virus Type 1 (HTLV-1) and HTLV-2 Use Different Receptor Complexes to Enter T Cells, 2006, Journal of Virology, 80(17):8291-8302.*
Kinet et al., "Isolated receptor binding domains of HTLV-1 and HTLV-2 envelopes bind Glut-1 on activated CD4+ and CD8+ T cells", 2007, 4(31):pdf pp. 1-9.*
Manel et al., "The ubiquitous glucose transporter GLUT-1 is a receptor for HTLV", 2003, Cell, 115:449-459.*
Kinet Sandrina et al: "Isolated receptor binding domains of HTLV-I and HTLV-2 envelopes bind Glut-1 on activated CD4+ and CD8+ T cells", Retrovirology, Biomed Central Ltd., vol. 4, No. 1, May 15, 2007 (May 15, 2007), p. 31, XP021025311.
Lavanya Madakasira et al: "Cell surface expression of the bovine leukemia virus-binding receptor on B and T lymphocytes is induced by receptor engagement", Journal of Immunology, vol. 181, No. 2, Jul. 2008 (Jul. 2008), pp. 891-898, XP002577523.
International Search Report, dated Apr. 28, 2010, in PCT/EP2010/050139.
Cavazzana-Calvo et al., "Gene therapy of human severe combined immunodeficiency (SCID)-X1 disease", Science, 2000, vol. 288, pp. 669-672.

(Continued)

*Primary Examiner* — Shanon A Foley
(74) *Attorney, Agent, or Firm* — Young & Thompson

(57) ABSTRACT

A method for the identification and quantification of the expression of membrane receptors present on the surface of target cells using at least two soluble receptor binding ligands derived from the soluble part of the glycoprotein of an enveloped virus that interacts with a cellular cognate receptor, the receptor binding ligand containing a part or the totality of one of the receptor binding domains (RBD) of the glycoprotein, and the soluble receptor binding ligand being liable to interact with the at least one membrane receptor of a target cell, for the identification and quantification of the expression of membrane receptors present on the surface of target cells, the identification and quantification taking place at a given time or during a given time interval, and allowing the determination of a physiological state of the target cell.

24 Claims, 24 Drawing Sheets

(56) References Cited

OTHER PUBLICATIONS

Gaspar HB et al., "Gene therapy of X-linked severe combined immunodeficiency by use of a pseudotyped gammaretroviral vector", Lancet, 2004, vol. 364, pp. 2181-2187.

Goubau et al., "A primate T-lymphotropic virus, PTLV-L, different from human T-lymphotropic viruses types I and II, in a wild-caught baboon (*Papio hamadryas*)", Proc. Natl. Acad. Sci. U S A., 1994, vol. 91, pp. 2848-2852.

Jones et al., "Human T-cell leukemia virus type 1 (HTLV-1) and HTLV-2 use different receptor complexes to enter T cells", Journal of Virology, 2006, vol. 80, No. 17, pp. 8291-8302.

Manel et al., "HTLV envelopes and their receptor GLUT1, the ubiquitous glucose transporter: a new vision on HTLV infection?", 2004, Frontiers in Biosciences, vol. 9, pp. 3218-3241.

Uchiyama et al., "Functional regulation of Na+-dependent neutral amino acid transporter ASCT2 by S-nitrosothiols and nitric oxide in Caco-2 cells", 2005, FEBS Letters, 2005, vol. 579, pp. 2499-2506.

Ojeda et al., "Noncompetitive blocking of human GLUT1 hexose transporter by methylxanthines reveals an exofacial regulatory binding site", Am. J. Physiol. Cell Physiol., 2012, vol. 303, pp. C530-C539.

Koralnik et al., "Phylogenetic associations of human and simian T-cell leukemia/lymphotropic virus type I strains: evidence for interspecies transmission", Journal of Virology, 1994, vol. 68, No. 4, pp. 2693-2707.

Mahieux et al., "HTLV-3/STLV-3 and HTLV-4 viruses: discovery, epidemiology, serology and molecular aspects", Viruses, 2011, vol. 3, pp. 1074-1090.

Buck et al., "Biological characterisation of breast cancer by means of PET", European Journal of Nuclear Medicine Molecular Imaging, 2004, vol. 31, Supplement 1, pp. S80-S87.

Harris et al., "Polarized distribution of glucose transporter isoforms in Caco-2 cells", Proc. Natl. Acad. Sci. USA, Cell Biology, 1992, vol. 89, pp. 7556-7560.

Mendez et al., "Expression of glucose transporter-1 in cervical cancer and its precursors", Gynecologic Oncology, 2002, vol. 86, pp. 138-143.

Lairmore et al., "Characterization of a B-cell immunodominant epitope of human T-lymphotropic virus type 1 (HTLV-I) envelope gp46", Cancer Letters, 1992, vol. 66, pp. 11-20.

Tallet et al., "Sequence variations in the amino- and carboxy-terminal parts of the surface envelope glycoprotein of HTLV type 1 induce specific neutralizing antibodies", AIDS Research and Hum Retroviruses, 2001, vol. 17, No. 4, pp. 337-348.

Mueckler et al., "Identification of an amino acid residue that lies between the exofacial vestibule and exofacial substrate-binding site of the Glut1 sugar permeation pathway" The Journal of Biological Chemistry, vol. 272, No. 48, pp. 30141-30146.

Manel et al., "GLUT-1 is the receptor of retrovirus HTLV", Medecine Sciences, 2004, vol. 20, No. 3, pp. 277-279.

Manel et al., "The ubiquitous glucose transporter GLUT-1 is a receptor for HTLV", Cell, 2003, vol. 115, pp. 449-459.

Sakashita et al., Glut1 expression in T1 and T2 stage colorectal carcinomas: its relationship to clinicopathological features, European Journal of Cancer, vol. 37, pp. 204-209.

Wood et al., "Glucose transporters (GLUT and SGLT): expanded families of sugar transport proteins", British Journal of Nutrition, vol. 89, pp. 3-9.

Brown, G. K., Glucose transporters: structure, function and consequences of deficiency, J. Inherited Metabol. Dis., 2000, vol. 23, pp. 237-246.

Vannucci et al., "Glucose transporter proteins in brain: delivery of glucose to neurons and glia", Glia, 1997, vol. 21, pp. 2-21.

Palker et al., Purification of envelope glycoproteins of human T cell lymphotropic virus type I (HTLV-I) by affinity chromatography, Journal of Virology Methods, 1987, vol. 18, pp. 243-256.

Young et al., "Regulation of myocardial glucose uptake and transport during ischemia and energetic stress", Am. J. Cardiol., 1999, vol. 83, pp. 25H-30H.

Reske et al., "Overexpression of glucose transporter 1 and increased FDG uptake in pancreatic carcinoma", The Journal of Nuclear Medicine, 1997, vol. 38, No. 9, pp. 1344-1348.

Bos et al., "Biologic correlates of 18fluorodeoxyglucose uptake in human breast cancer measured by positron emission tomography", Journal of Clinical Oncology, vol. 20, No. 2, pp. 379-387.

Moadel et al., Positherapy: targeted nuclear therapy of breast cancer with 18F-2-deoxy-2-fluoro-D-glucose, Cancer Research, 2005, vol. 65, No. 3, pp. 698-702.

Pankratz et al., "Insulin receptor substrate-2 regulates aerobic glycolysis in mouse mammary tumor cells via glucose transporter 1", The Journal of Biological Chemistry, 2009, vol. 284, No. 4, pp. 2031-2037.

Amann et al., "GLUT1 expression is increased in hepatocellular carcinoma and promotes tumorigenesis", The American Journal of Pathology, 2009, vol. 174, No. 4, pp. 1544-1552.

Fan et al., "Glucose transporter protein 1-targeted RNA interference inhibits growth and invasion of the osteosarcoma cell line MG63 in vitro", Cancer Biotherapy and Radiopharmaceuticals, 2010, vol. 25, No. 5, pp. 521-527.

Kawamura et al., "Expression of glucose transporter-1 in human gastric carcinoma: association with tumor aggressiveness, metastasis, and patient survival", Cancer, 2001, vol. 92, pp. 634-641.

May et al., "Photolabeling of the human erythrocyte glucose carrier with androgenic steroids", 1988, Biochimica et Biophysica Acta, 1988, vol. 943, pp. 199-210.

Hellwig et al., "Differentiation of erythrocyte-(GLUT1), liver-(GLUT2), and adipocyte-type (GLUT4) glucose transporters by binding of the inhibitory ligands cytochalasin B, forskolin, dipyridamole, and isobutylmethylxanthine", Molecular Pharmacology, 1991, vol. 40, pp. 383-389.

Krauss et al., "Selective inhibition by ethanol of the type 1 facilitative glucose transporter (GLUT1)", Molecular Pharmacology, 1994, vol. 45, pp. 1281-1286.

Vera et al., "Genistein is a natural inhibitor of hexose and dehydroascorbic acid transport through the glucose transporter, GLUT1", The Journal of Biological Chemistry, 1996, vol. 271, No. 15, pp. 8719-8724.

Lachaal et al., "Cadmium increases GLUT1 substrate binding affinity in vitro while reducing its cytochalasin B binding affinity", Biochemistry, 1996, vol. 35, pp. 14958-14962.

El-Barbary et al., "Barbiturate inhibition of GLUT-1 mediated hexose transport in human erythrocytes exhibits substrate dependence for equilibrium exchange but not unidirectional sugar flux", Biochemistry, 1996, vol. 35, pp. 15222-15227.

Rumsey et al., "Glucose transporter isoforms GLUT1 and GLUT3 transport dehydroascorbic acid", The Journal of Biological Chemistry, 1997, vol. 272, No. 30, pp. 18982-18989.

Pinkofsky et al., "The inhibition of GLUT1 glucose transport and cytochalasin B binding activity by tricyclic antidepressants", Life Sciences, vol. 66, No. 3, pp. 271-278.

Afzal et al., "Interactions of ATP, oestradiol, genistein and the anti-oestrogens, faslodex (ICI 182780) and tamoxifen, with the human erythrocyte glucose transporter, GLUT1", Biochem. J., 2002, vol. 365, pp. 707-719.

Russo et al., "Peroxisome proliferator-activated receptor gamma thiazolidinedione agonists increase glucose metabolism in astrocytes", The Journal of Biological Chemistry, 2003, vol. 278, No. 8, pp. 5828-5836.

Frauwirth et al., "The CD28 signaling pathway regulates glucose metabolism", Immunity, 2002, vol. 16, pp. 769-777.

Gamelli et al., "Augmentations of glucose uptake and glucose transporter-1 in macrophages following thermal injury and sepsis in mice", The Journal of Leukocyte Biology, 1996, vol. 59, pp. 639-647.

Battellino et al., "Tissue glucose transport and glucose transporters in suckling rats with endotoxic shock", Shock, 1996, vol. 6, No. 4, pp. 259-262.

Fukuzumi et al., "Endotoxin-induced enhancement of glucose influx into murine peritoneal macrophages via GLUT1", Infection and Immunity, 1996, vol. 64, No. 1, pp. 108-112.

(56) References Cited

OTHER PUBLICATIONS

Chakrabarti et al., "Changes in glucose transport and transporter isoforms during the activation of human peripheral blood lymphocytes by phytohemagglutinin", Journal of Immunology, 1994, vol. 152, pp. 2660-2668.

Zeller et al., "Altered glucose transporter mRNA abundance in a rat model of endotoxic shock", Biochem Biophys Res Commun., 1991, vol. 176, pp. 535-540.

Mochizuki et al., "FDG uptake and glucose transporter subtype expressions in experimental tumor and inflammation models", J. Nucl. Med., 2001, vol. 42, pp. 1551-1555.

Tokita et al., "Serial changes in 14C-deoxyglucose and 201TI uptake in autoimmune myocarditis in rats", J. Nucl. Med., 2001, vol. 42, pp. 285-291.

Peters, "The energy request of inflammation", Endocrinology, 2006, vol. 147, pp. 4550-4552.

Adhikani et al., "Increase in GLUT1 in smooth muscle alters vascular contractility and increases inflammation in response to vascular injury", Arterioscler Thromb Vasc Biol., 2011, vol. 31, pp. 86-94.

Suarez et al., "Identification of hypervariable and conserved regions in the surface envelope gene in the bovine lentivirus", Virology, 1995, vol. 212, pp. 728-733.

Palayoor et al., "Ibuprofen-mediated reduction of hypoxia-inducible factors HIF-1alpha and HIF-2alpha in prostate cancer cells", Clinical Cancer Research, 2003, vol. 9, pp. 3150-3157.

Perzova et al., "Lack of BLV and PTLV DNA sequences in the majority of patients with large granular lymphocyte leukaemia", British Journal of Haematology, 2000, vol. 109, pp. 64-70.

Ramirez et al., "Genetic characterization and phylogeny of human T-cell lymphotropic virus type I from Chile" Virus Research, 2002, vol. 84, pp. 135-149.

Dube et al., "Degenerate and specific PCR assays for the detection of bovine leukaemia virus and primate T cell leukaemia/lymphoma virus pol DNA and RNA: phylogenetic comparisons of amplified sequences from cattle and primates from around the world", Journal of General Virology, 1997, vol. 78, pp. 1389-1398.

Gray et al., "Envelope gene sequence of HTLV-1 isolate MT-2 and its comparison with other HTLV-1 isolates", Virology, 1990, vol. 177, pp. 391-395.

Ting et al., "Simian sarcoma-associated virus fails to infect Chinese hamster cells despite the presence of functional gibbon ape leukemia virus receptors", Journal of Virology, 1998, vol. 72, No. 12, pp. 9453-9458.

\* cited by examiner

SEQUENCE LISTING

```
<160> NUMBER OF SEQ ID NOS: 31

<210> SEQ ID NO 1
<211> LENGTH: 328
<212> TYPE: PRT
<213> ORGANISM: Artificial Sequence
<220> FEATURE:
<223> OTHER INFORMATION: Derived from Env Amphotropic Murine Leukaemia
      Virus 4070A
<220> FEATURE:
<221> NAME/KEY: PEPTIDE
<222> LOCATION: (1)..(328)

<400> SEQUENCE: 1

Met Ala Arg Ser Thr Leu Ser Lys Pro Pro Gln Asp Lys Ile Asn Pro
1               5                   10                  15

Trp Lys Pro Leu Ile Val Met Gly Val Leu Leu Gly Val Gly Met Ala
            20                  25                  30

Glu Ser Pro His Gln Val Phe Asn Val Thr Trp Arg Val Thr Asn Leu
        35                  40                  45

Met Thr Gly Arg Thr Ala Asn Ala Thr Ser Leu Leu Gly Thr Val Gln
    50                  55                  60

Asp Ala Phe Pro Lys Leu Tyr Phe Asp Leu Cys Asp Leu Val Gly Glu
65                  70                  75                  80

Glu Trp Asp Pro Ser Asp Gln Glu Pro Tyr Val Gly Tyr Gly Cys Lys
                85                  90                  95

Tyr Pro Ala Gly Arg Gln Arg Thr Arg Thr Phe Asp Phe Tyr Val Cys
            100                 105                 110

Pro Gly His Thr Val Lys Ser Gly Cys Gly Gly Pro Gly Glu Gly Tyr
        115                 120                 125

Cys Gly Lys Trp Gly Cys Glu Thr Thr Gly Gln Ala Tyr Trp Lys Pro
    130                 135                 140

Thr Ser Ser Trp Asp Leu Ile Ser Leu Lys Arg Gly Asn Thr Pro Trp
145                 150                 155                 160

Asp Thr Gly Cys Ser Lys Val Ala Cys Gly Pro Cys Tyr Asp Leu Ser
                165                 170                 175

Lys Val Ser Asn Ser Phe Gln Gly Ala Thr Arg Gly Gly Arg Cys Asn
            180                 185                 190

Pro Leu Val Leu Glu Phe Thr Asp Ala Gly Lys Lys Ala Asn Trp Asp
        195                 200                 205

Gly Pro Lys Ser Trp Gly Leu Arg Leu Tyr Arg Thr Gly Thr Asp Pro
    210                 215                 220

Ile Thr Met Phe Ser Leu Thr Arg Gln Val Leu Asn Val Gly Pro Arg
225                 230                 235                 240

Val Pro Ile Gly Pro Asn Pro Val Leu Pro Asp Gln Arg Leu Pro Ser
                245                 250                 255

Ser Pro Ile Glu Ile Val Pro Ala Pro Gln Pro Pro Ser Pro Leu Asn
            260                 265                 270

Thr Ser Tyr Pro Pro Ser Thr Thr Ser Thr Pro Ser Thr Ser Pro Thr
        275                 280                 285
```

Ser Pro Ser Val Pro Gln Pro Pro Gly Thr Gly Asp Arg Leu Leu
    290                 295                 300

Ala Leu Val Lys Gly Ala Tyr Gln Ala Leu Asn Leu Thr Asn Pro Asp
305                 310                 315                 320

Lys Thr Gln Glu Cys Trp Leu Cys
                325

<210> SEQ ID NO 2
<211> LENGTH: 357
<212> TYPE: PRT
<213> ORGANISM: Artificial Sequence
<220> FEATURE:
<223> OTHER INFORMATION: Derived from Env Gibbon Ape Leukaemia Virus
<220> FEATURE:
<221> NAME/KEY: PEPTIDE
<222> LOCATION: (1)..(357)

<400> SEQUENCE: 2

Met Val Leu Leu Pro Gly Ser Met Leu Leu Thr Ser Asn Leu His His
1               5                   10                  15

Leu Arg His Gln Met Ser Pro Gly Ser Trp Lys Arg Leu Ile Ile Leu
            20                  25                  30

Leu Ser Cys Val Phe Gly Gly Gly Thr Ser Leu Gln Asn Lys Asn
        35                  40                  45

Pro His Gln Pro Met Thr Leu Thr Trp Gln Val Leu Ser Gln Thr Gly
    50                  55                  60

Asp Val Val Trp Asp Thr Lys Ala Val Gln Pro Pro Trp Thr Trp Trp
65                  70                  75                  80

Pro Thr Leu Lys Pro Asp Val Cys Ala Leu Ala Ala Ser Leu Glu Ser
                85                  90                  95

Trp Asp Ile Pro Gly Thr Asp Val Ser Ser Lys Arg Val Arg Pro
                100                 105                 110

Pro Asp Ser Asp Tyr Thr Ala Ala Tyr Lys Gln Ile Thr Trp Gly Ala
            115                 120                 125

Ile Gly Cys Ser Tyr Pro Arg Ala Arg Thr Arg Met Ala Ser Ser Thr
    130                 135                 140

Phe Tyr Val Cys Pro Arg Asp Gly Arg Thr Leu Ser Glu Ala Arg Arg
145                 150                 155                 160

Cys Gly Gly Leu Glu Ser Leu Tyr Cys Lys Glu Trp Asp Cys Glu Thr
                165                 170                 175

Thr Gly Thr Gly Tyr Trp Leu Ser Lys Ser Ser Lys Asp Leu Ile Thr
            180                 185                 190

Val Lys Trp Asp Gln Asn Ser Glu Trp Thr Gln Lys Phe Gln Gln Cys
    195                 200                 205

His Gln Thr Gly Trp Cys Asn Pro Leu Lys Ile Asp Phe Thr Asp Lys
210                 215                 220

Gly Lys Leu Ser Lys Asp Trp Ile Thr Gly Lys Thr Trp Gly Leu Arg
225                 230                 235                 240

Phe Tyr Val Ser Gly His Pro Gly Val Gln Phe Thr Ile Arg Leu Lys
                245                 250                 255

Ile Thr Asn Met Pro Ala Val Ala Val Gly Pro Asp Leu Val Leu Val
            260                 265                 270

Glu Gln Gly Pro Pro Arg Thr Ser Leu Ala Leu Pro Pro Pro Leu Pro
    275                 280                 285

Pro Arg Glu Ala Pro Pro Pro Ser Leu Pro Asp Ser Asn Ser Thr Ala
290                 295                 300

```
Leu Ala Thr Ser Ala Gln Thr Pro Thr Val Arg Lys Thr Ile Val Thr
305                 310                 315                 320

Leu Asn Thr Pro Pro Thr Gly Asp Arg Leu Phe Asp Leu Val
            325                 330                 335

Gln Gly Ala Phe Leu Thr Leu Asn Ala Thr Asn Pro Gly Ala Thr Glu
            340                 345                 350

Ser Cys Trp Leu Cys
        355
```

<210> SEQ ID NO 3
<211> LENGTH: 239
<212> TYPE: PRT
<213> ORGANISM: Artificial Sequence
<220> FEATURE:
<223> OTHER INFORMATION: Derived from Env Feline endogenous Leukaemia
      Virus RD 114
<220> FEATURE:
<221> NAME/KEY: PEPTIDE
<222> LOCATION: (1)..(239)

<400> SEQUENCE: 3

```
Met Lys Leu Pro Thr Gly Met Val Ile Leu Cys Ser Leu Ile Ile Val
1               5                   10                  15

Arg Ala Gly Phe Asp Asp Pro Arg Lys Ala Ile Ala Leu Val Gln Lys
            20                  25                  30

Gln His Gly Lys Pro Cys Glu Cys Ser Gly Gln Val Ser Glu Ala
            35                  40                  45

Pro Pro Asn Ser Ile Gln Gln Val Thr Cys Pro Gly Lys Thr Ala Tyr
50                  55                  60

Leu Met Thr Asn Gln Lys Trp Lys Cys Arg Val Thr Pro Lys Ile Ser
65                  70                  75                  80

Pro Ser Gly Gly Glu Leu Gln Asn Cys Pro Cys Asn Thr Phe Gln Asp
                85                  90                  95

Ser Met His Ser Ser Cys Tyr Thr Glu Tyr Arg Gln Cys Arg Arg Ile
            100                 105                 110

Asn Lys Thr Tyr Tyr Thr Ala Thr Leu Leu Lys Ile Arg Ser Gly Ser
            115                 120                 125

Leu Asn Glu Val Gln Ile Leu Gln Asn Pro Asn Gln Leu Leu Gln Ser
    130                 135                 140

Pro Cys Arg Gly Ser Ile Asn Gln Pro Val Cys Trp Ser Ala Thr Ala
145                 150                 155                 160

Pro Ile His Ile Ser Asp Gly Gly Gly Pro Leu Asp Thr Lys Arg Val
                165                 170                 175

Trp Thr Val Gln Lys Arg Leu Glu Gln Ile His Lys Ala Met Thr Pro
            180                 185                 190

Glu Leu Gln Tyr His Pro Leu Ala Leu Pro Lys Val Arg Asp Asp Leu
            195                 200                 205

Ser Leu Asp Ala Arg Thr Phe Asp Ile Leu Asn Thr Thr Phe Arg Leu
    210                 215                 220

Leu Gln Met Ser Asn Phe Ser Leu Ala Gln Asp Cys Trp Leu Cys
225                 230                 235
```

<210> SEQ ID NO 4
<211> LENGTH: 462
<212> TYPE: PRT
<213> ORGANISM: Artificial Sequence
<220> FEATURE:
<223> OTHER INFORMATION: Derived from Vesicular Stomatitis Virus G

```
        glycoprotein
<220> FEATURE:
<221> NAME/KEY: PEPTIDE
<222> LOCATION: (1)..(462)

<400> SEQUENCE: 4

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Asp Leu Asn Trp
        35                  40                  45

His Asn Asp Leu Ile Gly Thr Ala Ile Gln Val Lys Met Pro Lys Ser
50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr Gln
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
            115                 120                 125

Ser Cys Gly Tyr Ala Thr Val Thr Asp Ala Glu Ala Val Ile Val Gln
130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
            195                 200                 205

Gly Glu Leu Ser Ser Leu Gly Lys Glu Gly Thr Gly Phe Arg Ser Asn
210                 215                 220

Tyr Phe Ala Tyr Glu Thr Gly Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

Glu Arg Glu Leu Trp Asp Asp Trp Ala Pro Tyr Glu Asp Val Glu Ile
        370                 375                 380
```

```
Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
            405                 410                 415

Lys Ala Gln Val Phe Glu His Pro His Ile Gln Asp Ala Ala Ser Gln
            420                 425                 430

Leu Pro Asp Asp Glu Ser Leu Phe Phe Gly Asp Thr Gly Leu Ser Lys
            435                 440                 445

Asn Pro Ile Glu Leu Val Glu Gly Trp Phe Ser Ser Trp Lys
            450                 455                 460

<210> SEQ ID NO 5
<211> LENGTH: 339
<212> TYPE: PRT
<213> ORGANISM: Artificial Sequence
<220> FEATURE:
<223> OTHER INFORMATION: Derived from Env ecotropic Moloney -Murine
      Leukaemia Virus
<220> FEATURE:
<221> NAME/KEY: PEPTIDE
<222> LOCATION: (1)..(339)

<400> SEQUENCE: 5

Met Ala Arg Ser Thr Leu Ser Lys Pro Leu Lys Asn Lys Val Asn Pro
1               5                   10                  15

Arg Gly Pro Leu Ile Pro Leu Ile Leu Leu Met Leu Arg Gly Val Ser
            20                  25                  30

Thr Ala Ser Pro Gly Ser Ser Pro His Gln Val Tyr Asn Ile Thr Trp
            35                  40                  45

Glu Val Thr Asn Gly Asp Arg Glu Thr Val Trp Ala Thr Ser Gly Asn
50                  55                  60

His Pro Leu Trp Thr Trp Trp Pro Asp Leu Thr Pro Asp Leu Cys Met
65                  70                  75                  80

Leu Ala His His Gly Pro Ser Tyr Trp Gly Leu Glu Tyr Gln Ser Pro
            85                  90                  95

Phe Ser Ser Pro Pro Gly Pro Pro Cys Cys Ser Gly Gly Ser Ser Pro
            100                 105                 110

Gly Cys Ser Arg Asp Cys Glu Glu Pro Leu Thr Ser Leu Thr Pro Arg
            115                 120                 125

Cys Asn Thr Ala Trp Asn Arg Leu Lys Leu Asp Gln Thr Thr His Lys
            130                 135                 140

Ser Asn Glu Gly Phe Tyr Val Cys Pro Gly Pro His Arg Pro Arg Glu
145                 150                 155                 160

Ser Lys Ser Cys Gly Gly Pro Asp Ser Phe Tyr Cys Ala Tyr Trp Gly
            165                 170                 175

Cys Glu Thr Thr Gly Arg Ala Tyr Trp Lys Pro Ser Ser Ser Trp Asp
            180                 185                 190

Phe Ile Thr Val Asn Asn Asn Leu Thr Ser Asp Gln Ala Val Gln Val
            195                 200                 205

Cys Lys Asp Asn Lys Trp Cys Asn Pro Leu Val Ile Arg Phe Thr Asp
            210                 215                 220

Ala Gly Arg Arg Val Thr Ser Trp Thr Thr Gly His Tyr Trp Gly Leu
225                 230                 235                 240

Arg Leu Tyr Val Ser Gly Gln Asp Pro Gly Leu Thr Phe Gly Ile Arg
            245                 250                 255

Leu Arg Tyr Gln Asn Leu Gly Pro Arg Val Pro Ile Gly Pro Asn Pro
            260                 265                 270
```

```
Val Leu Ala Asp Gln Gln Pro Leu Ser Lys Pro Lys Pro Val Lys Ser
            275                 280                 285

Pro Ser Val Thr Lys Pro Pro Ser Gly Thr Pro Leu Ser Pro Thr Gln
        290                 295                 300

Leu Pro Pro Ala Gly Thr Glu Asn Arg Leu Leu Asn Leu Val Asp Gly
305                 310                 315                 320

Ala Tyr Gln Ala Leu Asn Leu Thr Ser Pro Asp Lys Thr Gln Glu Cys
                325                 330                 335

Trp Leu Cys

<210> SEQ ID NO 6
<211> LENGTH: 349
<212> TYPE: PRT
<213> ORGANISM: Artificial Sequence
<220> FEATURE:
<223> OTHER INFORMATION: Derived from Env ecotropic Friend Murine
      Leukaemia Virus
<220> FEATURE:
<221> NAME/KEY: PEPTIDE
<222> LOCATION: (1)..(349)

<400> SEQUENCE: 6

Met Ala Cys Ser Thr Leu Pro Lys Ser Pro Lys Asp Lys Ile Asp Pro
1               5                   10                  15

Arg Asp Leu Leu Ile Pro Leu Ile Leu Phe Leu Ser Leu Lys Gly Ala
            20                  25                  30

Arg Ser Ala Ala Pro Gly Ser Ser Pro His Gln Val Tyr Asn Ile Thr
        35                  40                  45

Trp Glu Val Thr Asn Gly Asp Arg Glu Thr Val Trp Ala Ile Ser Gly
    50                  55                  60

Asn His Pro Leu Trp Thr Trp Trp Pro Val Leu Thr Pro Asp Leu Cys
65                  70                  75                  80

Met Leu Ala Leu Ser Gly Pro Pro His Trp Gly Leu Glu Tyr Gln Ala
                85                  90                  95

Pro Tyr Ser Ser Pro Pro Gly Pro Pro Cys Cys Ser Gly Ser Ser Gly
            100                 105                 110

Ser Ser Ala Gly Cys Ser Arg Asp Cys Asp Glu Pro Leu Thr Ser Leu
        115                 120                 125

Thr Pro Arg Cys Asn Thr Ala Trp Asn Arg Leu Lys Leu Asp Gln Val
130                 135                 140

Thr His Lys Ser Ser Glu Gly Phe Tyr Val Cys Pro Gly Ser His Arg
145                 150                 155                 160

Pro Arg Glu Ala Lys Ser Cys Gly Gly Pro Asp Ser Phe Tyr Cys Ala
                165                 170                 175

Ser Trp Gly Cys Glu Thr Thr Gly Arg Val Tyr Trp Lys Pro Ser Ser
            180                 185                 190

Ser Trp Asp Tyr Ile Thr Val Asp Asn Asn Leu Thr Thr Ser Gln Ala
        195                 200                 205

Val Gln Val Cys Lys Asp Asn Lys Trp Cys Asn Pro Leu Ala Ile Gln
210                 215                 220

Phe Thr Asn Ala Gly Lys Gln Val Thr Ser Trp Thr Thr Gly His Tyr
225                 230                 235                 240

Trp Gly Leu Arg Leu Tyr Val Ser Gly Arg Asp Pro Gly Leu Thr Phe
                245                 250                 255

Gly Ile Arg Leu Arg Tyr Gln Asn Leu Gly Pro Arg Val Pro Ile Gly
            260                 265                 270
```

```
Pro Asn Pro Val Leu Ala Asp Gln Leu Ser Leu Pro Arg Pro Asn Pro
            275                 280                 285

Leu Pro Lys Pro Ala Lys Ser Pro Pro Ala Ser Asn Ser Thr Pro Thr
290                 295                 300

Leu Ile Ser Pro Ser Pro Thr Pro Thr Gln Pro Pro Ala Gly Thr
305                 310                 315                 320

Gly Asp Arg Leu Leu Asn Leu Val Gln Gly Ala Tyr Gln Ala Leu Asn
            325                 330                 335

Leu Thr Asn Pro Asp Lys Thr Gln Glu Cys Trp Leu Cys
            340                 345

<210> SEQ ID NO 7
<211> LENGTH: 340
<212> TYPE: PRT
<213> ORGANISM: Artificial Sequence
<220> FEATURE:
<223> OTHER INFORMATION: Derived from Env ecotropic AKV Murine Leukaemia
      Virus
<220> FEATURE:
<221> NAME/KEY: PEPTIDE
<222> LOCATION: (1)..(340)

<400> SEQUENCE: 7

Met Glu Ser Thr Thr Leu Ser Lys Pro Phe Lys Asn Gln Val Asn Pro
1               5                   10                  15

Trp Gly Pro Leu Ile Val Leu Ile Leu Gly Val Asn Pro Val
            20                  25                  30

Thr Leu Gly Asn Ser Pro His Gln Val Phe Asn Leu Thr Trp Glu Val
            35                  40                  45

Thr Asn Gly Asp Arg Glu Thr Val Trp Ala Ile Thr Gly Asn His Pro
50                  55                  60

Leu Trp Thr Trp Trp Pro Asp Leu Thr Pro Asp Leu Cys Met Leu Ala
65                  70                  75                  80

Leu His Gly Pro Ser Tyr Trp Gly Leu Glu Tyr Arg Ala Pro Phe Ser
                85                  90                  95

Pro Pro Pro Gly Pro Pro Cys Cys Ser Gly Ser Ser Asp Ser Thr Pro
            100                 105                 110

Gly Cys Ser Arg Asp Cys Glu Glu Pro Leu Thr Ser Tyr Thr Pro Arg
            115                 120                 125

Cys Asn Thr Ala Trp Asn Arg Leu Lys Leu Ser Lys Val Thr His Ala
            130                 135                 140

His Asn Gly Gly Phe Tyr Val Cys Pro Gly Pro His Arg Pro Arg Trp
145                 150                 155                 160

Ala Arg Ser Cys Gly Gly Pro Glu Ser Phe Tyr Cys Ala Ser Trp Gly
            165                 170                 175

Cys Glu Thr Thr Gly Arg Ala Ser Trp Lys Pro Ser Ser Ser Trp Asp
            180                 185                 190

Tyr Ile Thr Val Ser Asn Asn Leu Thr Ser Asp Gln Ala Thr Pro Val
            195                 200                 205

Cys Lys Gly Asn Glu Trp Cys Asn Ser Leu Thr Ile Arg Phe Thr Ser
            210                 215                 220

Phe Gly Lys Gln Ala Thr Ser Trp Val Thr Gly His Trp Trp Gly Leu
225                 230                 235                 240

Arg Leu Tyr Val Ser Gly His Asp Pro Gly Leu Ile Phe Gly Ile Arg
            245                 250                 255

Leu Lys Ile Thr Asp Ser Gly Pro Arg Val Pro Ile Gly Pro Asn Pro
```

```
                260                 265                 270
Val Leu Ser Asp Arg Arg Pro Pro Ser Arg Pro Arg Pro Thr Arg Ser
            275                 280                 285

Pro Pro Pro Ser Asn Ser Thr Pro Thr Glu Thr Pro Leu Thr Leu Pro
            290                 295                 300

Glu Pro Pro Pro Ala Gly Val Glu Asn Arg Leu Leu Asn Leu Val Lys
305                 310                 315                 320

Gly Ala Tyr Gln Ala Leu Asn Leu Thr Ser Pro Asp Lys Thr Gln Glu
                325                 330                 335

Cys Trp Leu Cys
            340

<210> SEQ ID NO 8
<211> LENGTH: 289
<212> TYPE: PRT
<213> ORGANISM: Artificial Sequence
<220> FEATURE:
<223> OTHER INFORMATION: Derived from Env M813 Murine Leukaemia Virus
<220> FEATURE:
<221> NAME/KEY: PEPTIDE
<222> LOCATION: (1)..(289)

<400> SEQUENCE: 8

Met Ala Asp Ser Ser Leu Ser Glu Pro Ser Lys Asp Lys Thr His Ser
1               5                   10                  15

Arg Ala Pro Thr Ile Ala Leu Gly Ile Leu Val Leu Gly Arg Val
            20                  25                  30

Ala Gln Gly Gly Ser Pro His Gln Pro Val Thr Leu Thr Trp Gln Val
            35                  40                  45

Leu Asp Glu Glu Leu Tyr Val Lys Trp Glu Thr Ser Gly Lys His Pro
        50                  55                  60

Glu Trp Thr Trp Trp Pro Asp Leu Thr Pro Asp Leu Ser Gly Phe Ser
65                  70                  75                  80

Cys Asp Tyr Ser Gln Leu Asn Val Pro Asp Phe Tyr Val Cys Pro Gly
                85                  90                  95

His Gly Lys Ser Tyr Ser Arg Arg Val Cys Gly Gly Ala Glu Ser Ala
            100                 105                 110

Phe Cys Ala Lys Trp Gly Cys Glu Thr Thr Gly Asp Ala Tyr Trp Asn
        115                 120                 125

Pro Asn Arg Pro Asp Leu Ile Ile Val Lys Lys Gly Gln Asn Arg Thr
130                 135                 140

Ala Cys Lys Gly Asn Lys Cys Gln Gly Lys Tyr Cys Asn Pro Leu Lys
145                 150                 155                 160

Ile Thr Phe Thr Asp Gln Gly Lys Asn Ser Arg Glu Trp Lys Arg Gly
                165                 170                 175

Leu Arg Trp Gly Cys Trp Val His Leu Leu Ser Gln His Phe Ile Phe
            180                 185                 190

Tyr Ile Arg Leu Gln Val Thr Arg Ser Pro Val Leu Ala Ile Gly Pro
        195                 200                 205

Asn Pro Val Val Ala Asp Gln Lys Pro Pro Ser Arg Pro Ala Pro Val
    210                 215                 220

Ile Pro Pro Val Pro Pro Gln Val Asn Pro Thr Gly Ala Thr Asp Asn
225                 230                 235                 240

Thr Thr Gly Thr Thr Pro Thr Thr Val Leu Ser Thr Lys Gln Pro Gln
                245                 250                 255

Arg Pro Gly Thr Gly Asp Arg Leu Leu Asp Leu Val Gln Gly Ala Tyr
```

```
                      260                 265                 270
Leu Ala Leu Asn Phe Thr Asn Pro Glu Lys Thr Gln Glu Cys Trp Leu
            275                 280                 285

Cys

<210> SEQ ID NO 9
<211> LENGTH: 319
<212> TYPE: PRT
<213> ORGANISM: Artificial Sequence
<220> FEATURE:
<223> OTHER INFORMATION: Derived from Env 10A1 Murine Leukaemia Virus
<220> FEATURE:
<221> NAME/KEY: PEPTIDE
<222> LOCATION: (1)..(319)

<400> SEQUENCE: 9

Met Glu Gly Pro Ala Phe Ser Lys Pro Leu Lys Asp Lys Ile Asn Pro
1               5                   10                  15

Trp Lys Ser Leu Met Val Met Gly Val Tyr Leu Arg Val Gly Met Ala
            20                  25                  30

Glu Ser Pro His Gln Val Phe Asn Val Thr Trp Arg Val Thr Asn Leu
        35                  40                  45

Met Thr Gly Arg Thr Ala Asn Ala Thr Ser Leu Leu Gly Thr Val Gln
    50                  55                  60

Asp Ala Phe Pro Arg Leu Tyr Phe Asp Leu Cys Asp Leu Val Gly Glu
65                  70                  75                  80

Glu Trp Asp Pro Ser Asp Gln Glu Pro Tyr Val Gly Tyr Gly Cys Lys
                85                  90                  95

Tyr Pro Gly Gly Arg Lys Arg Thr Arg Thr Phe Asp Phe Tyr Val Cys
            100                 105                 110

Pro Gly His Thr Val Lys Ser Gly Cys Gly Gly Pro Arg Glu Gly Tyr
        115                 120                 125

Cys Gly Glu Trp Gly Cys Glu Thr Thr Gly Gln Ala Tyr Trp Lys Pro
    130                 135                 140

Thr Ser Ser Trp Asp Leu Ile Ser Leu Lys Arg Gly Asn Thr Pro Trp
145                 150                 155                 160

Asp Thr Gly Cys Ser Lys Met Ala Cys Gly Pro Cys Tyr Asp Leu Ser
                165                 170                 175

Lys Val Ser Asn Ser Phe Gln Gly Ala Thr Arg Gly Gly Arg Cys Asn
            180                 185                 190

Pro Leu Val Leu Glu Phe Thr Asp Ala Gly Lys Lys Ala Asn Trp Asp
        195                 200                 205

Gly Pro Lys Ser Trp Gly Leu Arg Leu Tyr Arg Thr Gly Thr Asp Pro
    210                 215                 220

Ile Thr Met Phe Ser Leu Thr Arg Gln Val Leu Asn Ile Gly Pro Arg
225                 230                 235                 240

Ile Pro Ile Gly Pro Asn Pro Val Ile Thr Gly Gln Leu Pro Pro Ser
                245                 250                 255

Arg Pro Val Gln Ile Arg Leu Pro Arg Pro Gln Pro Pro Thr
            260                 265                 270

Gly Ala Ala Ser Ile Val Pro Glu Thr Ala Pro Ser Gln Pro
        275                 280                 285

Gly Thr Gly Asp Arg Leu Leu Asn Leu Val Glu Gly Ala Tyr Gln Ala
    290                 295                 300

Leu Asn Leu Thr Asn Pro Asp Lys Thr Gln Glu Cys Trp Leu Cys
305                 310                 315
```

<210> SEQ ID NO 10
<211> LENGTH: 316
<212> TYPE: PRT
<213> ORGANISM: Artificial Sequence
<220> FEATURE:
<223> OTHER INFORMATION: Derived from Env Xenotropic Murine Leukaemia Virus (NZB)
<220> FEATURE:
<221> NAME/KEY: PEPTIDE
<222> LOCATION: (1)..(316)

<400> SEQUENCE: 10

```
Met Leu Val Met Glu Gly Ser Ala Phe Ser Lys Pro Leu Lys Asp Lys
1               5                   10                  15

Ile Asn Pro Trp Gly Pro Leu Ile Val Met Gly Ile Leu Val Arg Ala
            20                  25                  30

Gly Ala Ser Val Gln Arg Asp Ser Pro His Gln Ile Phe Asn Val Thr
        35                  40                  45

Trp Arg Val Thr Asn Leu Met Thr Gly Gln Thr Ala Asn Ala Thr Ser
    50                  55                  60

Leu Leu Gly Thr Met Thr Asp Thr Phe Pro Lys Leu Tyr Phe Asp Leu
65                  70                  75                  80

Cys Asp Leu Val Gly Asp Tyr Trp Asp Pro Glu Pro Asp Ile Gly
                85                  90                  95

Asp Gly Cys Arg Thr Pro Gly Gly Arg Arg Thr Arg Leu Tyr Asp
            100                 105                 110

Phe Tyr Val Cys Pro Gly His Thr Val Pro Ile Gly Cys Gly Gly Pro
        115                 120                 125

Gly Glu Gly Tyr Cys Gly Lys Trp Gly Cys Glu Thr Thr Gly Gln Ala
    130                 135                 140

Tyr Trp Lys Pro Ser Ser Ser Trp Asp Leu Ile Ser Leu Lys Arg Gly
145                 150                 155                 160

Asn Thr Pro Lys Asp Gln Gly Pro Cys Tyr Asp Ser Ser Val Ser Ser
                165                 170                 175

Gly Val Gln Gly Ala Thr Pro Gly Gly Arg Cys Asn Pro Leu Val Leu
            180                 185                 190

Glu Phe Thr Asp Ala Gly Arg Lys Ala Ser Trp Asp Ala Pro Lys Val
        195                 200                 205

Trp Gly Leu Arg Leu Tyr Arg Ser Thr Gly Ala Asp Pro Val Thr Arg
    210                 215                 220

Phe Ser Leu Thr Arg Gln Val Leu Asn Val Gly Pro Arg Val Pro Ile
225                 230                 235                 240

Gly Pro Asn Pro Val Ile Thr Asp Gln Leu Pro Pro Ser Gln Pro Val
                245                 250                 255

Gln Ile Met Leu Pro Arg Pro Pro His Pro Pro Ser Gly Thr Val
            260                 265                 270

Ser Met Val Pro Gly Ala Pro Pro Ser Gln Pro Gly Thr Gly
        275                 280                 285

Asp Arg Leu Leu Asn Leu Val Glu Gly Ala Tyr Gln Ala Leu Asn Leu
    290                 295                 300

Thr Ser Pro Asp Lys Thr Gln Glu Cys Trp Leu Cys
305                 310                 315
```

<210> SEQ ID NO 11
<211> LENGTH: 313
<212> TYPE: PRT

-continued

```
<213> ORGANISM: Artificial Sequence
<220> FEATURE:
<223> OTHER INFORMATION: Derived from Env Xenotropic Murine Leukaemia
      Virus (Bxv1)
<220> FEATURE:
<221> NAME/KEY: PEPTIDE
<222> LOCATION: (1)..(313)

<400> SEQUENCE: 11

Met Glu Gly Pro Ala Phe Ser Lys Pro Leu Lys Asp Lys Ile Asn Pro
1               5                   10                  15

Trp Gly Pro Leu Ile Val Ile Gly Ile Leu Val Arg Ala Gly Ala Ser
            20                  25                  30

Val Gln Arg Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Thr Phe Pro Lys Leu Tyr Phe Asp Leu Cys Asp Leu
65                  70                  75                  80

Val Gly Asp His Trp Asp Asp Pro Glu Pro Asp Ile Gly Asp Gly Cys
                85                  90                  95

Arg Ser Pro Gly Gly Arg Lys Arg Ser Arg Leu Tyr Asp Phe Tyr Val
            100                 105                 110

Cys Pro Gly His Thr Val Pro Ile Gly Cys Gly Gly Pro Gly Glu Gly
        115                 120                 125

Tyr Cys Gly Lys Trp Gly Cys Glu Thr Thr Gly Gln Ala Tyr Trp Lys
130                 135                 140

Pro Ser Ser Ser Trp Asp Leu Ile Ser Leu Lys Arg Gly Asn Thr Pro
145                 150                 155                 160

Lys Asp Gln Gly Pro Cys Tyr Asp Ser Ser Val Ser Ser Gly Val Gln
                165                 170                 175

Gly Ala Thr Pro Gly Gly Arg Cys Asn Pro Leu Val Leu Glu Phe Thr
            180                 185                 190

Asp Ala Gly Lys Lys Ala Ser Trp Asp Ala Pro Lys Val Trp Gly Leu
        195                 200                 205

Arg Leu Tyr Arg Ser Thr Gly Ala Asp Pro Val Thr Arg Phe Ser Leu
    210                 215                 220

Thr Arg Gln Val Leu Asn Val Gly Pro Arg Val Pro Ile Gly Pro Asn
225                 230                 235                 240

Pro Val Ile Thr Glu Gln Leu Pro Ser Gln Pro Val Gln Ile Met
                245                 250                 255

Leu Pro Arg Pro Pro His Pro Pro Pro Ser Gly Ala Ala Ser Met Val
            260                 265                 270

Pro Gly Ala Pro Pro Pro Ser Gln Gln Pro Gly Thr Gly Asp Arg Leu
        275                 280                 285

Leu Asn Leu Val Lys Gly Ala Tyr Gln Ala Leu Asn Leu Thr Ser Pro
    290                 295                 300

Asp Arg Thr Gln Glu Cys Trp Leu Cys
305                 310

<210> SEQ ID NO 12
<211> LENGTH: 314
<212> TYPE: PRT
<213> ORGANISM: Artificial Sequence
<220> FEATURE:
<223> OTHER INFORMATION: Derived from Env XMRV (new Human Murine
      Leukaemia Virus-like)
<220> FEATURE:
```

<221> NAME/KEY: PEPTIDE
<222> LOCATION: (1)..(314)

<400> SEQUENCE: 12

Met Glu Ser Pro Ala Phe Ser Lys Pro Leu Lys Asp Lys Ile Asn Pro
1               5                   10                  15

Trp Gly Pro Leu Ile Ile Met Gly Ile Leu Val Arg Ala Gly Ala Ser
            20                  25                  30

Val Gln Arg Asp Ser Pro His Gln Val Phe Asn Val Thr Trp Lys Ile
        35                  40                  45

Thr Asn Leu Met Thr Gly Gln Thr Ala Asn Ala Thr Ser Leu Leu Gly
    50                  55                  60

Thr Met Thr Asp Thr Phe Pro Lys Leu Tyr Phe Asp Leu Cys Asp Leu
65                  70                  75                  80

Val Gly Asp Asn Trp Asp Asp Pro Glu Pro Asp Ile Gly Asp Gly Cys
                85                  90                  95

Arg Ser Pro Gly Gly Arg Lys Arg Thr Arg Leu Tyr Asp Phe Tyr Val
            100                 105                 110

Cys Pro Gly His Thr Val Leu Thr Gly Cys Gly Gly Pro Arg Glu Gly
        115                 120                 125

Tyr Cys Gly Lys Trp Gly Cys Glu Thr Thr Gly Gln Ala Tyr Trp Lys
    130                 135                 140

Pro Ser Ser Ser Trp Asp Leu Ile Ser Leu Lys Arg Gly Asn Thr Pro
145                 150                 155                 160

Lys Gly Gln Gly Pro Cys Phe Asp Ser Ser Val Gly Ser Gly Ser Ile
                165                 170                 175

Gln Gly Ala Thr Pro Gly Gly Arg Cys Asn Pro Leu Val Leu Glu Phe
            180                 185                 190

Thr Asp Ala Gly Lys Arg Ala Ser Trp Asp Ala Pro Lys Thr Trp Gly
        195                 200                 205

Leu Arg Leu Tyr Arg Ser Thr Gly Ala Asp Pro Val Thr Leu Phe Ser
    210                 215                 220

Leu Thr Arg Gln Val Leu Asn Val Gly Pro Arg Val Pro Ile Gly Pro
225                 230                 235                 240

Asn Pro Val Ile Thr Glu Gln Leu Pro Pro Ser Gln Pro Val Gln Ile
                245                 250                 255

Met Leu Pro Arg Pro Pro Arg Pro Pro Pro Ser Gly Ala Ala Ser Met
            260                 265                 270

Val Pro Gly Ala Pro Pro Ser Gln Gln Pro Gly Thr Gly Asp Arg
        275                 280                 285

Leu Leu Asn Leu Val Glu Gly Ala Tyr Gln Ala Leu Asn Leu Thr Ser
    290                 295                 300

Pro Asp Lys Thr Gln Glu Cys Trp Leu Cys
305                 310

<210> SEQ ID NO 13
<211> LENGTH: 310
<212> TYPE: PRT
<213> ORGANISM: Artificial Sequence
<220> FEATURE:
<223> OTHER INFORMATION: Derived from Env MCF polytropic Murine
      Leukaemia Virus (MX27)
<220> FEATURE:
<221> NAME/KEY: PEPTIDE
<222> LOCATION: (1)..(310)

<400> SEQUENCE: 13

Met Glu Gly Pro Ala Phe Ser Lys Pro Leu Lys Asp Lys Ile Asn Pro
1               5                   10                  15

Trp Gly Pro Leu Ile Val Leu Gly Ile Leu Ile Arg Ala Gly Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
            100                 105                 110

Thr Val Pro Thr Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Arg Asn Gln Gly
145                 150                 155                 160

Pro Cys Tyr Asp Ser Ser Ala Val Ser Ser Asp Ile Lys Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205

Arg Ser Thr Gly Thr Asp Pro Val Thr Arg Phe Ser Leu Thr Arg Gln
    210                 215                 220

Val Leu Asn Ile Gly Pro Arg Val Pro Ile Gly Pro Asn Pro Val Ile
225                 230                 235                 240

Thr Asp Gln Leu Pro Pro Ser Arg Pro Val Gln Ile Met Leu Pro Arg
                245                 250                 255

Pro Pro Gln Pro Pro Pro Gly Ala Ala Ser Ile Val Pro Glu Thr
            260                 265                 270

Ala Pro Pro Ser Gln Gln Pro Gly Thr Gly Asp Arg Leu Leu Asn Leu
        275                 280                 285

Val Asp Gly Ala Tyr Gln Ala Leu Asn Leu Thr Ser Pro Asp Lys Thr
    290                 295                 300

Gln Glu Cys Trp Leu Cys
305             310

<210> SEQ ID NO 14
<211> LENGTH: 301
<212> TYPE: PRT
<213> ORGANISM: Artificial Sequence
<220> FEATURE:
<223> OTHER INFORMATION: Derived from Env MCF polytropic Murine
      Leukaemia Virus (MX33)
<220> FEATURE:
<221> NAME/KEY: PEPTIDE
<222> LOCATION: (1)..(301)

<400> SEQUENCE: 14

Met Glu Gly Pro Ala Phe Ser Lys Pro Leu Lys Asp Lys Ile Asn Pro
1               5                   10                  15

Trp Ala Pro Leu Ile Val Leu Gly Ile Leu Ile Arg Ala Gly Val Ser
            20                  25                  30

Val Pro His Asp Ser Pro His Gln Val Phe Asn Val Thr Trp Arg Val
            35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
                100                 105                 110

Thr Val Pro Thr Gly Cys Gly Gly Pro Arg Glu Gly Tyr Cys Gly Lys
            115                 120                 125

Trp Gly Cys Glu Thr Thr Gly Gln Ala Tyr Trp Lys Pro Ser Ser Ser
130                 135                 140

Trp Asp Leu Ile Ser Leu Lys Arg Gly Asn Thr Pro Arg Asn Gln Gly
145                 150                 155                 160

Pro Cys Tyr Asp Ser Ser Ala Val Ser Ser Gly Ile Gln Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
            195                 200                 205

Arg Ser Thr Gly Thr Asp Pro Val Thr Arg Phe Ser Leu Thr Arg Gln
            210                 215                 220

Val Leu Asn Ile Gly Pro Arg Ile Pro Ile Gly Pro Asn Pro Val Ile
225                 230                 235                 240

Thr Asp Gln Leu Pro Pro Ser Arg Pro Val Gln Ile Met Leu Pro Arg
                245                 250                 255

Pro Pro Gln Pro Ser Pro Thr Gly Ala Ala Ser Ile Gln Pro Gly Thr
            260                 265                 270

Gly Asp Arg Leu Leu Asn Leu Val Asp Gly Ala Tyr Gln Ala Leu Asn
            275                 280                 285

Leu Thr Ser Pro Asp Lys Thr Gln Glu Cys Trp Leu Cys
    290                 295                 300

<210> SEQ ID NO 15
<211> LENGTH: 310
<212> TYPE: PRT
<213> ORGANISM: Artificial Sequence
<220> FEATURE:
<223> OTHER INFORMATION: Derived from Env MCF1233 polytropic Murine
      Leukaemia Virus
<220> FEATURE:
<221> NAME/KEY: PEPTIDE
<222> LOCATION: (1)..(310)

<400> SEQUENCE: 15

Met Glu Gly Pro Ala Phe Ser Lys Pro Leu Lys Asp Lys Ile Asn Pro
1               5                   10                  15

Trp Gly Pro Leu Ile Ile Leu Gly Ile Leu Ile Arg Ala Gly Val Ser
            20                  25                  30

Val Gln His Asp Ser Pro His Gln Val Phe Asn Val Thr Trp Arg Val
            35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu

```
                65                  70                  75                  80
Ile Gly Asp Asp Trp Asp Glu Thr Gly Leu Gly Cys Arg Thr Pro Gly
                    85                  90                  95

Gly Arg Lys Arg Ala Arg Thr Phe Asp Phe Tyr Val Cys Pro Gly His
                100                 105                 110

Thr Val Pro Thr Gly Cys Gly Pro Arg Glu Gly Tyr Cys Gly Lys
            115                 120                 125

Trp Gly Cys Glu Thr Thr Gly Gln Ala Tyr Trp Lys Pro Ser Ser Ser
        130                 135                 140

Trp Asp Leu Ile Ser Leu Lys Arg Gly Asn Thr Pro Gln Asn Gln Gly
145                 150                 155                 160

Pro Cys Tyr Asp Ser Ser Ala Val Ser Ser Asp Ile Lys Gly Ala Thr
                165                 170                 175

Pro Gly Gly Arg Cys Asn Pro Leu Val Leu Glu Phe Thr Asp Ala Gly
                180                 185                 190

Lys Lys Ala Ser Trp Asp Gly Pro Lys Val Trp Gly Leu Arg Leu Tyr
            195                 200                 205

Arg Pro Thr Gly Thr Asp Pro Val Thr Arg Phe Ser Leu Thr Arg Arg
    210                 215                 220

Val Leu Asn Ile Gly Pro Arg Val Pro Ile Gly Pro Asn Pro Val Ile
225                 230                 235                 240

Ala Asp Gln Leu Pro Pro Ser Arg Pro Val Gln Ile Met Leu Pro Arg
                245                 250                 255

Pro Pro Gln Pro Pro Pro Gly Ala Ser Ser Ile Val Pro Glu Thr
            260                 265                 270

Ala Pro Pro Ser Gln Gln Pro Gly Thr Gly Asp Arg Leu Leu Asn Leu
        275                 280                 285

Val Asp Gly Ala Tyr Gln Ala Leu Asn Leu Thr Ser Pro Asp Lys Thr
    290                 295                 300

Gln Glu Cys Trp Leu Cys
305                 310

<210> SEQ ID NO 16
<211> LENGTH: 348
<212> TYPE: PRT
<213> ORGANISM: Artificial Sequence
<220> FEATURE:
<223> OTHER INFORMATION: Derived from Env Mus dunni endogenous virus
<220> FEATURE:
<221> NAME/KEY: PEPTIDE
<222> LOCATION: (1)..(348)

<400> SEQUENCE: 16

Met Lys Lys Pro Thr Lys Thr Thr Gly Leu Trp Lys Pro Leu Ile Thr
1               5                   10                  15

Leu Leu Ser Phe Ala Cys Val Ala Gly Ala Pro Ser Ile Thr Leu Asp
                20                  25                  30

Leu Gly Asn His Asn Pro His Ala Pro Val Gln Gln Ser Trp Glu Val
            35                  40                  45

Leu Asn Glu Lys Gly Asp Val Val Trp Val Ala Thr Ala Val His Pro
        50                  55                  60

Pro Trp Thr Trp Trp Pro Asp Leu Thr Pro Asp Ile Cys Lys Leu Ala
65                  70                  75                  80

Ala Gly Ser Pro Asn Trp Asp Leu Pro Asp His Thr Asp Leu Asn Asn
                85                  90                  95

Pro Pro Ser Glu Gln Lys Cys Val Pro Asn Gly Val Gly Ser Thr Thr
```

-continued

```
                100                 105                 110
Gly Cys Ser Gly Gln Phe Tyr Arg Ala Asn Leu Arg Ala Ala Gln Phe
            115                 120                 125

Tyr Val Cys Pro Gly Gln Gly Lys Gly Lys Leu Gln Gln Glu Cys
130                 135                 140

Arg Gly Ala Ser Asp Tyr Phe Cys Gly Lys Trp Thr Cys Glu Thr Thr
145                 150                 155                 160

Gly Glu Ala Tyr Trp Lys Pro Ser Ala Asp Trp Asp Leu Ile Thr Val
                165                 170                 175

Lys Arg Gly Ser Gly Tyr Asp Lys Pro Asn Gln Gly Glu Arg Asn Pro
            180                 185                 190

Tyr Lys Tyr Leu Asp Ser Gly Cys Ala Leu Lys Asn Tyr Ser Pro Pro
            195                 200                 205

Gly Pro Cys Lys Gly Lys Tyr Cys Asn Pro Leu Leu Ile Lys Phe Thr
            210                 215                 220

Glu Lys Gly Lys Gln Ala Arg Leu Ser Trp Leu Lys Gly Asn Arg Trp
225                 230                 235                 240

Gly Trp Arg Val Tyr Ile Pro Ile Arg Asp Pro Gly Phe Ile Phe Thr
                245                 250                 255

Ile Arg Leu Thr Val Arg Asp Leu Ala Val Thr Ser Ile Gly Pro Asn
                260                 265                 270

Lys Val Leu Thr Glu Gln Ala Pro Pro Val Ala Pro Ala Pro Pro Arg
            275                 280                 285

Val Pro Ala Val Pro Ala Pro Pro Thr Ser Arg Pro Tyr Thr Val Gly
            290                 295                 300

Pro Ser Leu Glu Thr Thr Leu Ala Ser Pro Pro Leu Leu Asp Thr Glu
305                 310                 315                 320

Asn Arg Leu Val Ser Leu Val Gln Gly Ala Phe Leu Val Leu Asn Arg
                325                 330                 335

Thr Asn Pro Asn Met Thr Gln Ser Cys Trp Leu Cys
                340                 345

<210> SEQ ID NO 17
<211> LENGTH: 315
<212> TYPE: PRT
<213> ORGANISM: Artificial Sequence
<220> FEATURE:
<223> OTHER INFORMATION: Derived from Env Feline Leukaemia Virus A
<220> FEATURE:
<221> NAME/KEY: PEPTIDE
<222> LOCATION: (1)..(315)

<400> SEQUENCE: 17

Met Glu Ser Pro Thr His Pro Lys Pro Ser Lys Asp Lys Thr Leu Ser
1               5                   10                  15

Trp Asn Leu Ala Phe Leu Val Gly Ile Leu Phe Thr Ile Asp Ile Gly
                20                  25                  30

Met Ala Asn Pro Ser Pro His Gln Ile Tyr Asn Val Thr Trp Val Ile
            35                  40                  45

Thr Asn Val Gln Thr Asn Thr Gln Ala Asn Ala Thr Ser Met Leu Gly
        50                  55                  60

Thr Leu Thr Asp Ala Tyr Pro Thr Leu His Val Asp Leu Cys Asp Leu
65                  70                  75                  80

Val Gly Asp Thr Trp Glu Pro Ile Val Leu Asn Pro Thr Asn Val Lys
                85                  90                  95

His Gly Ala Arg Tyr Ser Ser Ser Lys Tyr Gly Cys Lys Thr Thr Asp
```

```
                     100                 105                 110
Arg Lys Lys Gln Gln Gln Thr Tyr Pro Phe Tyr Val Cys Pro Gly His
            115                 120                 125
Ala Pro Ser Leu Gly Pro Lys Gly Thr His Cys Gly Gly Ala Gln Asp
            130                 135                 140
Gly Phe Cys Ala Ala Trp Gly Cys Glu Thr Thr Gly Glu Ala Trp Trp
145                 150                 155                 160
Lys Pro Thr Ser Ser Trp Asp Tyr Ile Thr Val Lys Arg Gly Ser Ser
                165                 170                 175
Gln Asp Asn Ser Cys Glu Gly Lys Cys Asn Pro Leu Val Leu Gln Phe
            180                 185                 190
Thr Gln Lys Gly Arg Gln Ala Ser Trp Asp Gly Pro Lys Met Trp Gly
            195                 200                 205
Leu Arg Leu Tyr Arg Thr Gly Tyr Asp Pro Ile Ala Leu Phe Thr Val
            210                 215                 220
Ser Arg Gln Val Ser Thr Ile Thr Pro Pro Gln Ala Met Gly Pro Asn
225                 230                 235                 240
Leu Val Leu Pro Asp Gln Lys Pro Pro Ser Arg Gln Ser Gln Thr Gly
                245                 250                 255
Ser Lys Val Ala Thr Gln Arg Pro Gln Thr Asn Glu Ser Ala Pro Arg
                260                 265                 270
Ser Val Ala Pro Thr Thr Met Gly Pro Lys Arg Ile Gly Thr Gly Asp
                275                 280                 285
Arg Leu Ile Asn Leu Val Gln Gly Thr Tyr Leu Ala Leu Asn Ala Thr
            290                 295                 300
Asp Pro Asn Lys Thr Lys Asp Cys Trp Leu Cys
305                 310                 315

<210> SEQ ID NO 18
<211> LENGTH: 335
<212> TYPE: PRT
<213> ORGANISM: Artificial Sequence
<220> FEATURE:
<223> OTHER INFORMATION: Derived from Env Feline Leukaemia Virus B
<220> FEATURE:
<221> NAME/KEY: PEPTIDE
<222> LOCATION: (1)..(335)

<400> SEQUENCE: 18

Met Glu Ser Pro Thr His Pro Lys Pro Ser Lys Asp Lys Thr Leu Ser
1               5                   10                  15
Trp Asn Leu Val Phe Leu Val Gly Ile Leu Phe Thr Ile Asp Ile Gly
                20                  25                  30
Met Ala Asn Pro Ser Pro His Gln Val Tyr Asn Val Thr Trp Thr Ile
            35                  40                  45
Thr Asn Leu Val Thr Gly Thr Lys Ala Asn Ala Thr Ser Met Leu Gly
        50                  55                  60
Thr Leu Thr Asp Ala Phe Pro Thr Met Tyr Phe Asp Leu Cys Asp Ile
65                  70                  75                  80
Ile Gly Asn Thr Trp Asn Pro Ser Asp Gln Glu Pro Phe Pro Gly Tyr
                85                  90                  95
Gly Cys Asp Gln Pro Met Arg Arg Trp Gln Gln Arg Asn Thr Pro Phe
            100                 105                 110
Tyr Val Cys Pro Gly His Ala Asn Arg Lys Gln Cys Gly Gly Pro Gln
            115                 120                 125
Asp Gly Phe Cys Ala Val Trp Gly Cys Glu Thr Thr Gly Glu Thr Tyr
```

```
                130                 135                 140
Trp Arg Pro Thr Ser Ser Trp Asp Tyr Ile Thr Val Lys Lys Gly Val
145                 150                 155                 160

Thr Gln Gly Ile Tyr Gln Cys Ser Gly Gly Gly Trp Cys Gly Pro Cys
                165                 170                 175

Tyr Asp Lys Ala Val His Ser Ser Thr Gly Ala Ser Glu Gly Gly
                180                 185                 190

Arg Cys Asn Pro Leu Ile Leu Gln Phe Thr Gln Lys Gly Arg Gln Thr
                195                 200                 205

Ser Trp Asp Gly Pro Lys Ser Trp Gly Leu Arg Leu Tyr Arg Ser Gly
                210                 215                 220

Tyr Asp Pro Ile Ala Leu Phe Ser Val Ser Arg Gln Val Met Thr Ile
225                 230                 235                 240

Thr Pro Pro Gln Ala Met Gly Pro Asn Leu Val Leu Pro Asp Gln Lys
                245                 250                 255

Pro Pro Ser Arg Gln Ser Gln Ile Glu Ser Arg Val Thr Pro His His
                260                 265                 270

Ser Gln Gly Asn Gly Gly Thr Pro Gly Ile Thr Leu Val Asn Ala Ser
                275                 280                 285

Ile Ala Pro Leu Ser Thr Pro Val Thr Pro Ala Ser Pro Lys Arg Ile
                290                 295                 300

Gly Thr Gly Asp Arg Leu Ile Asn Leu Val Gln Gly Thr Tyr Leu Ala
305                 310                 315                 320

Leu Asn Ala Thr Asp Pro Asn Arg Thr Lys Asp Cys Trp Leu Cys
                325                 330                 335

<210> SEQ ID NO 19
<211> LENGTH: 312
<212> TYPE: PRT
<213> ORGANISM: Artificial Sequence
<220> FEATURE:
<223> OTHER INFORMATION: Derived from Env Feline Leukaemia Virus C
<220> FEATURE:
<221> NAME/KEY: PEPTIDE
<222> LOCATION: (1)..(312)

<400> SEQUENCE: 19

Met Glu Ser Pro Thr His Pro Lys Pro Ser Lys Asp Lys Thr Phe Pro
1               5                   10                  15

Trp Asn Leu Val Phe Leu Val Gly Ile Leu Phe Gln Ile Asp Met Gly
                20                  25                  30

Met Ala Asn Pro Ser Pro His Gln Val Tyr Asn Val Thr Trp Val Ile
                35                  40                  45

Thr Asn Val Gln Thr Asn Ser Arg Ala Asn Ala Thr Ser Met Leu Gly
                50                  55                  60

Thr Leu Thr Asp Ala Tyr Pro Thr Leu Tyr Val Asp Leu Cys Asp Leu
65                  70                  75                  80

Val Gly Asp Thr Trp Glu Pro Ile Ala Pro Asp Pro Arg Ser Trp Ala
                85                  90                  95

Arg Tyr Ser Ser Ser Thr His Gly Cys Lys Thr Thr Asp Arg Lys Lys
                100                 105                 110

Gln Gln Gln Thr Tyr Pro Phe Tyr Val Cys Pro Gly His Ala Pro Ser
                115                 120                 125

Met Gly Pro Lys Gly Thr Tyr Cys Gly Gly Ala Gln Asp Gly Phe Cys
                130                 135                 140

Ala Ala Trp Gly Cys Glu Thr Thr Gly Glu Ala Trp Trp Lys Pro Thr
```

-continued

```
            145                 150                 155                 160
        Ser Ser Trp Asp Tyr Ile Thr Val Lys Arg Gly Ser Asn Gln Asp Asn
                        165                 170                 175

Ser Cys Lys Gly Lys Cys Asn Pro Leu Val Leu Gln Phe Thr Gln Lys
                        180                 185                 190

Gly Arg Gln Ala Ser Trp Asp Arg Pro Lys Met Trp Gly Leu Arg Leu
                        195                 200                 205

Tyr Arg Ser Gly Tyr Asp Pro Ile Ala Leu Phe Ser Val Ser Arg Gln
                        210                 215                 220

Val Met Thr Ile Thr Pro Pro Gln Ala Met Gly Pro Asn Leu Val Leu
        225                 230                 235                 240

Pro Asp Gln Lys Pro Pro Ser Arg Gln Ser Gln Thr Lys Ser Lys Val
                        245                 250                 255

Thr Thr Gln Arg Pro Gln Ile Thr Ser Ser Thr Pro Arg Ser Val Ala
                        260                 265                 270

Ser Ala Thr Met Gly Pro Lys Arg Ile Gly Thr Gly Asp Arg Leu Ile
                        275                 280                 285

Asn Leu Val Gln Gly Thr Tyr Leu Ala Leu Asn Ala Thr Asp Pro Asn
                        290                 295                 300

Lys Thr Lys Asp Cys Trp Leu Cys
        305                 310

<210> SEQ ID NO 20
<211> LENGTH: 331
<212> TYPE: PRT
<213> ORGANISM: Artificial Sequence
<220> FEATURE:
<223> OTHER INFORMATION: Derived from Env Koala Retrovirus
<220> FEATURE:
<221> NAME/KEY: PEPTIDE
<222> LOCATION: (1)..(321)

<400> SEQUENCE: 20

Met Leu Leu Ile Ser Asn Pro Arg His Leu Gly His Pro Met Ser Pro
        1               5                   10                  15

Gly Asn Trp Lys Arg Leu Ile Ile Leu Leu Ser Cys Val Phe Gly Gly
                        20                  25                  30

Ala Glu Met Asn Gln Gln His Asn Asn Pro His Gln Pro Met Thr Leu
                        35                  40                  45

Thr Trp Gln Val Leu Ser Gln Thr Gly Ser Val Val Trp Glu Lys Lys
                50                  55                  60

Ala Val Glu Pro Pro Trp Thr Trp Pro Ser Leu Glu Pro Asp Val
        65                  70                  75                  80

Cys Ala Leu Val Ala Gly Leu Glu Ser Trp Asp Ile Pro Glu Leu Thr
                        85                  90                  95

Ala Ser Ala Ser Gln Gln Ala Arg Pro Pro Asp Ser Asn Tyr Glu His
                        100                 105                 110

Ala Tyr Asn Gln Ile Thr Trp Gly Thr Leu Gly Cys Ser Tyr Pro Arg
                        115                 120                 125

Ala Arg Thr Arg Ile Ala Arg Ser Gln Phe Tyr Val Cys Pro Arg Asp
                        130                 135                 140

Gly Arg Ser Leu Ser Glu Ala Arg Arg Cys Gly Gly Leu Glu Ser Leu
        145                 150                 155                 160

Tyr Cys Lys Glu Trp Gly Cys Glu Thr Ala Gly Thr Ala Tyr Trp Gln
                        165                 170                 175

Pro Arg Ser Ser Trp Asp Leu Ile Thr Val Gly Gln Gly His Pro Thr
```

```
            180             185             190
Gly Thr Cys Glu Arg Thr Gly Trp Cys Asn Pro Leu Lys Ile Glu Phe
            195                 200                 205
Thr Glu Pro Gly Lys Arg Phe Arg Asn Trp Leu Gln Gly Arg Thr Trp
        210                 215                 220
Gly Leu Arg Phe Tyr Val Thr Gly His Pro Gly Val Gln Leu Thr Ile
225                 230                 235                 240
Arg Leu Val Ile Thr Ser Pro Pro Val Val Gly Pro Asp Pro
                    245                 250                 255
Val Leu Ala Glu Gln Gly Pro Arg Lys Ile Pro Phe Leu Pro Arg
                260                 265                 270
Val Pro Val Pro Thr Leu Ser Pro Pro Ala Ser Pro Ile Pro Thr Val
            275                 280                 285
Gln Ala Ser Pro Pro Ala Pro Ser Thr Pro Ser Pro Thr Thr Gly Asp
            290                 295                 300
Arg Leu Phe Gly Leu Val Gln Gly Ala Phe Leu Ala Leu Asn Ala Thr
305                 310                 315                 320
Asn Pro Glu Ala Thr Glu Ser Cys Trp Leu Cys
                325                 330

<210> SEQ ID NO 21
<211> LENGTH: 329
<212> TYPE: PRT
<213> ORGANISM: Artificial Sequence
<220> FEATURE:
<223> OTHER INFORMATION: Derived from Env Porcine Endogeneous
      Retrovirus-A
<220> FEATURE:
<221> NAME/KEY: PEPTIDE
<222> LOCATION: (1)..(329)

<400> SEQUENCE: 21

Met His Pro Thr Leu Ser Arg Arg His Leu Pro Ile Arg Gly Gly Lys
1               5                   10                  15
Pro Lys Arg Leu Lys Ile Pro Leu Ser Phe Ala Ser Ile Ala Trp Phe
            20                  25                  30
Leu Thr Leu Ser Ile Thr Pro Gln Val Asn Gly Lys Arg Leu Val Asp
        35                  40                  45
Ser Pro Asn Ser His Lys Pro Leu Ser Leu Thr Trp Leu Leu Thr Asp
50                  55                  60
Ser Gly Thr Gly Ile Asn Ile Asn Ser Thr Gln Gly Glu Ala Pro Leu
65                  70                  75                  80
Gly Thr Trp Trp Pro Glu Leu Tyr Val Cys Leu Arg Ser Val Ile Pro
                85                  90                  95
Gly Leu Asn Asp Gln Ala Thr Pro Pro Asp Val Leu Arg Ala Tyr Gly
            100                 105                 110
Phe Tyr Val Cys Pro Gly Pro Pro Asn Asn Glu Glu Tyr Cys Gly Asn
        115                 120                 125
Pro Gln Asp Phe Phe Cys Lys Gln Trp Ser Cys Ile Thr Ser Asn Asp
    130                 135                 140
Gly Asn Trp Lys Trp Pro Val Ser Gln Gln Asp Arg Val Ser Tyr Ser
145                 150                 155                 160
Phe Val Asn Asn Pro Thr Ser Tyr Asn Gln Phe Asn Tyr Gly His Gly
                165                 170                 175
Arg Trp Lys Asp Trp Gln Gln Arg Val Gln Lys Asp Val Arg Asn Lys
            180                 185                 190
```

```
Gln Ile Ser Cys His Ser Leu Asp Leu Asp Tyr Leu Lys Ile Ser Phe
            195                 200                 205

Thr Glu Lys Gly Lys Gln Glu Asn Ile Gln Lys Trp Val Asn Gly Ile
    210                 215                 220

Ser Trp Gly Ile Val Tyr Tyr Gly Ser Gly Arg Lys Lys Gly Ser
225                 230                 235                 240

Val Leu Thr Ile Arg Leu Arg Ile Glu Thr Gln Met Glu Pro Pro Val
                245                 250                 255

Ala Ile Gly Pro Asn Lys Gly Leu Ala Glu Gln Gly Pro Pro Ile Gln
            260                 265                 270

Glu Gln Arg Pro Ser Pro Asn Pro Ser Asp Tyr Asn Thr Thr Ser Gly
        275                 280                 285

Ser Val Pro Thr Glu Pro Asn Ile Thr Ile Lys Thr Gly Ala Lys Leu
    290                 295                 300

Phe Ser Leu Ile Gln Gly Ala Phe Gln Ala Leu Asn Ser Thr Thr Pro
305                 310                 315                 320

Glu Ala Thr Ser Ser Cys Trp Leu Cys
                325

<210> SEQ ID NO 22
<211> LENGTH: 326
<212> TYPE: PRT
<213> ORGANISM: Artificial Sequence
<220> FEATURE:
<223> OTHER INFORMATION: Derived from Env Porcine Endogeneous
      Retrovirus-B
<220> FEATURE:
<221> NAME/KEY: PEPTIDE
<222> LOCATION: (1)..(326)

<400> SEQUENCE: 22

Met His Pro Thr Leu Ser Trp Arg His Leu Pro Thr Arg Gly Gly Glu
1               5                   10                  15

Pro Lys Arg Leu Arg Ile Pro Leu Ser Phe Ala Ser Ile Ala Trp Phe
            20                  25                  30

Leu Thr Leu Thr Ile Thr Pro Gln Ala Ser Ser Lys Arg Leu Ile Asp
        35                  40                  45

Ser Ser Asn Pro His Arg Pro Leu Ser Leu Thr Trp Leu Ile Ile Asp
    50                  55                  60

Pro Asp Thr Gly Val Thr Val Asn Ser Thr Arg Gly Val Ala Pro Arg
65                  70                  75                  80

Gly Thr Trp Trp Pro Glu Leu His Phe Cys Leu Arg Leu Ile Asn Pro
                85                  90                  95

Ala Val Lys Ser Thr Pro Pro Asn Leu Val Arg Ser Tyr Gly Phe Tyr
            100                 105                 110

Cys Cys Pro Gly Thr Glu Lys Glu Lys Tyr Cys Gly Gly Ser Gly Glu
        115                 120                 125

Ser Phe Cys Arg Arg Trp Ser Cys Val Thr Ser Asn Asp Gly Asp Trp
    130                 135                 140

Lys Trp Pro Ile Ser Leu Gln Asp Arg Val Lys Phe Ser Phe Val Asn
145                 150                 155                 160

Ser Gly Pro Gly Lys Tyr Lys Val Met Lys Leu Tyr Lys Asp Lys Ser
                165                 170                 175

Cys Ser Pro Ser Asp Leu Asp Tyr Leu Lys Ile Ser Phe Thr Glu Lys
            180                 185                 190

Gly Lys Gln Glu Asn Ile Gln Lys Trp Ile Asn Gly Met Ser Trp Gly
        195                 200                 205
```

Ile Val Phe Tyr Lys Tyr Gly Gly Ala Gly Ser Thr Leu Thr Ile
210                 215                 220

Arg Leu Arg Ile Glu Thr Gly Thr Glu Pro Pro Val Ala Val Gly Pro
225                 230                 235                 240

Asp Lys Val Leu Ala Glu Gln Gly Pro Pro Ala Leu Glu Pro Pro His
            245                 250                 255

Asn Leu Pro Val Pro Gln Leu Thr Ser Leu Arg Pro Asp Ile Thr Gln
            260                 265                 270

Pro Pro Ser Asn Gly Thr Thr Gly Leu Ile Pro Thr Asn Thr Pro Arg
        275                 280                 285

Asn Ser Pro Gly Val Pro Val Lys Thr Gly Gln Arg Leu Phe Ser Leu
290                 295                 300

Ile Gln Gly Ala Phe Gln Ala Ile Asn Ser Thr Asp Pro Asp Ala Thr
305                 310                 315                 320

Ser Ser Cys Trp Leu Cys
            325

<210> SEQ ID NO 23
<211> LENGTH: 305
<212> TYPE: PRT
<213> ORGANISM: Artificial Sequence
<220> FEATURE:
<223> OTHER INFORMATION: Derived from Env Human Endogenous Retrovirus-T
<220> FEATURE:
<221> NAME/KEY: PEPTIDE
<222> LOCATION: (1)..(305)

<400> SEQUENCE: 23

Met Gly Pro Glu Ala Trp Val Arg Pro Leu Lys Thr Ala Pro Lys Pro
1               5                   10                  15

Gly Glu Ala Ile Arg Leu Ile Leu Phe Ile Tyr Leu Ser Cys Phe Phe
            20                  25                  30

Leu Pro Val Met Ser Ser Glu Pro Ser Tyr Ser Phe Leu Leu Thr Ser
        35                  40                  45

Phe Thr Thr Gly Arg Val Phe Ala Asn Thr Thr Trp Arg Ala Gly Thr
50                  55                  60

Ser Lys Glu Val Ser Phe Ala Val Asp Leu Cys Val Leu Phe Pro Glu
65                  70                  75                  80

Pro Ala Arg Thr His Glu Glu Gln His Asn Leu Pro Val Ile Gly Ala
                85                  90                  95

Gly Ser Val Asp Leu Ala Ala Gly Phe Gly His Ser Gly Ser Gln Thr
            100                 105                 110

Gly Cys Gly Ser Ser Lys Gly Ala Glu Lys Gly Leu Gln Asn Val Asp
        115                 120                 125

Phe Tyr Leu Cys Pro Gly Asn His Pro Asp Ala Ser Cys Arg Asp Thr
    130                 135                 140

Tyr Gln Phe Phe Cys Pro Asp Trp Thr Cys Val Thr Leu Ala Thr Tyr
145                 150                 155                 160

Ser Gly Gly Ser Thr Arg Ser Ser Thr Leu Ser Ile Ser Arg Val Pro
                165                 170                 175

His Pro Lys Leu Cys Thr Arg Lys Asn Cys Asn Pro Leu Thr Ile Thr
            180                 185                 190

Val His Asp Pro Asn Ala Ala Gln Trp Tyr Tyr Gly Met Ser Trp Gly
        195                 200                 205

Leu Arg Leu Tyr Ile Pro Gly Phe Asp Val Gly Thr Met Phe Thr Ile
210                 215                 220

```
Gln Lys Lys Ile Leu Val Ser Trp Ser Ser Pro Lys Pro Ile Gly Pro
225                 230                 235                 240

Leu Thr Asp Leu Gly Asp Pro Ile Phe Gln Lys His Pro Asp Lys Val
            245                 250                 255

Asp Leu Thr Val Pro Leu Pro Phe Leu Val Pro Arg Pro Gln Leu Gln
                260                 265                 270

Gln Gln His Leu Gln Pro Ser Leu Met Ser Ile Leu Gly Gly Val His
            275                 280                 285

His Leu Leu Asn Leu Thr Gln Pro Lys Leu Ala Gln Asp Cys Trp Leu
        290                 295                 300

Cys
305

<210> SEQ ID NO 24
<211> LENGTH: 189
<212> TYPE: PRT
<213> ORGANISM: Artificial Sequence
<220> FEATURE:
<223> OTHER INFORMATION: Derived from Env Human Endogeneous Retrovirus-W
<220> FEATURE:
<221> NAME/KEY: PEPTIDE
<222> LOCATION: (1)..(189)

<400> SEQUENCE: 24

Met Ala Leu Pro Tyr His Ile Phe Leu Phe Thr Val Val Ser Pro Ser
1               5                   10                  15

Phe Thr Leu Thr Ala Pro Pro Cys Arg Cys Met Thr Ser Ser Ser
            20                  25                  30

Pro Tyr Gln Glu Phe Leu Trp Arg Met Gln Arg Pro Gly Asn Ile Asp
        35                  40                  45

Ala Pro Ser Tyr Arg Ser Leu Cys Lys Gly Thr Pro Thr Phe Thr Ala
    50                  55                  60

His Thr His Met Pro Arg Asn Cys Tyr His Ser Ala Thr Leu Cys Met
65                  70                  75                  80

His Ala Asn Thr His Tyr Trp Thr Gly Lys Met Ile Asn Pro Ser Cys
                85                  90                  95

Pro Gly Gly Leu Gly Val Thr Val Cys Trp Thr Tyr Phe Thr Gln Thr
            100                 105                 110

Gly Met Ser Asp Gly Gly Gly Val Gln Asp Gln Ala Arg Glu Lys His
        115                 120                 125

Val Lys Glu Val Ile Ser Gln Leu Thr Arg Val His Gly Thr Ser Ser
130                 135                 140

Pro Tyr Lys Gly Leu Asp Leu Ser Lys Leu His Glu Thr Leu Arg Thr
145                 150                 155                 160

His Thr Arg Leu Val Ser Leu Phe Asn Thr Thr Leu Thr Gly Leu His
                165                 170                 175

Glu Val Ser Ala Gln Asn Pro Thr Asn Cys Trp Ile Cys
            180                 185

<210> SEQ ID NO 25
<211> LENGTH: 295
<212> TYPE: PRT
<213> ORGANISM: Artificial Sequence
<220> FEATURE:
<223> OTHER INFORMATION: Derived from Env Human Endogeneous Retrovirus-R
<220> FEATURE:
<221> NAME/KEY: PEPTIDE
<222> LOCATION: (1)..(295)
```

```
<400> SEQUENCE: 25

Met Leu Gly Met Asn Met Leu Leu Ile Thr Leu Phe Leu Leu Leu Pro
1               5                   10                  15

Leu Ser Met Leu Lys Gly Glu Pro Trp Glu Gly Cys Leu His Cys Thr
            20                  25                  30

His Thr Thr Trp Ser Gly Asn Ile Met Thr Lys Thr Leu Leu Tyr His
                35                  40                  45

Thr Tyr Tyr Glu Cys Ala Gly Thr Cys Leu Gly Thr Cys Thr His Asn
        50                  55                  60

Gln Thr Thr Tyr Ser Val Cys Asp Pro Gly Arg Gly Gln Pro Tyr Val
65                  70                  75                  80

Cys Tyr Asp Pro Lys Ser Ser Pro Gly Thr Trp Phe Glu Ile His Val
                85                  90                  95

Gly Ser Lys Glu Gly Asp Leu Leu Asn Gln Thr Lys Val Phe Pro Ser
            100                 105                 110

Gly Lys Asp Val Val Ser Leu Tyr Phe Asp Val Cys Gln Ile Val Ser
        115                 120                 125

Met Gly Ser Leu Phe Pro Val Ile Phe Ser Ser Met Glu Tyr Tyr Ser
130                 135                 140

Ser Cys His Lys Asn Arg Tyr Ala His Pro Ala Cys Ser Thr Asp Ser
145                 150                 155                 160

Pro Val Thr Thr Cys Trp Asp Cys Thr Thr Trp Ser Thr Asn Gln Gln
                165                 170                 175

Ser Leu Gly Pro Ile Met Leu Thr Lys Ile Pro Leu Glu Pro Asp Cys
            180                 185                 190

Lys Thr Ser Thr Cys Asn Ser Val Asn Leu Thr Ile Leu Glu Pro Asp
        195                 200                 205

Gln Pro Ile Trp Thr Thr Gly Leu Lys Ala Pro Leu Gly Ala Arg Val
210                 215                 220

Ser Gly Glu Glu Ile Gly Pro Gly Ala Tyr Val Tyr Leu Tyr Ile Ile
225                 230                 235                 240

Lys Lys Thr Arg Thr Arg Ser Thr Gln Gln Phe Arg Val Phe Glu Ser
                245                 250                 255

Phe Tyr Glu His Val Asn Gln Lys Leu Pro Glu Pro Pro Leu Ala
            260                 265                 270

Ser Asn Leu Phe Ala Gln Leu Ala Glu Asn Ile Ala Ser Ser Leu His
        275                 280                 285

Val Ala Ser Cys Tyr Val Cys
    290                 295

<210> SEQ ID NO 26
<211> LENGTH: 283
<212> TYPE: PRT
<213> ORGANISM: Artificial Sequence
<220> FEATURE:
<223> OTHER INFORMATION: Derived from Env Human Endogenous Retrovirus-F
<220> FEATURE:
<221> NAME/KEY: PEPTIDE
<222> LOCATION: (1)..(283)

<400> SEQUENCE: 26

Met Asn Ser Pro Cys Asp Arg Leu Gln Gln Phe Ile Gln Val Leu Leu
1               5                   10                  15

Glu Glu Ser Trp Ser Phe Pro Ser Phe Ala Asn Thr Leu His Trp Pro
            20                  25                  30

Glu Asn Leu Leu Ser Tyr Ile Asp Glu Leu Val Trp Gln Gly Ser Leu
```

```
                35                  40                  45
Gln Asn Phe His Gln His Glu Val Arg Phe Asp Lys Pro Pro Leu Arg
 50                  55                  60

Leu Pro Leu Thr Gly Phe Ser Ser Leu Thr Glu Asn Trp Ser Ser Arg
 65                  70                  75                  80

Gln Ala Val Ser Ser Arg Leu Val Ala Thr Ala Ala Ser Pro Pro Ala
                 85                  90                  95

Gly Cys Gln Ala Pro Ile Ala Phe Leu Gly Leu Lys Phe Ser Ser Leu
            100                 105                 110

Gly Pro Ala Arg Lys Asn Pro Ala Leu Cys Phe Leu Tyr Asp Gln Ser
        115                 120                 125

Asn Ser Lys Cys Asn Thr Ser Trp Val Lys Glu Asn Val Gly Cys Pro
    130                 135                 140

Trp His Trp Cys Asn Ile His Glu Ala Leu Ile Arg Thr Glu Lys Gly
145                 150                 155                 160

Ser Asp Pro Met Phe Tyr Val Asn Thr Ser Thr Gly Gly Arg Asp Gly
                165                 170                 175

Phe Asn Gly Phe Asn Leu Gln Ile Ser Asp Pro Trp Asp Pro Arg Trp
            180                 185                 190

Ala Ser Gly Val Asp Gly Gly Leu Tyr Glu His Lys Thr Phe Met Tyr
        195                 200                 205

Pro Val Ala Lys Ile Arg Ile Ala Arg Thr Leu Lys Thr Thr Val Thr
    210                 215                 220

Gly Leu Ser Asp Leu Ala Ser Ser Ile Gln Ser Ala Glu Lys Glu Leu
225                 230                 235                 240

Thr Ser Gln Leu Gln Pro Ala Ala Asp Gln Ala Lys Ser Ser Arg Phe
                245                 250                 255

Ser Trp Leu Thr Leu Ile Ser Glu Gly Ala Gln Leu Leu Gln Ser Thr
            260                 265                 270

Gly Val Gln Asn Leu Ser His Cys Phe Leu Cys
        275                 280

<210> SEQ ID NO 27
<211> LENGTH: 228
<212> TYPE: PRT
<213> ORGANISM: Artificial Sequence
<220> FEATURE:
<223> OTHER INFORMATION: Derived from Env Human T Leukaemia Virus-1
<220> FEATURE:
<221> NAME/KEY: PEPTIDE
<222> LOCATION: (1)..(228)

<400> SEQUENCE: 27

Met Gly Lys Phe Leu Ala Thr Leu Ile Leu Phe Phe Gln Phe Cys Pro
 1               5                  10                  15

Leu Ile Phe Gly Asp Tyr Ser Pro Ser Cys Cys Thr Leu Thr Ile Gly
                20                  25                  30

Val Ser Ser Tyr His Ser Lys Pro Cys Asn Pro Ala Gln Pro Val Cys
             35                  40                  45

Ser Trp Thr Leu Asp Leu Leu Ala Leu Ser Ala Asp Gln Ala Leu Gln
 50                  55                  60

Pro Pro Cys Pro Asn Leu Val Ser Tyr Ser Tyr His Ala Thr Tyr
 65                  70                  75                  80

Ser Leu Tyr Leu Phe Pro His Trp Thr Lys Lys Pro Asn Arg Asn Gly
                85                  90                  95

Gly Gly Tyr Tyr Ser Ala Ser Tyr Ser Asp Pro Cys Ser Leu Lys Cys
```

```
              100                 105                 110
Pro Tyr Leu Gly Cys Gln Ser Trp Thr Cys Pro Tyr Thr Gly Ala Val
            115                 120                 125

Ser Ser Pro Tyr Trp Lys Phe Gln His Asp Val Asn Phe Thr Gln Glu
        130                 135                 140

Val Ser Arg Leu Asn Ile Asn Leu His Phe Ser Lys Cys Gly Phe Pro
145                 150                 155                 160

Phe Ser Leu Leu Val Asp Ala Pro Gly Tyr Asp Pro Ile Trp Phe Leu
                165                 170                 175

Asn Thr Glu Pro Ser Gln Leu Pro Pro Thr Ala Pro Leu Leu Pro
            180                 185                 190

His Ser Asn Leu Asp His Ile Leu Glu Pro Ser Ile Pro Trp Lys Ser
        195                 200                 205

Lys Leu Leu Thr Leu Val Gln Leu Thr Leu Gln Ser Thr Asn Tyr Thr
210                 215                 220

Cys Ile Val Cys
225

<210> SEQ ID NO 28
<211> LENGTH: 224
<212> TYPE: PRT
<213> ORGANISM: Artificial Sequence
<220> FEATURE:
<223> OTHER INFORMATION: Derived from Env Human T Leukaemia Virus-2
<220> FEATURE:
<221> NAME/KEY: PEPTIDE
<222> LOCATION: (1)..(224)

<400> SEQUENCE: 28

Met Gly Asn Val Phe Phe Leu Leu Phe Ser Leu Thr His Phe Pro
1               5                   10                  15

Leu Ala Gln Gln Ser Arg Cys Thr Leu Thr Val Gly Ile Ser Ser Tyr
            20                  25                  30

His Ser Ser Pro Cys Ser Pro Thr Gln Pro Val Cys Thr Trp Asn Leu
        35                  40                  45

Asp Leu Asn Ser Leu Thr Thr Asp Gln Arg Leu His Pro Pro Cys Pro
50                  55                  60

Asn Leu Ile Thr Tyr Ser Gly Phe His Lys Thr Tyr Ser Leu Tyr Leu
65                  70                  75                  80

Phe Pro His Trp Ile Lys Lys Pro Asn Arg Gln Gly Leu Gly Tyr Tyr
                85                  90                  95

Ser Pro Ser Tyr Asn Asp Pro Cys Ser Leu Gln Cys Pro Tyr Leu Gly
            100                 105                 110

Cys Gln Ser Trp Thr Cys Pro Tyr Thr Gly Pro Val Ser Ser Pro Ser
        115                 120                 125

Trp Lys Phe His Ser Asp Val Asn Phe Thr Gln Glu Val Ser Gln Val
    130                 135                 140

Ser Leu Arg Leu His Phe Ser Lys Cys Gly Ser Ser Met Thr Leu Leu
145                 150                 155                 160

Val Asp Ala Pro Gly Tyr Asp Pro Leu Trp Phe Ile Thr Ser Glu Pro
                165                 170                 175

Thr Gln Pro Pro Pro Thr Ser Pro Pro Leu Val His Asp Ser Asp Leu
            180                 185                 190

Glu His Val Leu Thr Pro Ser Thr Ser Trp Thr Thr Lys Ile Leu Lys
        195                 200                 205

Phe Ile Gln Leu Thr Leu Gln Ser Thr Asn Tyr Ser Cys Met Val Cys
```

<210> SEQ ID NO 29
<211> LENGTH: 228
<212> TYPE: PRT
<213> ORGANISM: Artificial Sequence
<220> FEATURE:
<223> OTHER INFORMATION: Derived from Env Simian T Leukaemia Virus-3
<220> FEATURE:
<221> NAME/KEY: PEPTIDE
<222> LOCATION: (1)..(228)

<400> SEQUENCE: 29

```
Met Gly Lys Ser Gly Leu Tyr Phe Ser Leu Ile Cys Phe Tyr Thr Leu
1               5                   10                  15

Phe Pro Ser Ser Phe Gly Asn Pro Ser Arg Cys Thr Leu Phe Ile Gly
            20                  25                  30

Ala Ser Ser Tyr His Ser Asp Pro Cys Gly Ser Asn His Pro Arg Cys
        35                  40                  45

Thr Trp Arg Leu Asp Leu Phe Ser Leu Thr Lys Asp Gln Ser Leu Ser
    50                  55                  60

Pro Pro Cys Pro Gly Leu Val Thr Tyr Ser Gln Tyr His Lys Pro Tyr
65                  70                  75                  80

Ser Leu Tyr Val Phe Pro His Trp Ile Ala Lys Pro Asp Arg Arg Gly
                85                  90                  95

Leu Gly Tyr Tyr Ser Ala Ser Tyr Ser Asp Pro Cys Ala Ile Gln Cys
            100                 105                 110

Pro Tyr Leu Gly Cys Gln Ser Trp Thr Cys Pro Tyr Thr Gly Pro Val
        115                 120                 125

Ser Ser Pro His Trp Lys Tyr Thr Ser Asp Leu Asn Phe Thr Gln Glu
    130                 135                 140

Val Ser Ser Ile Ser Leu His Leu His Phe Ser Lys Cys Gly Tyr Ser
145                 150                 155                 160

Phe Ser Phe Leu Leu Asp Ala Pro Gly Tyr Asp Pro Val Trp Leu Leu
                165                 170                 175

Ser Ser Gln Ala Thr Gln Ile Pro Pro Thr Pro Ala Pro Leu Ile Arg
            180                 185                 190

Asp Pro Asp Leu Gln His Ile Leu Glu Pro Ser Ile Pro Trp Ser Ser
        195                 200                 205

Lys Ile Leu Asn Leu Ile Leu Leu Ala Leu Lys Ser Thr Asn Tyr Ser
    210                 215                 220

Cys Met Val Cys
225
```

<210> SEQ ID NO 30
<211> LENGTH: 215
<212> TYPE: PRT
<213> ORGANISM: Artificial Sequence
<220> FEATURE:
<223> OTHER INFORMATION: Derived from Env Bovine Leukaemia Virus
<220> FEATURE:
<221> NAME/KEY: PEPTIDE
<222> LOCATION: (1)..(215)

<400> SEQUENCE: 30

```
Met Pro Lys Glu Arg Arg Ser Arg Arg Arg Pro Gln Pro Ile Ile Arg
1               5                   10                  15

Trp Val Ser Leu Thr Leu Thr Leu Leu Ala Leu Cys Gln Pro Ile Gln
                20                  25                  30
```

Thr Trp Arg Cys Ser Leu Ser Leu Gly Asn Gln Gln Trp Met Thr Thr
             35                  40                  45

Tyr Asn Gln Glu Ala Lys Phe Phe Ile Ser Ile Asp Gln Ile Leu Glu
 50                  55                  60

Ala His Asn Gln Ser Pro Phe Cys Pro Arg Ser Pro Arg Tyr Thr Leu
 65                  70                  75                  80

Asp Phe Val Asn Gly Tyr Pro Lys Ile Tyr Trp Pro Pro Gln Gly
                 85                  90                  95

Arg Arg Arg Phe Gly Ala Arg Ala Met Val Thr Tyr Asp Cys Glu Pro
                100                 105                 110

Arg Cys Pro Tyr Val Gly Ala Asp His Phe Asp Cys Pro His Trp Asp
                115                 120                 125

Asn Ala Ser Gln Ala Asp Gln Gly Ser Phe Tyr Val Asn His Gln Thr
                130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Asp Pro Pro Gln Pro Asp Phe Pro Gln Leu Asn Ser Asp Trp Val
                180                 185                 190

Pro Ser Val Arg Ser Trp Ala Leu Leu Leu Asn Gln Thr Ala Arg Ala
                195                 200                 205

Phe Pro Asp Cys Ala Ile Cys
                210                 215

<210> SEQ ID NO 31
<211> LENGTH: 224
<212> TYPE: PRT
<213> ORGANISM: Artificial sequence
<220> FEATURE:
<223> OTHER INFORMATION: Derived from Env Human T Leukaemia Virus-4
<220> FEATURE:
<221> NAME/KEY: PEPTIDE
<222> LOCATION: (1)..(224)

<400> SEQUENCE: 31

Met Gly Asn Val Leu Phe Leu Thr Leu Leu Ala Thr Leu Gly Ile Pro
 1               5                  10                  15

Val Leu Gln Ala Ser Arg Cys Thr Ile Thr Val Gly Ile Ser Ser Tyr
                 20                  25                  30

His Ser Ser Pro Cys Ser Pro Ala Gln Pro Leu Cys Thr Trp Ala Leu
                 35                  40                  45

Asp Leu Val Ser Ile Thr Lys Asp Gln Leu Leu Tyr Pro Pro Cys Gln
 50                  55                  60

Asn Leu Ile Thr Tyr Ser Asn Tyr His Lys Thr Tyr Ser Leu Tyr Leu
 65                  70                  75                  80

Phe Pro His Trp Val Gln Lys Pro Leu Arg Arg Gly Leu Gly Tyr Tyr
                 85                  90                  95

Ser Ala Ser Tyr Ser Asp Pro Cys Ser Leu Gln Cys Pro Tyr Leu Gly
                100                 105                 110

Ser Gln Ser Trp Thr Cys Pro Tyr Thr Gly Pro Val Ser Ser Pro Thr
                115                 120                 125

Trp Arg Phe Ser Thr Asp Val Asn Phe Thr Gln Glu Val Ser Arg Val
                130                 135                 140

Ser Leu Lys Leu His Phe Ser Lys Cys Gly Ser Ser Leu Thr Leu Leu
145                 150                 155                 160

```
-continued

Ile Asp Ala Pro Gly Tyr Asp Pro Leu Trp Tyr Leu Thr Ser Glu Pro
                165                 170                 175

Thr Gln Glu Pro Pro Thr Pro Pro Leu Val Ser Asp Ser Asp Leu
            180             185             190

Glu His Val Leu Thr Pro Ser Ala Ser Trp Ala Ser Lys Met Leu Thr
        195                 200                 205

Leu Ile His Leu Thr Leu Gln Ser Thr Asn Tyr Ser Cys Met Val Cys
    210             215                 220
```

RECEPTOR BINDING LIGANDS, THEIR USE IN THE DETECTION OF CELLS WITH BIOLOGICAL INTEREST

Viruses receptor binding domain (RBD) are found in particular in the envelope glycoprotein (Env) of viruses and are able to bind to membrane receptors of different target cells.

Gene therapy strategies to correct a gene deficiency have been based on the transfer properties of gene by retroviruses, the Env of which has been chosen by the experimentator.

Two clinical studies used for the treatment of immunodeficiency of the gamma chain have been based on gene transfer into human haematopoietic stem cell mediated by gammaretrovirus-derived vectors (Cavazzana-Calvo; Science 2000 and Gaspard; Lancet 2004).

Nevertheless, the outcomes of both studies are very different and lymphoproliferative disorders have occurred with some patients at different rates.

One of the aims of the present invention is to provide new receptor binding ligands for the detection of membrane receptors present in a target cell.

Another aim of the invention is to provide an identification process of target cells, in particular of stem cells and cells derived thereof, based on a distinctive array of membrane receptors.

Another aim of the invention is to provide an implementation process for the selection of a sub-population of cells having a biological interest, in particular of stem cells and cells derived thereof.

Another aim of the invention is to provide an amplification process of selected target cells.

Another aim of the invention is to provide a detection process of the presence of specific membrane receptors on a target cell of biological interest.

Another aim of the invention is to provide a process for obtaining said receptor binding ligands.

The present invention relates to the use of at least two soluble receptor binding ligands derived from the soluble part of the glycoprotein of an enveloped virus that interacts with a cellular cognate receptor,

- said receptor binding ligands containing a part or the totality of one of the receptor binding domains (RBD) of said glycoprotein, and,
- said soluble receptor binding ligands being liable to interact with at least one membrane receptor of a target cell, for the identification and quantification of the expression of membrane receptors present on the surface of target cells, said identification and quantification taking place at a given time or during a given time interval, and allowing the determination of a physiological state of said target cell.

By the term "ligand" is meant a polypeptide.

The expression "derived from the soluble part of the glycoprotein of an enveloped virus" means that the receptor binding ligand is a fragment or a part of a glycoprotein contained in the envelope of a virus and can be obtained for example by cloning.

By the term "glycoprotein" is meant an envelope glycoprotein, a coat glycoprotein or a fusion glycoprotein.

The expression "that interacts with a cellular cognate receptor" means that the glycoprotein is liable to be recognized by a receptor present to the surface of a cell.

One or more amino acids can be added to, deleted, or substituted from the peptidic sequence of this fragment or part of glycoprotein.

Receptor binding ligand containing part or the totality of the RBD can be chemically modified to add a fluorochrome.

RBD are found, in particular, in glycoprotein of the envelope of viruses, therefore, the receptor binding ligand contains the total RBD or a fragment or a part of said RBD.

Said part or totality of the RBD is liable to interact with at least one membrane receptor of a target cell.

By "target cell" is meant a cell of biological interest presenting a distinctive array of receptors anchored within the membrane of the cell.

The target cell can be isolated from an animal, for example a mammalian cell, in particular a human being cell and more particularly a stem cell, preferably during a differentiation process, or a cancer cell.

Examples of stem cells, but without being limited to them, are embryonic stem cells, haematopoietic stem cells, neural and mesenchymatous precursor stem cells, cancer stem cells.

The target cell can also be isolated from a tissue or organ.

RBD of the glycoprotein of the virus is able to bind to one or more membrane receptor(s) of a target cell.

By "membrane receptor" it is defined in the invention any protein or polypeptide anchored in the plasma membrane of cells. Said membrane receptor allows the interaction with glycoprotein of viruses.

Preferably the membrane receptors according to the invention are members of the multimembrane-spanning protein family which functions as transporters, such as nutriment and metabolite transporters, i.e. multimembrane-spanning proteins that allow the transport of nutriments and metabolites across the plasma membrane.

All the mammalian cells uptake necessary nutrients via "nutrient or nutriment transporters" on the cell surface and expel catabolites and other components, allowing cell survival (inhibition of apoptosis, inhibition of autophagy, proliferation etc.)

Nutriments or nutrients and metabolites or catabolites are, for instance, carbohydrates, amino acids, inorganic phosphate, nucleosides, lipids, vitamins, heme, ions, etc.

This target cell must be recognized by said RBD.

The expression "said receptor binding ligand being liable to interact with at least one membrane receptor" means that said receptor binding ligand forms a complex with a receptor of the target cells or to several receptors of the target cell by means of the RBD.

The soluble receptor binding ligand can also contain more than one RBD with its complete or partial sequence.

The complex may thus be formed in vitro in the case where the target cells have been previously isolated from an animal.

The complex can also be formed ex vivo.

The complex can also be formed in vivo in the case where the receptor binding ligand is injected to an animal and interact with the target cell in the animal organism.

To obtain an interaction between the receptor and the membrane receptor of the target cell as defined above, the receptor binding ligand must be in a sufficient concentration to form a complex with the membrane receptor.

The expression "identification and the quantification of the expression of membrane receptors present on the surface of target cells" means that when a target cell expresses a membrane receptor, i.e. said receptor is present on the surface of the target cell, therefore a complex is formed between the membrane receptor of a biological interest target cell and the receptor binding ligand.

That complex can be detected if the receptor binding ligand has been for instance, but without being limited to, covalently coupled with a detectable molecule such as an antibody constant fragment (Fc) or a fluorescent compound (cyanins, alexa, quantum dots . . . )

That complex can also be detected if the receptor binding ligand has been tagged with different means well known by a person skilled in the art.

For instance, but without limitations, the tag used in the invention can be Hemaglutinin Tag, Poly Arginine Tag, Poly Histidine Tag, Myc Tag, Strep Tag, Flag Tag, S-Tag, HAT Tag, 3× Flag Tag, Calmodulin-binding peptide Tag, SBP Tag, Chitin-binding domain Tag, GST Tag, Maltose-Binding protein Tag, GFP and EGFP Tag, RFPs Tag, YFP Tag, CFP Tag, T7 tag, V5 tag, Xpress tag and all fluorescent molecules having an emission maximum comprised from 445 nm to 655 nm available from Olympus America Inc.

The use of a receptor binding ligand allows therefore on the one hand the identification of the receptor expressed on the target cell depending to the receptor binding ligand used and on the other hand the quantification of the complex formed, and thus the presence or not of a membrane receptor on the target cell and its quantification.

The expression "at a given time or during a given time interval" means that the detection and/or the quantification of the complex formed can be made just after the contacting of the receptor binding ligand and the membrane receptor of the target cell or after several minutes, in particular from 1 to 59 minutes, or several hours, in particular from 1 to 47 h, preferably 24 h, or days, in particular from 2 to 7 days, preferably 3 days, or several weeks, preferably 3 to 6 weeks when evaluating decay of said membrane receptors on the target cell, after said contacting, depending on the cells and the contacting conditions, in order to evaluate the modification of the expression of membrane receptors.

Contacting conditions include also the temperature that can vary from 0° C. to 37° C., in particular 0, 1, 2, 3 or 4° C., preferably near room temperature, in particular from 18° C. to 25° C., in particular 18, 19, 20, 21, 22, 23, 24 or 25° C., more preferably from 26 to 37° C., in particular 25, 26, 27, 28, 29, 30, 31, 32, 33, 34, 35, 36, or 37° C., preferably 30 or 37° C. depending on the target cells.

The expression "physiological state" means that the receptor binding ligand allows to determine not only the expression of the membrane receptors that are present in the target cell but also if these membrane receptors are present at the cell surface or in intracellular pools. Typically, availability of said membrane receptors at the cell surface is characterized by detection of said membrane receptors after contacting target cells and said receptor binding ligands prior any fixation or permeabilization of the cell membrane. Total, cell surface and intracellular, pools will be detected by contacting after fixation or permeabilization of said target cells with appropriate detergents (Tween, NP40, Nonidet etc.) or fixative solvents (acetone, ethanol, methanol, formaldehyde, paraformaldheyde, etc.). Further, depending on the conditions used during contacting, that is to say incubation conditions (temperature, culture medium, time . . . ), the receptor binding ligand allows to examine the modifications of the membrane receptors, i.e. the variation of expression in the membrane receptors.

Therefore, the receptor binding ligand is a marker of the physiological state of the cell.

One of the advantages of the invention is therefore to provide not only a marker of the physiological state of the cell, but also means to identify, sort out and study cell populations or cell subpopulations of interest, expressing defined soluble receptor binding ligands.

In another embodiment, the receptor binding ligand or marker allows to detect a physiopathologic state of a target cell and to determine what the membrane receptors representative of this state are.

In another embodiment, the present invention relates to the use of at least two soluble receptor binding ligands derived from the soluble part of the glycoprotein of an enveloped virus that interacts with a cellular cognate receptor,
  said receptor binding ligands containing a part or the totality of one of the receptor binding domains (RBD) of said glycoprotein, and
  said soluble receptor binding ligands being liable to interact with said at least one membrane receptor of a target cell,
with the proviso that when only two soluble receptor binding ligands and derived from primate T cell leukaemia viruses (PTLV) are used, said membrane receptor which interacts with said RBD is not GLUTI alone.

Another preferred embodiment of the invention discloses the use such as defined above, wherein said soluble receptor binding ligands are liable to interact with at least two distinct membrane receptors of said target cell.

In this embodiment, a combination of soluble binding ligands comprising two or more soluble binding ligands is used and soluble binding ligands used are different from each other.

The number of soluble binding ligands in the combination can therefore be two, three, four, five, six seven, eight, nine, ten, eleven or twelve, or even more than twelve, depending of the number of receptors being present at the surface of the cell, said soluble binding ligands being all different.

The number of membrane receptors can be two, three, four, five, six seven, eight, nine, ten, eleven or twelve, or even more than twelve, depending of the number of receptors being present at the surface of the cell, and at least two of said receptors are distinct.

In this embodiment, one of the receptors can be GLUT1.

Two or more soluble binding ligands can interact with the same membrane receptor.

One of the advantages of the invention is therefore to provide information on the physiological state of the cell or means to identify, sort out and study cell populations or cell subpopulations of interest with a combination of soluble binding ligands. In another embodiment, the invention discloses the use such as defined above, wherein said glycoprotein is a glycoprotein from a gammaretrovirus such as murine, feline, or gibbon ape leukaemia virus (MLV, FeLV, GaLV) or from a deltaretrovirus such as the human and simian T cell leukaemia viruses (HTLV and STLV) or bovine leukaemia virus (BLV), or from a rhabdovirus, such as vesicular stomatitis virus (VSV).

According to the invention, the viruses are preferably gamma and deltaretroviruses whose already known receptors have all been shown to be members of the multimembrane-spanning protein family. Retroviruses are well known in the art.

Two types of retroviruses exist: exogenous (absent from the germ line) and endogenous retroviruses (present in the genome of the germ line). As example, the retroviruses according to the invention can be chosen among the following exogenous retroviruses: Gammaretrovirus, Deltaretrovirus, including: Bovine leukemia virus and Human T-lymphotropic virus. The retroviruses can also be chosen among the endogenous retroviruses of the Class I endogenous retroviruses which are most similar to the gammaretroviruses.

The gamma and deltaretroviruses encode an Env glycoprotein which is a protein of the mature retrovirus virons. Env protein is one of the retrovirus proteins which is synthesized in the form of a propeptide. Env protein is dived in two polypeptides: the transmembrane (TM) and the cell surface (SU) components. The cleavage is achieved in Golgi apparatus by furine peptidase.

The SU and TM domains are, in the native virus, associated by disulfide bridges.

The SU domain contains two major subdomains: a domain of interaction with the TM domain and the RBD, RBD being liable to interact with host cell membrane receptors.

FIG. 1 represents the native Env glycoprotein of HTLV-1.

According to the invention, the viruses are also rhabdoviruses which are not retroviruses but that encode a glycoprotein present in the envelope of the virus and that contains a RBD.

According to a preferred embodiment, receptor binding ligands are selected from the SEQ ID NO:1 to SEQ ID NO:31.

The SEQ IDs 1 to 31 are constituted of the signal peptide when known, the receptor binding domain, the proline rich region (PRR) when known and the CXXC motif located downstream of the PRR.

Another preferred embodiment of the invention discloses the use as previously disclosed, wherein said soluble receptor binding ligands are isolated from the glycoprotein belonging to the following viruses: Amphotropic MLV (ampho, SEQ ID NO:1), Gibbon Ape Leukemia virus (GALV, SEQ ID NO:2), Feline endogenous virus (RD114, SEQ ID NO:3), vesicular stomatitis virus (VSV, SEQ ID NO:4), Xenotropic Murine Leukaemia Virus (NZB, Xeno, SEQ ID NO: 10), Feline Leukaemia Virus C (FelV, SEQ ID NO: 19), Env Koala Retrovirus (KoV, SEQ ID NO: 20), Env Porcine Endogeneous Retrovirus-B (Perv B, SEQ ID NO: 22), Human T Leukaemia Virus-1 (HTLV1, SEQ ID NO:27), Human T Leukaemia Virus-2 (HTLV2, SEQ ID NO:28), Human T Leukaemia Virus-4 (HTLV4, SEQ ID NO:31), or Env Bovine Leukaemia Virus (BLV, SEQ ID NO: 30).

Another particular embodiment of the invention relates to the use such as defined above, wherein said membrane receptors are selected from the list consisting in CAT1, PiT2, XPR1, SMIT1, PiT1, ASCT1/$ATB^0$, FLVCR, PAR1, PAR2, GLUT1.

The above mentioned membrane receptors are disclosed in Manel et al. Frontiers in Bioscience, 9, 3218-3241, 2004.

In another preferred embodiment, the invention relates to the use such as defined above, wherein said target cells are animal stem cells, in particular human stem cells or cancer stem cells.

By stem cells, it is defined in the invention cells able to differentiate into a diverse range of specialized cell types. These stem cells are defined according to the invention such that they have an intrinsic potential to differentiate, from one (unipotent) or two (dipotent), into n (multipotent) differentiated cells, n being more than 2.

The invention concerns pluripotent cells that are the progeny of totipotent cells. In the pluricellular organisms, a totipotent cell, which results from the fusion between male and female gamete, is able to differentiate into all the cells that will constitute the organism. The first divisions of this totipotent cell give, by mitosis, some pluripotent cells. These pluripotent cells have ever acquired a specification, and have lost their ability to give all the differentiated cells.

Therefore stem cells according to the invention concern pluripotent, multipotent, dipotent and unipotent cells. In the invention, the embryonic stem cell (ESC), corresponding to the cell formed by the fusion between male and female gametes can also be used.

Stem cells concern also induced pluripotent stem cells (IPS).

In one particular embodiment, the embryonic stem cells derived from human, human embryonic stem cells (HESC) are preferably excluded from the use to the implementation of the process of the invention. So, in this particular embodiment, stem cells concern all the animal stem cells provided that said stem cells are not human embryonic stem cells.

In another particular embodiment, the invention relates to the use previously defined, wherein said target cells are haematopoietic stem cells.

Hematopoietic stem cells are multipotent stem cells able to differentiate into all the circulating blood cells, such that erythrocyte, macrophages, monocytes.

In another particular embodiment, the invention relates to the use previously defined, wherein said at least two soluble receptor binding ligands are a set of two soluble receptor binding ligands selected from the list as defined above, and allows the identification and the quantification of the expression of at least two membrane receptors present on the surface of target cells.

Some of the receptors binding ligands of the invention, wherein the RBD of glycoproteins belongs for example to 10A1 MLV, are able to interact with two membrane receptors such as PiT1 and PiT2 and therefore are used to determine the expression and quantification of both receptors.

Other receptor binding ligands of the invention are selective of one membrane receptor and therefore, in this embodiment, the determination of the expression of at least two membrane receptors necessitates the use of two receptor binding ligands.

The invention discloses, in one preferred embodiment, the use as defined above, wherein said receptor binding ligand is a set of two receptor binding ligands wherein the RBD of glycoproteins are selected from the glycoprotein belonging to the following viruses: Amphotropic MLV (ampho) and Gibbon Ape Leukemia virus (GALV).

The invention discloses, in one preferred embodiment, the use as defined above, wherein said receptor binding ligand is a set of two receptor binding ligands wherein the RBD of glycoproteins are selected from the glycoprotein belonging to the following viruses: Amphotropic MLV (ampho), Feline endogenous virus (RD114).

The invention discloses, in one preferred embodiment, the use as defined above, wherein said receptor binding ligand is a set of two receptor binding ligands wherein the RBD of glycoproteins are selected from the glycoprotein belonging to the following viruses: Amphotropic MLV (ampho) and vesicular stomatitis virus (VSV).

The invention discloses, in one preferred embodiment, the use as defined above, wherein said receptor binding ligand is a set of two receptor binding ligands wherein the RBD of glycoproteins are selected from the glycoprotein belonging to the following viruses: Gibbon Ape Leukemia virus (GALV) and Feline endogenous virus (RD114).

The invention discloses, in one preferred embodiment, the use as defined above, wherein said receptor binding ligand is a set of two receptor binding ligands wherein the RBD of glycoproteins are selected from the glycoprotein belonging to the following viruses: Gibbon Ape Leukemia virus (GALV) and vesicular stomatitis virus (VSV).

The invention discloses, in one preferred embodiment, the use as defined above, wherein said receptor binding ligand is a set of two receptor binding ligands wherein the RBD of glycoproteins are selected from the glycoprotein belonging to the following viruses: Feline endogenous virus (RD114) and vesicular stomatitis virus (VSV).

The invention discloses, in one preferred embodiment, the use as defined above, wherein said receptor binding ligand is a set of two receptor binding ligands wherein the RBD of glycoproteins are selected from the glycoprotein belonging to the following viruses: Gibbon Ape Leukemia virus (GALV) and Env Bovine Leukaemia Virus (BLV).

Such a combination is used as an example (example 6, FIG. 15).

In one particular embodiment, the invention discloses the use as defined above, wherein said receptor binding ligand is a set of three to more than twelve receptor binding ligands according to the invention, in particular three, four, five, six seven, eight, nine, ten, eleven, or twelve, said receptor binding ligands being isolated from the glycoprotein belonging to the following viruses: Amphotropic MLV (ampho, SEQ ID NO:1), Gibbon Ape Leukemia virus (GALV, SEQ ID NO:2), Feline endogenous virus (RD114, SEQ ID NO:3), vesicular stomatitis virus (VSV, SEQ ID NO:4), Xenotropic Murine Leukaemia Virus (NZB, Xeno, SEQ ID NO: 10), Feline Leukaemia Virus C (FelV, SEQ ID NO: 19), Env Koala Retrovirus (KoV, SEQ ID NO: 20), Env Porcine Endogeneous Retrovirus-B (Perv B, SEQ ID NO: 22), Human T Leukaemia Virus-1 (HTLV1, SEQ ID NO:27), Human T Leukaemia Virus-2 (HTLV2, SEQ ID NO:28), Human T Leukaemia Virus-4 (HTLV4, SEQ ID NO:31), or Env Bovine Leukaemia Virus (BLV, SEQ ID NO: 30).

In one particular embodiment, the invention discloses the use as defined above, wherein said receptor binding ligand is a set of ten receptor binding ligands wherein the RBD of glycoproteins are selected from the glycoprotein belonging to the following viruses: Amphotropic MLV (ampho), Feline endogenous virus (RD114), Gibbon Ape Leukemia virus (GALV), Xenotropic Murine Leukaemia Virus (NZB, Xeno), Env Koala Retrovirus (KoV), Env Porcine Endogeneous Retrovirus-B (Perv B), Human T Leukaemia Virus-2 (HTLV2), Human T Leukaemia Virus-4 (HTLV4), Env Bovine Leukaemia Virus (BLV), Env Feline Leukaemia Virus C (FelV).

Such a combination is used as an example (example 4, FIGS. 10 to 12).

In one particular embodiment, the invention discloses the use as defined above, wherein said receptor binding ligand is a set of eight receptor binding ligands wherein the RBD of glycoproteins are selected from the glycoprotein belonging to the following viruses: Amphotropic MLV (ampho), Feline endogenous virus (RD114), Xenotropic Murine Leukaemia Virus (NZB, Xeno), Env Koala Retrovirus (KoV), Env Porcine Endogeneous Retrovirus-B (Perv B), Human T Leukaemia Virus-2 (HTLV2), Human T Leukaemia Virus-4 (HTLV4), Env Bovine Leukaemia Virus (BLV).

Such a combination is used as an example (example 3, FIGS. 4 to 9).

In one particular embodiment, the invention discloses the use as defined above, wherein said receptor binding ligand is a set of five receptor binding ligands wherein the RBD of glycoproteins are selected from the glycoprotein belonging to the following viruses: Amphotropic MLV (ampho), Gibbon Ape Leukemia virus (GALV), Feline endogenous virus (RD114), Human T Leukaemia Virus-1 (HTLV1), Env Bovine Leukaemia Virus (BLV).

Such a combination is used as an example (example 5, FIGS. 13 and 14).

In one particular embodiment, the invention discloses the use as defined above, wherein said receptor binding ligand is a set of the four receptor binding ligands wherein the RBD of glycoproteins are selected from the glycoprotein belonging to the following viruses: Amphotropic MLV (ampho), Gibbon Ape Leukemia virus (GALV), Feline endogenous virus (RD114) and vesicular stomatitis virus (VSV).

In one particular embodiment, the invention discloses the use as defined above, wherein said receptor binding ligand is a set of three receptor binding ligands wherein the RBD of glycoproteins are selected from the glycoprotein belonging to the following viruses: Amphotropic MLV (ampho), Gibbon Ape Leukemia virus (GALV) and Feline endogenous virus (RD114).

In one particular embodiment, the invention discloses the use as defined above, wherein said receptor binding ligand is a set of three receptor binding ligands wherein the RBD of glycoproteins are selected from the glycoprotein belonging to the following viruses: Amphotropic MLV (ampho), Gibbon Ape Leukemia virus (GALV) and vesicular stomatitis virus (VSV).

In one particular embodiment, the invention discloses the use as defined above, wherein said receptor binding ligand is a set of three receptor binding ligands wherein the RBD of glycoproteins are selected from the glycoprotein belonging to the following viruses: Gibbon Ape Leukemia virus (GALV), Feline endogenous virus (RD114) and vesicular stomatitis virus (VSV).

In one particular embodiment, the invention discloses the use as defined above, wherein said receptor binding ligand is a set of three receptor binding ligands wherein the RBD of glycoproteins are selected from the glycoprotein belonging to the following viruses: Amphotropic MLV (ampho), Feline endogenous virus (RD114) and vesicular stomatitis virus (VSV).

In one particular embodiment, the invention discloses the use as defined above, wherein said receptor binding ligand is a set of three receptor binding ligands wherein the RBD of glycoproteins are selected from the glycoprotein belonging to the following viruses: Amphotropic MLV (ampho), Gibbon Ape Leukemia virus (GALV), and vesicular stomatitis virus (VSV).

In one particular embodiment, the invention discloses the use as defined above, wherein said receptor binding ligand is a set of three receptor binding ligands wherein the RBD of glycoproteins are selected from the glycoprotein belonging to the following viruses: Amphotropic MLV (ampho), Gibbon Ape Leukemia virus (GALV), and Env Bovine Leukaemia Virus (BLV).

Such a combination is used as an example (example 6, FIG. 16).

In another particular embodiment, the invention relates to the use previously defined, for the implementation of a selection process of target cells, having a defined physiological state, in particular of stem cells sub-population expressing said at least one membrane receptor.

The invention allows, by using the receptor binding ligand defined above, the selection of a sub group of cells, preferably stem cells, that express at least one of the above mentioned membrane receptor.

Thus, it is possible to discriminate in a heterogeneous population of cells, cells expressing at least one membrane receptor of interest and showing the best physiological state depending on the incubation conditions.

In another aspect, the invention relates to a process of identification and quantification of the expression of at least one membrane receptor to a glycoprotein RBD of target cells, comprising the following steps:
- a. contacting at least two soluble receptor binding ligands, as defined in claim 1, optionally marked with a tag, with a target cell to form at least two complexes, each complex being constituted by one said receptor binding ligand and one said membrane receptor of said target cell,
- b. identifying each complex formed,
- c. quantifying the expression of each membrane receptor of said target cell able to form said complex.
- d. optionally, distinguishing receptors expressed to the surface of the membrane of the target cell (prior fixation or permeabilization) from the total receptors expressed within the target cell (after fixation or permeabilization).

According to the invention, the receptor binding ligands are incubated with cells that are liable to express at least one membrane receptor liable to interact with said receptor binding ligand.

When the receptor binding ligand interacts with its "corresponding" membrane receptor, a complex is formed. By corresponding membrane receptor, it is meant a receptor that is able to interact with the RBD contained in said receptor binding ligand.

The complex formed can be easily detected by using routine protocols known in the art.

When the receptor binding ligand according to the invention is tagged, the complex formed between said soluble protein containing an RBD and the "corresponding receptor" can be detected any detecting methods known by a skilled person.

For instance, if the tag is a fluorescent protein, the complex is detected by the detection of the fluorescence by appropriate apparatus (fluorescent microscope, Flow cytometer . . . ). If the tag is a tag corresponding to a part of a well known protein (HA, His, GFP, GST . . . ), antibodies directed against said tag can be used. Said antibodies directed against said tag are coupled with molecule allowing their detection by fluorescent, chemiluminescent, magnetic or colorimetric means.

Fixed and permeabilized target cells (by techniques well known by a person skilled in the art) allow to determine the total content of cells receptors and thus to distinguish surface receptors expression from total expression of the receptors in the cell.

Therefore, the process of the invention leads to the identification and quantification of cells expressing membrane receptors allowing to obtain:
- on the one hand selecting cells that express at least one particular receptor and eliminating cells that does not express said at least one particular receptor,
- on the other hand selecting cells that do not express at least one particular receptor and thus eliminating cells that express said at least one particular receptor In one particular embodiment, the invention relates to a process as defined above, wherein said target cells are animal stem cells, in particular human stem cells.

In one particular embodiment, the invention relates to a process as defined above, wherein said target cells are haematopoietic stem cells.

In another aspect, the invention relates to a process of selection of target cells expressing at least one particular membrane receptor to a glycoprotein RBD in a given amount of expression, comprising the following steps:
- a. contacting at least two soluble receptor binding ligands, as defined in claim 1, optionally marked with a tag, with a target cell to form at least two complexes, each complex being constituted by one said receptor binding ligand and one said membrane receptor of said target cell,
- b. detecting each complex formed and quantifying said each complex formed at an instant T1,
- c. detecting and quantifying said each complex formed at a second instant T2, T2 being higher than T1,
- b. selecting at T2 said target cells presenting a variation in the expression of at least one particular membrane receptor having formed said complex.

After the formation of the complex between receptor binding ligand according to the invention and its corresponding receptor, cells expressing said membrane receptor can be detected and followed during the time, between T1 and T2, for example after several minutes, in particular from 1 to 59 minutes, or several hours, in particular from 1 to 47 h, preferably 24 h, or days, in particular from 2 to 7 days, preferably 3 days, or several weeks, preferably 2 to 6 weeks, after said contacting, depending on the cells and the contacting conditions to examine the changes in their physiological state.

Cells exhibiting the desired physiological state in function of the membrane receptors expressed and quantified can be isolated from those that does not exhibit said desired physiological state.

In the case where the receptor binding ligand according to the invention is tagged with a fluorescent protein, cells expressing membrane receptor complexed with the receptor binding ligand according to the invention can be isolated from the others by using a flow cytometer/cell sorter that allows the specific cell sorting based on the selective detection of fluorescence.

In the case where the tag used corresponds to a part of a well known protein, a second antibody is used, said antibody being capable to specifically interact with said tag. This antibody is preferably coupled with a fluorescent molecule (fluorescent dye), to allow the cell sorting by using a flow cytometer. Another possibility is to use an antibody coupled with magnetic compound. In this case, cells expressing the membrane receptor interacting with the receptor binding ligand according to the invention are isolated by using a magnet.

These sorting methods are commonly used in the art.

In one particular embodiment, the invention relates to a process as defined above, wherein said target cells are animal stem cells, in particular human stem cells or cancer stem cells.

In one particular embodiment, the invention relates to a process as defined above, wherein said target cells are haematopoietic stem cells.

The FIGS. 2 and 3 show an example of the physiological state modifications observed after one or three days of contacting umbilical cord blood with the receptor binding ligands of the invention for 30 minutes at 37° C.

In another aspect, the present invention relates to a process of amplification of target cells expressing at least one particular membrane receptor to a glycoprotein RBD in a given amount of expression, comprising the following steps:
- a. contacting at least two soluble receptor binding ligands, as defined in claim 1, optionally marked with a tag, with a target cell to form at least two complexes, each complex being constituted by one said receptor binding ligand and one said membrane receptor of said target cell, b. detecting each complex formed and quantifying said each complex formed at an instant T1, c. detecting and quantifying said each complex formed at a second instant T2, T2 being higher than T1, d. selecting at T2 said target cells presenting a variation in the expression of at least one particular membrane receptor having formed said complex.

e. sorting out and amplifying said selected target cells.

Steps a-d have been explained above. Thus, when preferred target cells have been isolated, they are amplified by cultivating them in an appropriate culture media containing nutriments and gas necessary for the achievement of the cell division, i.e. the achievement of mitosis.

An "appropriate culture medium", means a medium comprising nutriments necessary for the survival of cultured cells. This medium is classically pH-buffered, and has glucose concentration, growth factors, and nutrient composition that is specific for in vitro cell survival.

The growth factors used to supplement media are often derived from animal blood, such as calf serum. Moreover, recombinant specific growth factor can be added to specifically initiate a specific cellular process, such as proliferation.

In one particular embodiment, the invention relates to a process as defined above, wherein said target cells are animal stem cells, in particular human stem cells.

In one particular embodiment, the invention relates to a process as defined above, wherein said target cells are haematopoietic stem cells.

The invention also relates to a receptor binding ligand derived from the soluble part of an envelope glycoprotein of a virus as defined above, said receptor binding ligand containing a part or the totality of one of the receptor binding domains (RBD) of said glycoprotein, and said soluble receptor binding ligand being liable to interact with said at least one membrane receptor of a target cell.

In one other preferred embodiment, the invention relates to a receptor binding ligand as defined above, wherein said glycoprotein is a glycoprotein from a gammaretrovirus such as murine leukaemia virus (MLV) or from a deltaretrovirus such as human T leukaemia virus (HTLV) or bovine leukaemia virus (BLV), or from a rhabdovirus, such as vesicular stomatitis virus (VSV).

In one other preferred embodiment, the invention relates to a receptor binding ligand as defined above, wherein said soluble receptor binding ligand are isolated from the glycoprotein belonging to the following viruses: Amphotropic MLV (ampho, SEQ ID NO:1), Gibbon Ape Leukemia virus (GALV, SEQ ID NO:2), Feline endogenous virus (RD114, SEQ ID NO:3), vesicular stomatitis virus (VSV, SEQ ID NO:4).

In one other preferred embodiment, the invention relates to a receptor binding ligand according to the above definition, wherein said target cells are animal stem cells, in particular human stem cells or cancer stem cells.

In one other preferred embodiment, the invention relates to a receptor binding ligand such as defined above, wherein said target cells are haematopoietic stem cells or cancer stem cells.

The following figures and examples illustrate the invention.

FIG. 1 corresponds to the schematic representation of the mature Env protein of HTLV-1 (as a prototypic deltaretrovirus Env) and common motifs in the SU with Friend-MLV (as a prototypic gammaretrovirus Env). TM corresponds to the transmembrane domain and SU corresponds to the surface domain. RBD corresponds to the domain of SU that interact with the membrane receptor of the target cell.

FIGS. 2A to J correspond to the cell surface expression kinetics of Gammaretrovirus membrane receptors of CD34+ umbilical cord blood stem cells (human) from day 0 to day 1 of amplification according to different amplification protocols and as detected after contacting with Ampho and GALV receptor binding ligands at 37° C. for 30 minutes.

Figure 1:
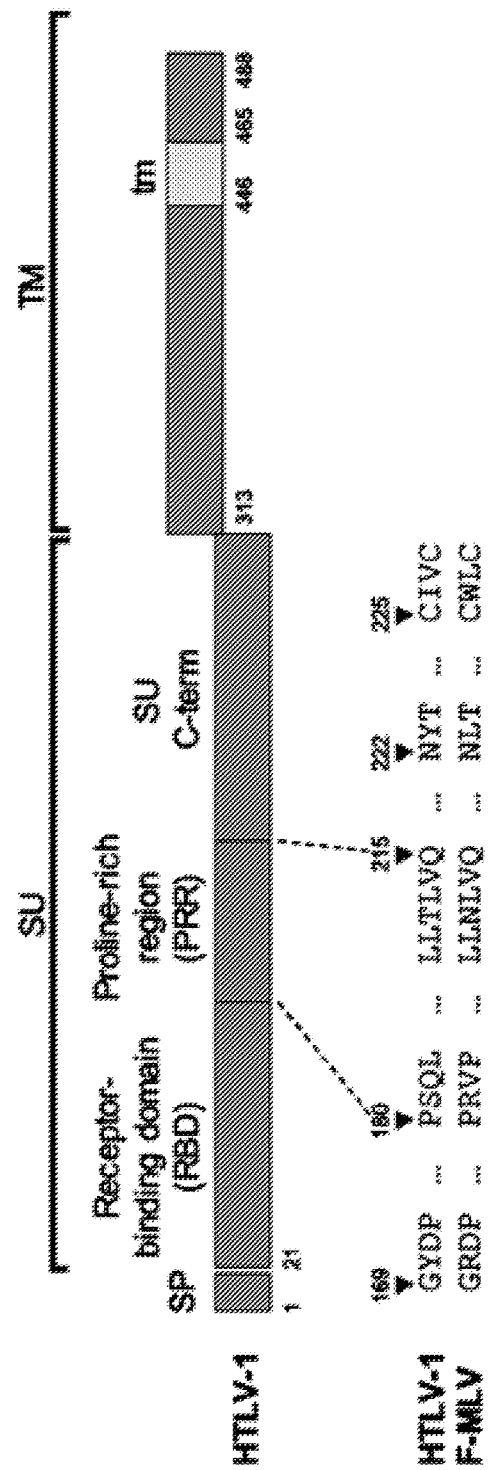
Figure 2:
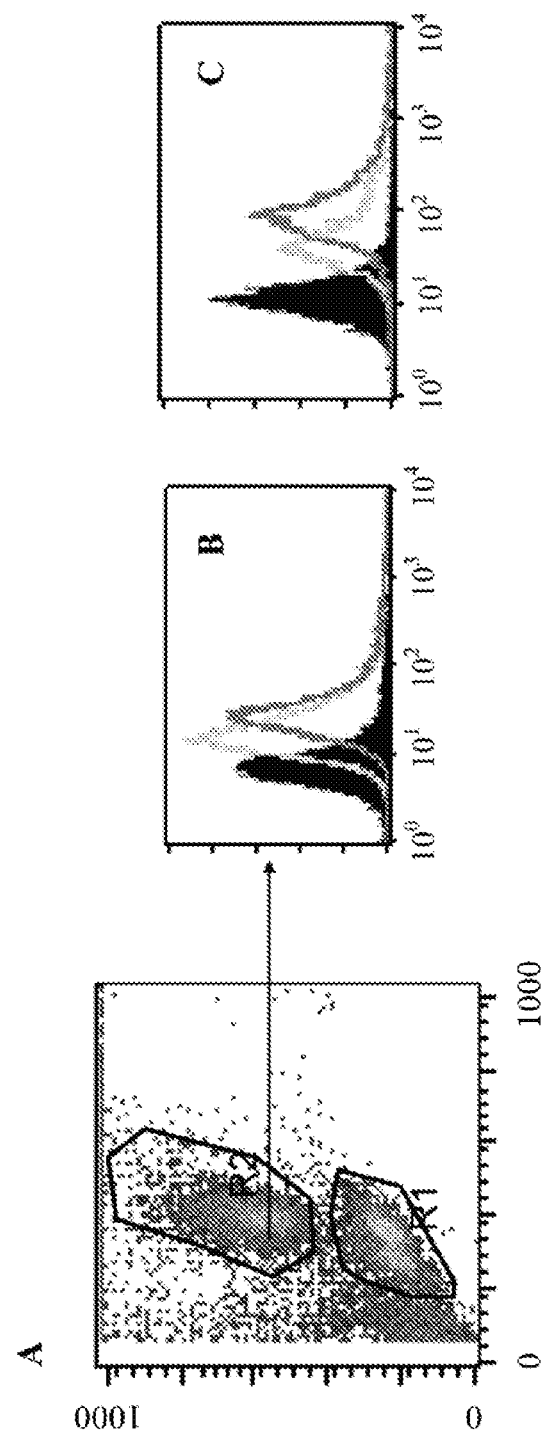
FIG. 2A represents the FACS of CD34+ umbilical cord blood cells isolated after Ficoll and CD34+ Miltenyi selection kits.
FIG. 2B represents the Fisher amplification protocols at Day=0 (Black: Mock, light grey (ampho), Dark grey GALV) of R2 cells of FIG. 2A (upper zone).
FIG. 2C represents the Fisher amplification protocols at Day=1 (Black: Mock, light grey (ampho), Dark grey GALV) of R2 cells of FIG. 2A (upper zone).
FIG. 2D represents the FACS obtained with R1 zone of FIG. 2A after selection of CD34+ hematopoietic stem cells using Miltenyi selection kits.
FIGS. 2E and 2H represents the Fisher amplification protocols at Day=0 and Day=1 respectively (Black: Mock, light grey (ampho), Dark grey GALV) of R6 zone of FIG. 2D (upper left zone).
FIGS. 2F and 2I represents the Fisher amplification protocols at Day=0 and Day=1 respectively (Black: Mock, light grey (ampho), Dark grey GALV) of R3 zone of FIG. 2D (upper right zone).
Figure 2:
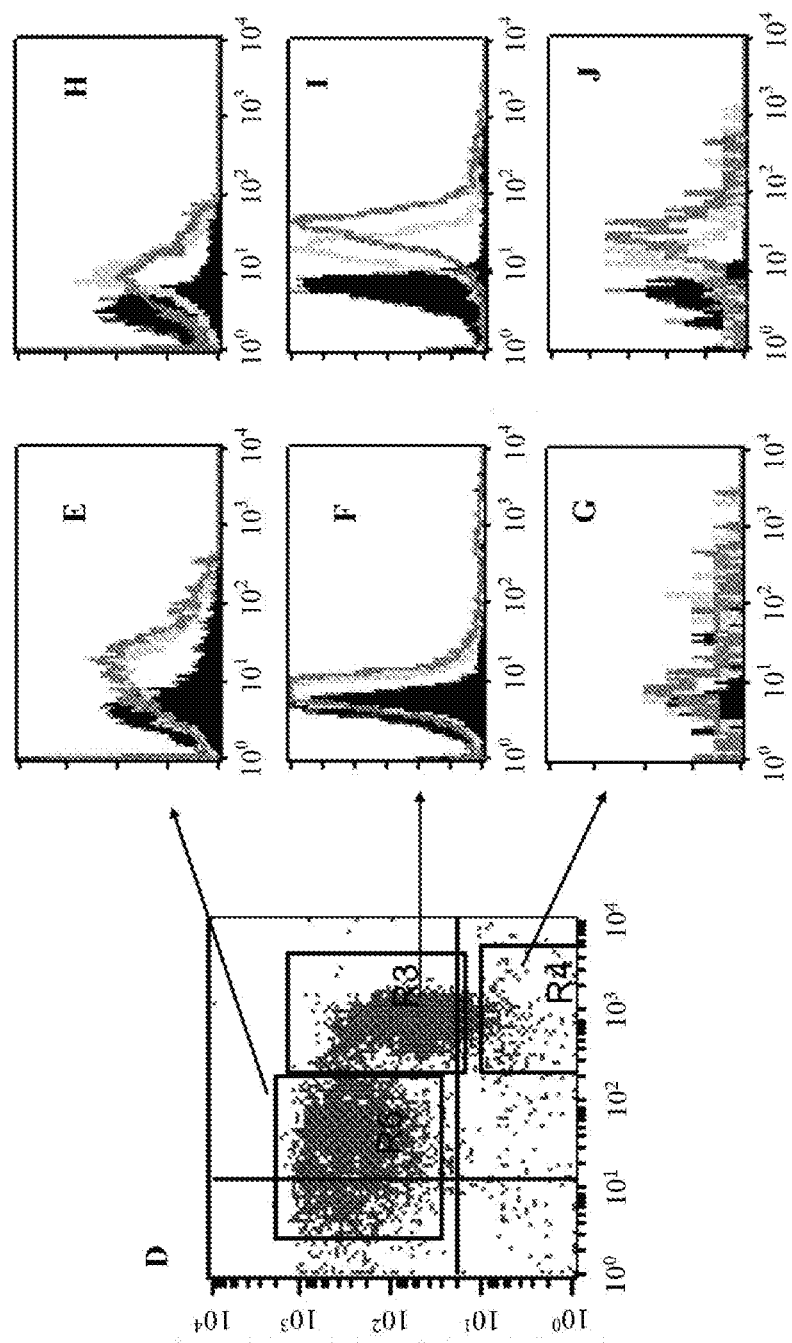

FIGS. 2EG and 2J represents the Fisher amplification protocols at Day=0 and Day=1 respectively (Black: Mock, light grey (ampho), Dark grey GALV) of R4 zone of FIG. 2D (lower right zone).

Figure 3:
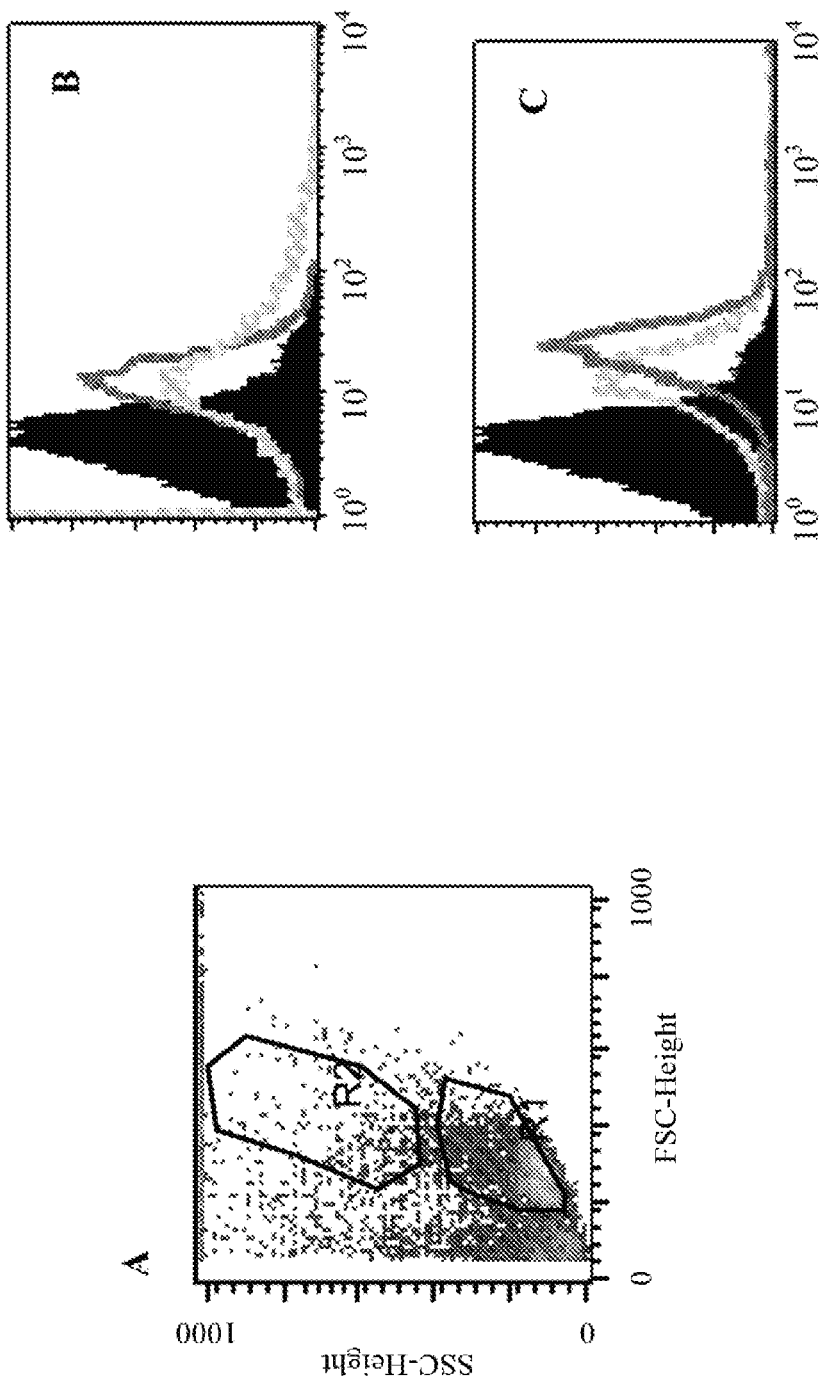
Figure 3:
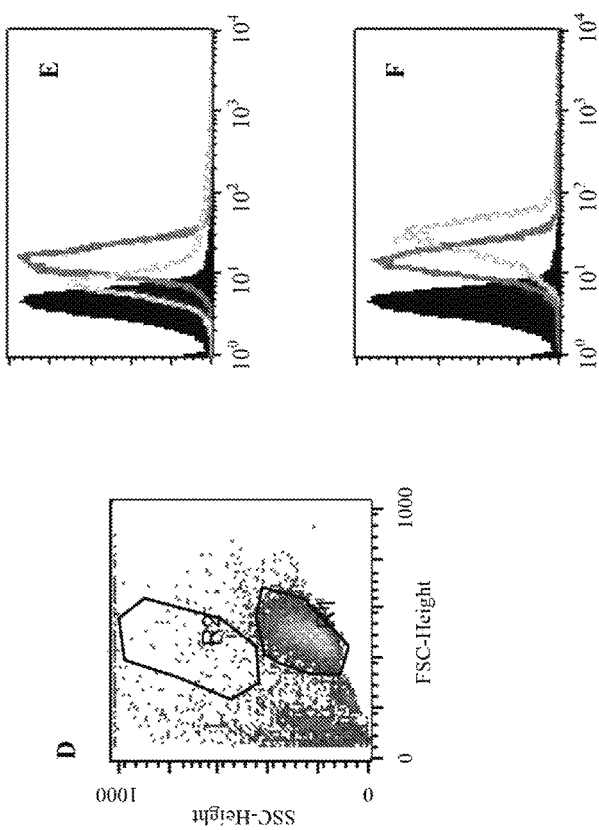
Figure 4:
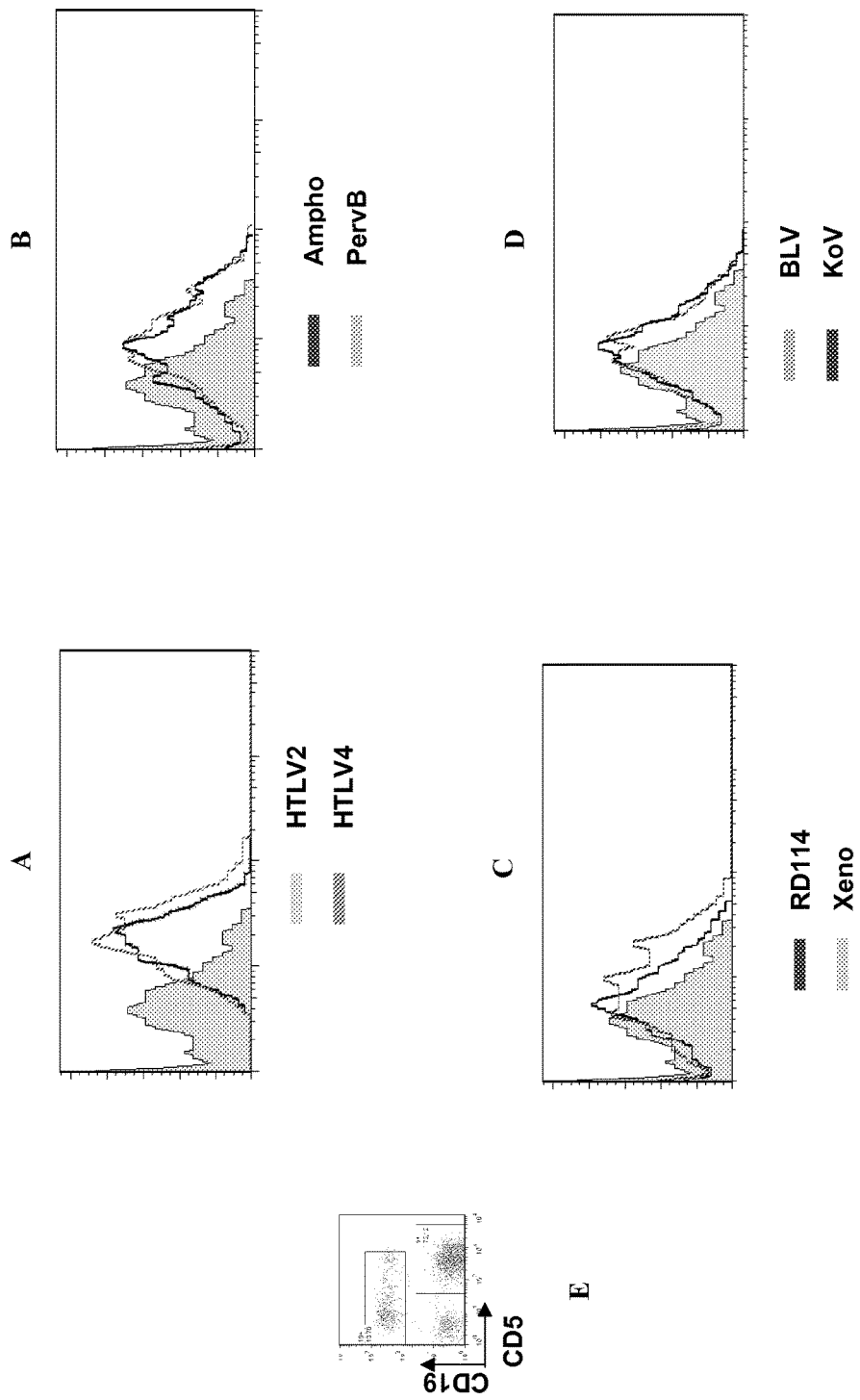
Figure 5:
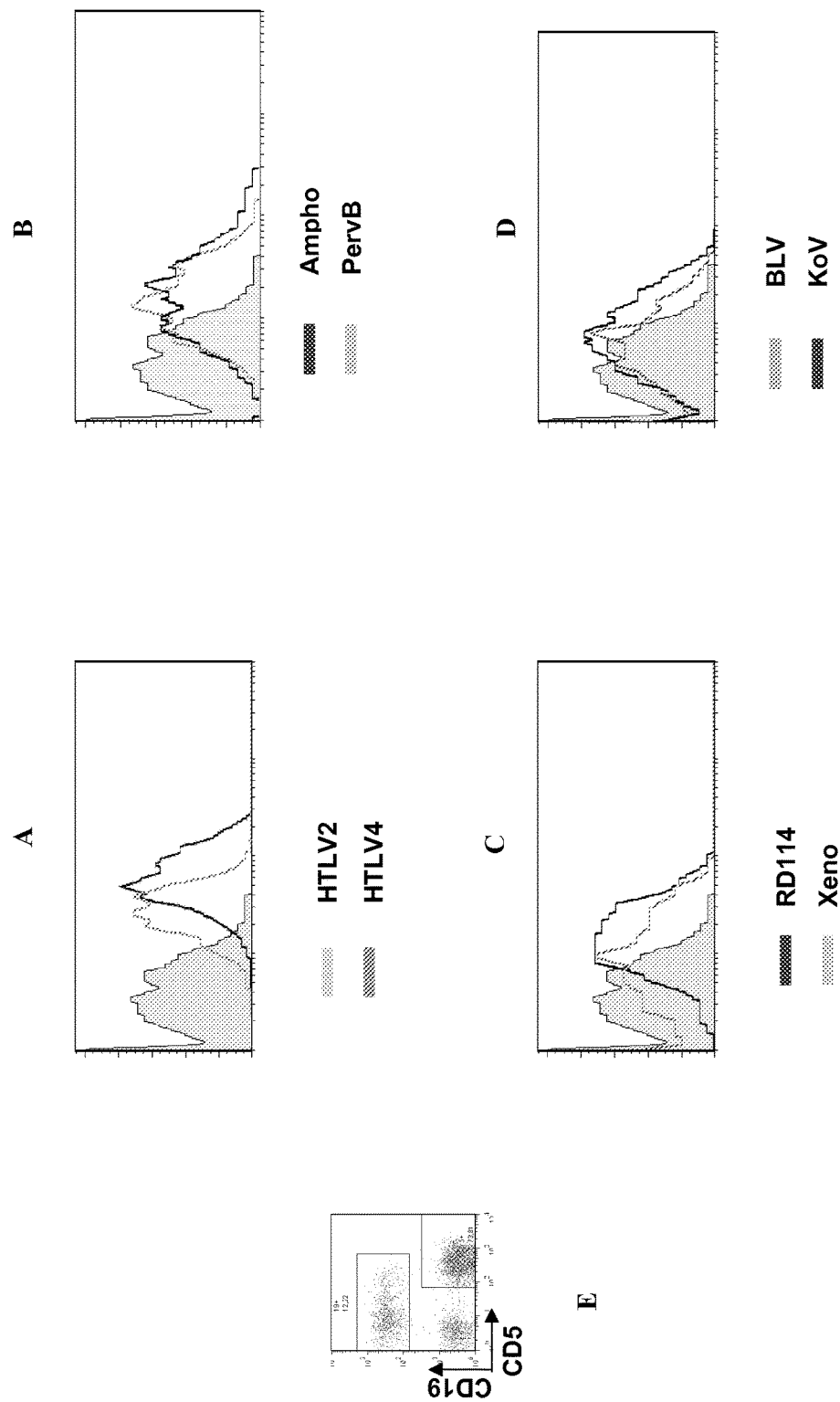
Figure 6:
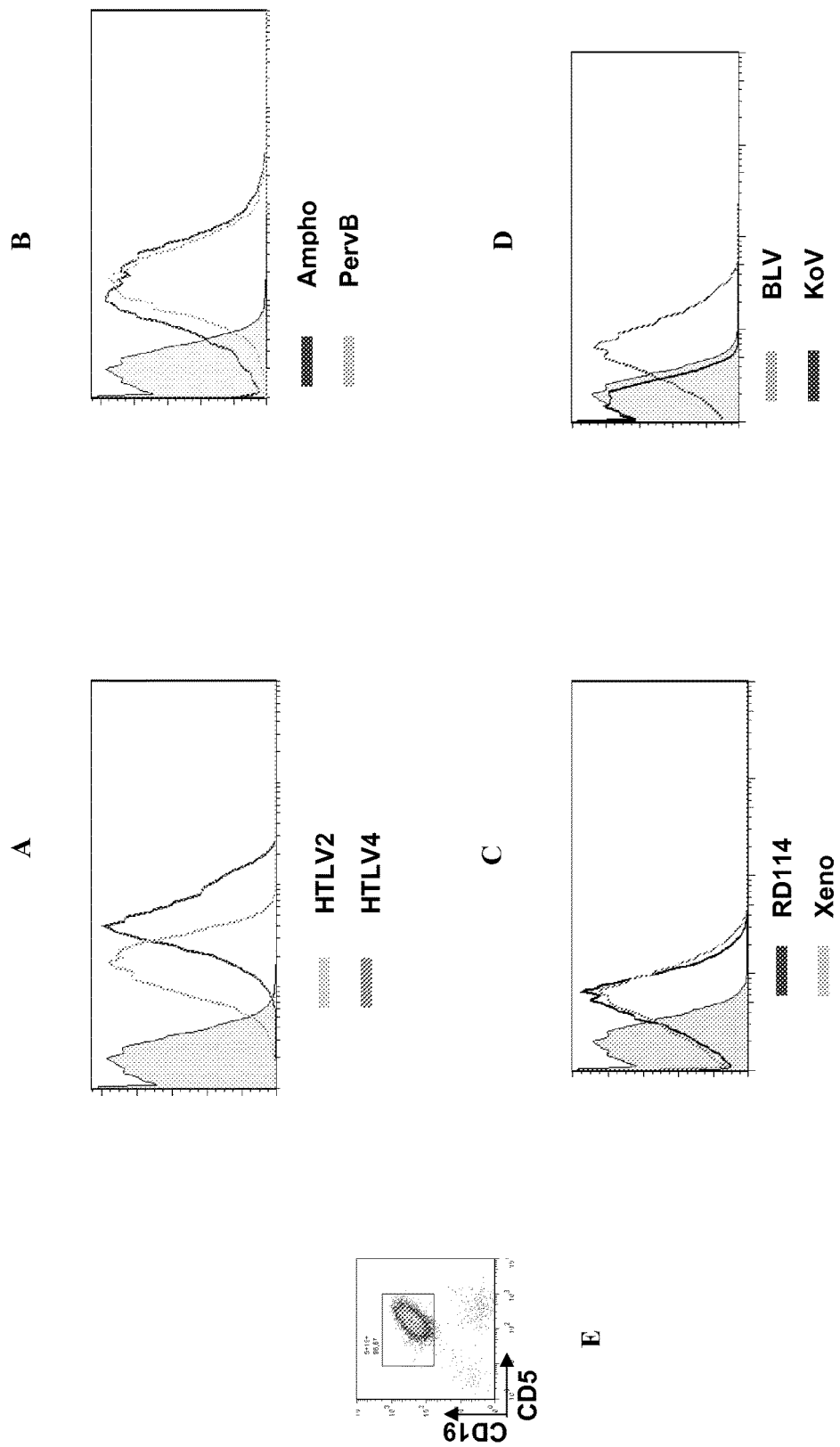
Figure 7:
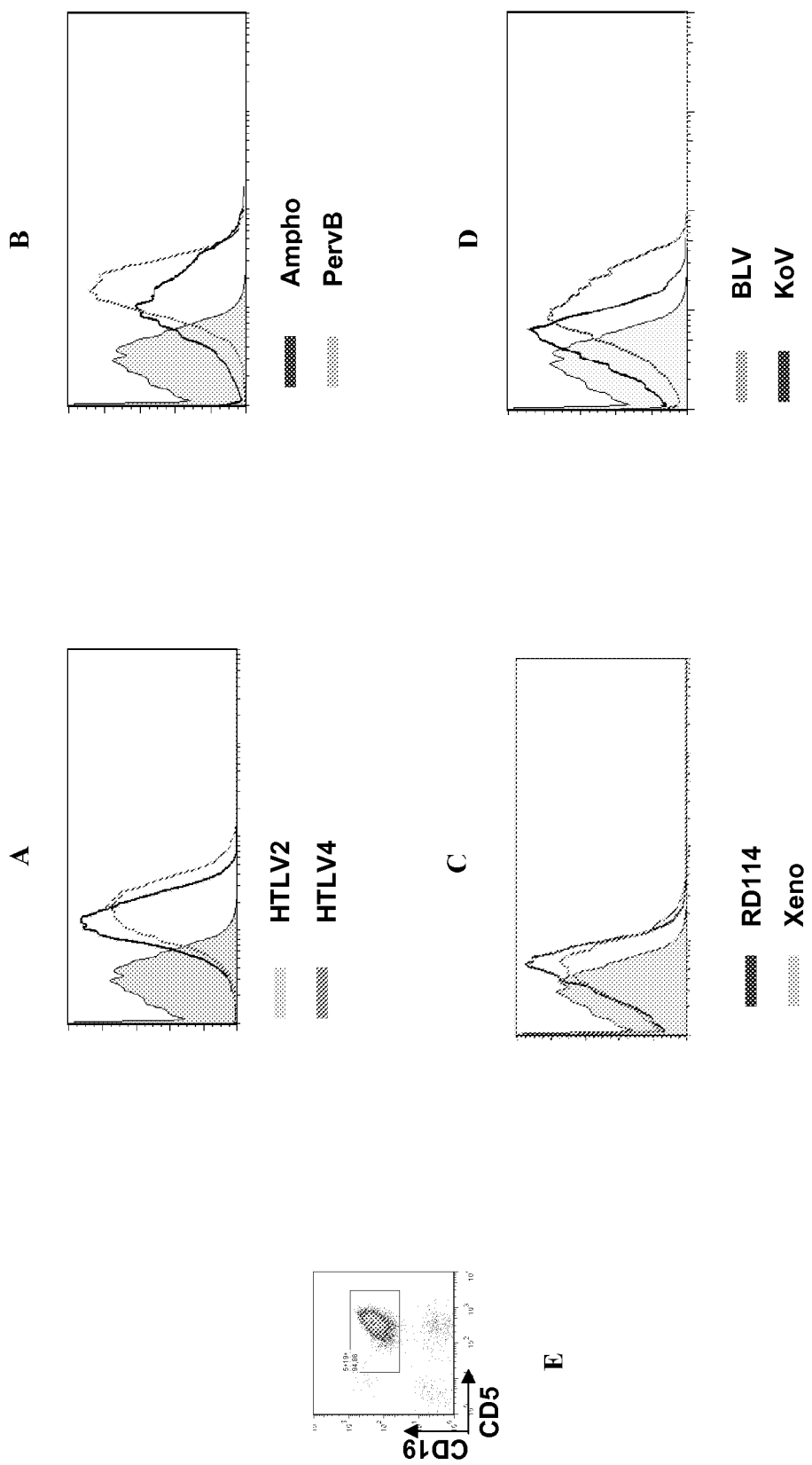
Figure 8:
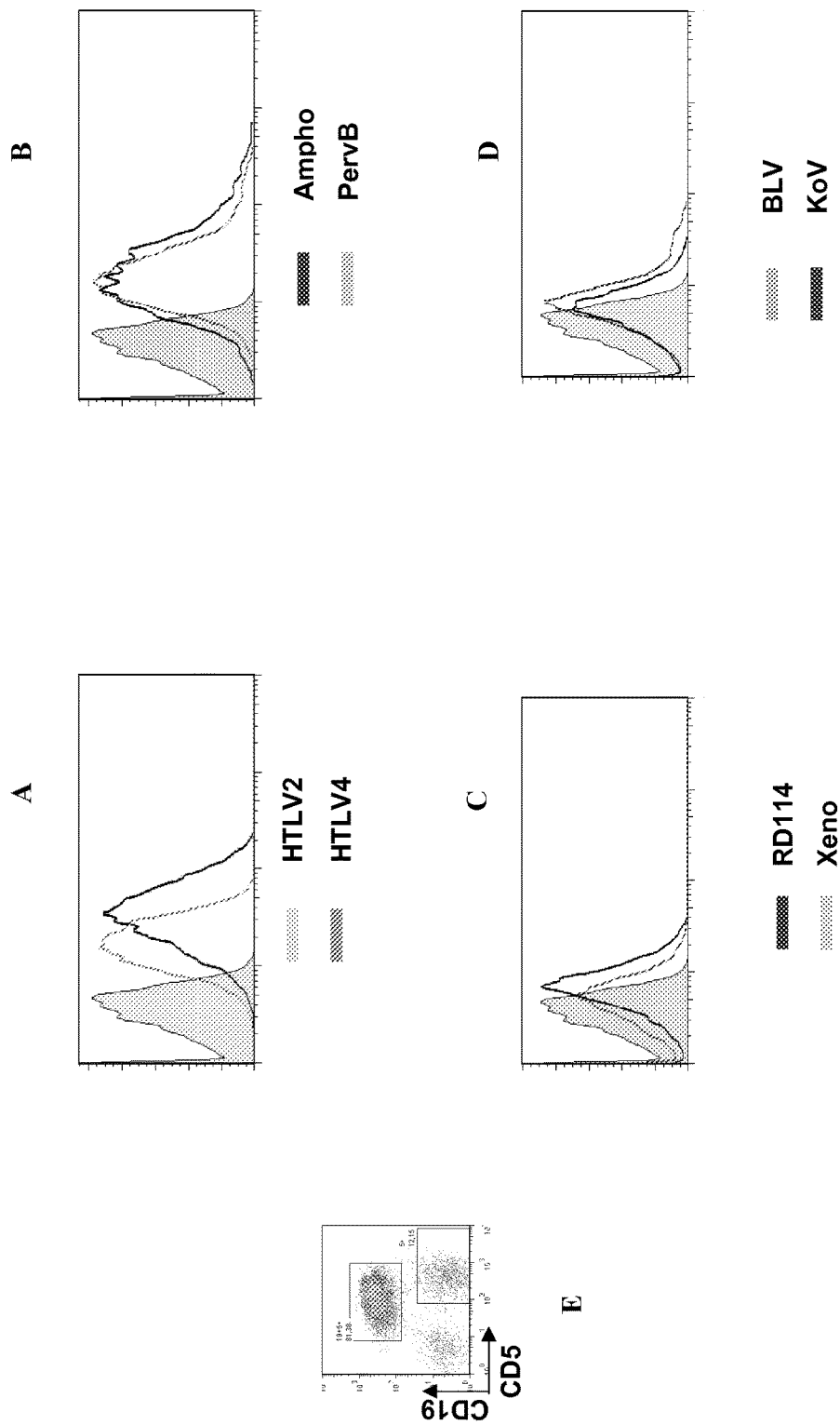
Figure 9:
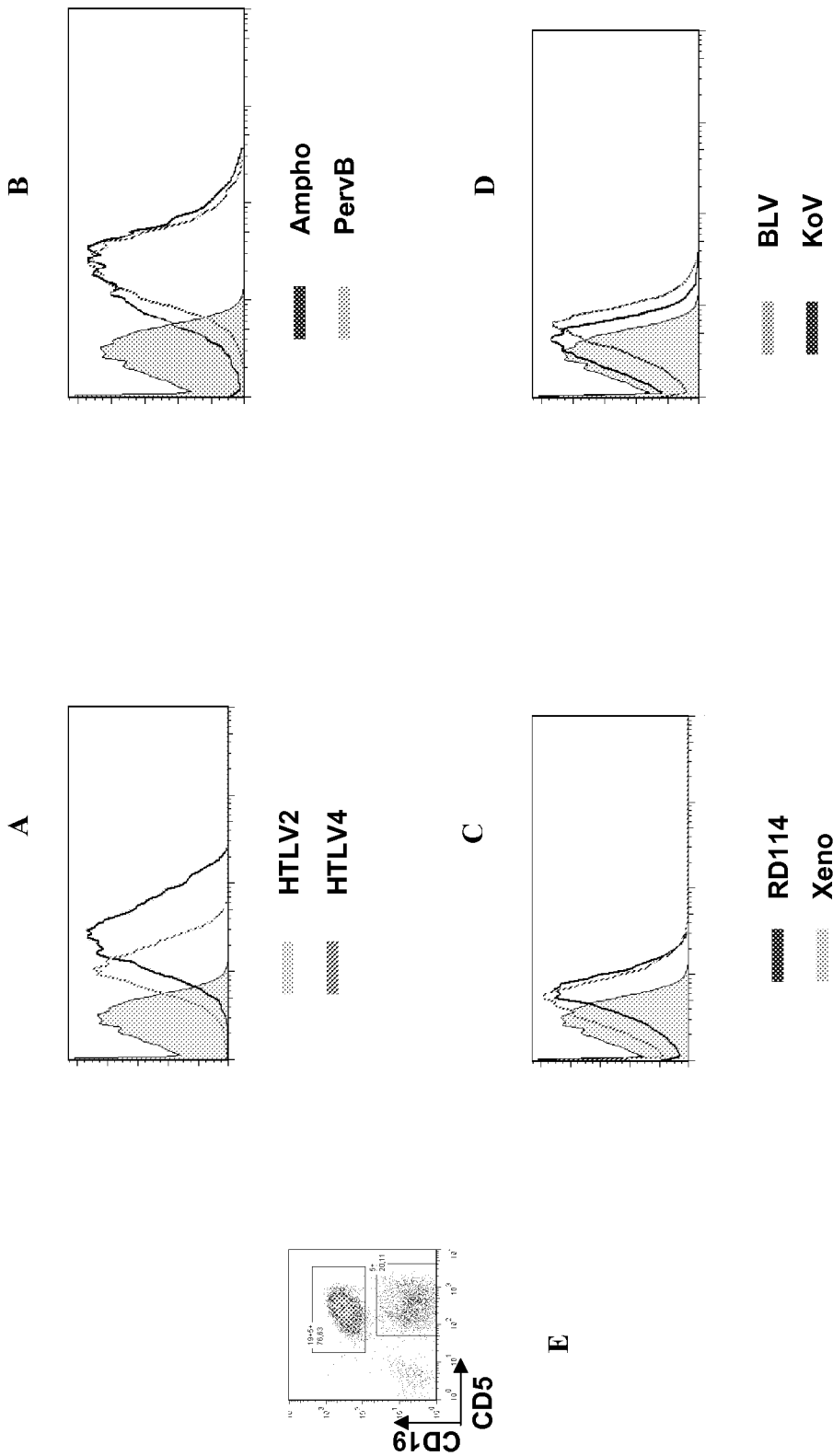

FIG. 3A to F correspond to the expression of various receptors during ex vivo differentiation of CD34+ umbilical cord blood stem cells (human) by Thrasher's protocol in the presence of Ampho, GALV, RD114 and VSV receptor binding ligands from Day=0 to Day=3, at 37° C. for 30 minutes FIGS. 3A, 3B and 3C represent the FACS obtained from a buffy coat after Ficoll and CD34+ Miltenyi selection kit (3A) and further Thrasher protocol (3B: Black: Mock, light grey: VSV, dark grey: Ampho; 3C: Black: Mock, light grey: GALV, dark grey: RD114) at Day=0)

FIGS. 3D, 3E and 3F represent represents the FACS obtained from a buffy coat after Ficoll and CD34+ Miltenyi selection kit (3D) and further Thrasher protocol (3E: Black: Mock, light grey: VSV, dark grey: Ampho; 3F: Black: Mock, light grey: GALV, dark grey: RD114) at Day=3)

FIGS. 3B,C and 3E,F shows the variation of the expression of membrane receptors of umbilical cord blood stem cells versus the time, in particular with the receptors binding ligands of Ampho (SEQ ID NO:1), GALV (SEQ ID NO:2), RD114 (SEQ ID NO:3) and VSV (SEQ ID NO:4).

FIG. 4 to FIG. 9 represent the RBD binding profile on human B and B– chronic lymphocytic leukaemia (B-CLL) cells using the following RBD:

HTLV 2 (SEQ ID NO: 28), HTLV 4 (SEQ ID NO: 31), Ampho (SEQ ID NO: 1), Perv B (SEQ ID NO: 22), BLV (SEQ ID NO: 30), RD 114 (SEQ ID NO: 3), KoV (SEQ ID NO: 20, and Xeno (SEQ ID NO: 10).

FIG. 4A to 4E represent the RBD binding profile to CD19+ cells and the FACS of a healthy donor (healthy donor 1):

FIG. 4A: curve filled with grey: mock
Light grey unfilled curve: HTLV 2 (SEQ ID NO: 28),
Dark grey unfilled curve: HTLV 4 (SEQ ID NO: 31).

FIG. 4B: curve filled with grey: mock
Light grey unfilled curve: Perv B (SEQ ID NO: 22),
Dark grey unfilled curve: Ampho (SEQ ID NO: 1).

Figure 11:
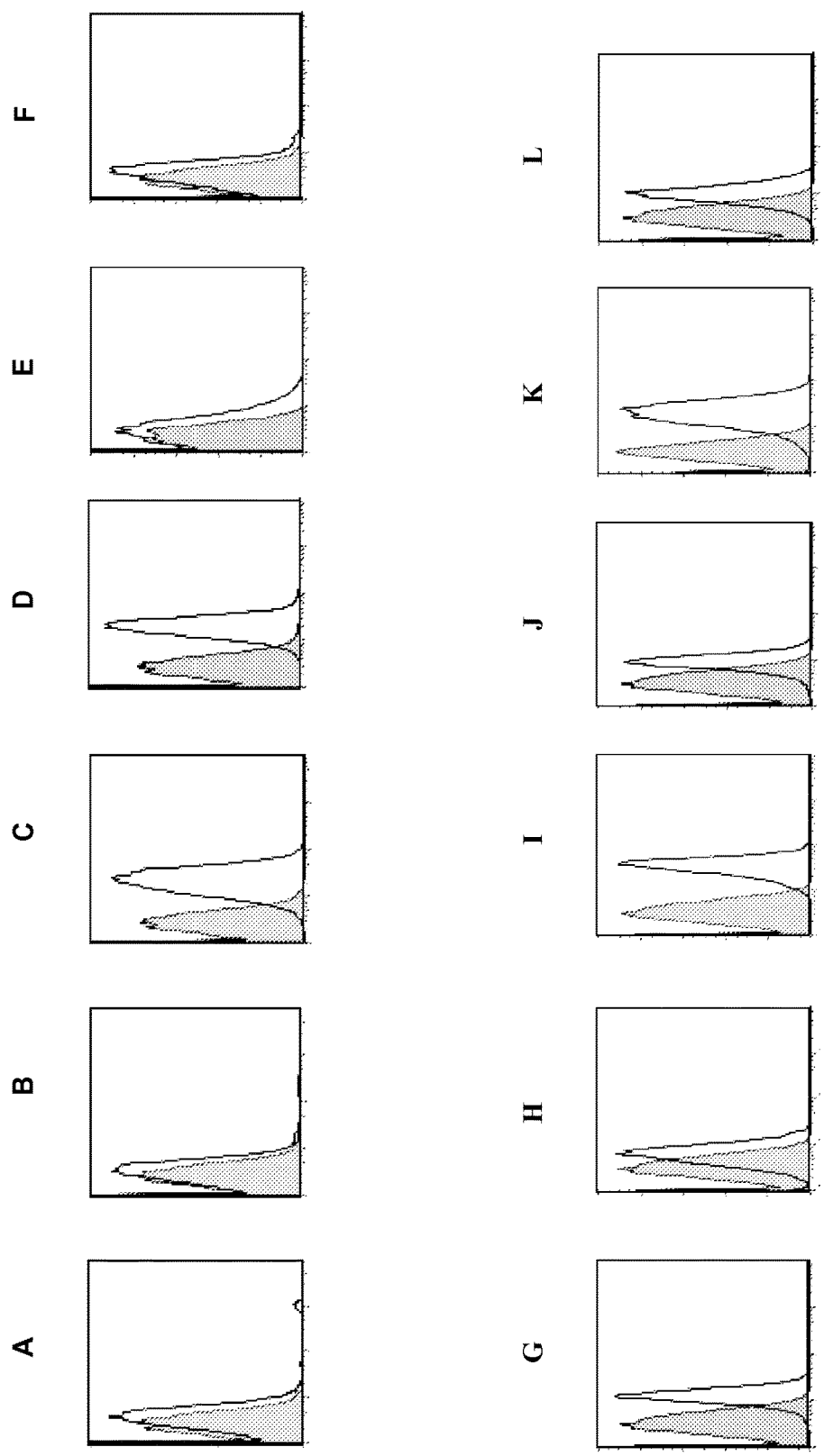
Figure 12:
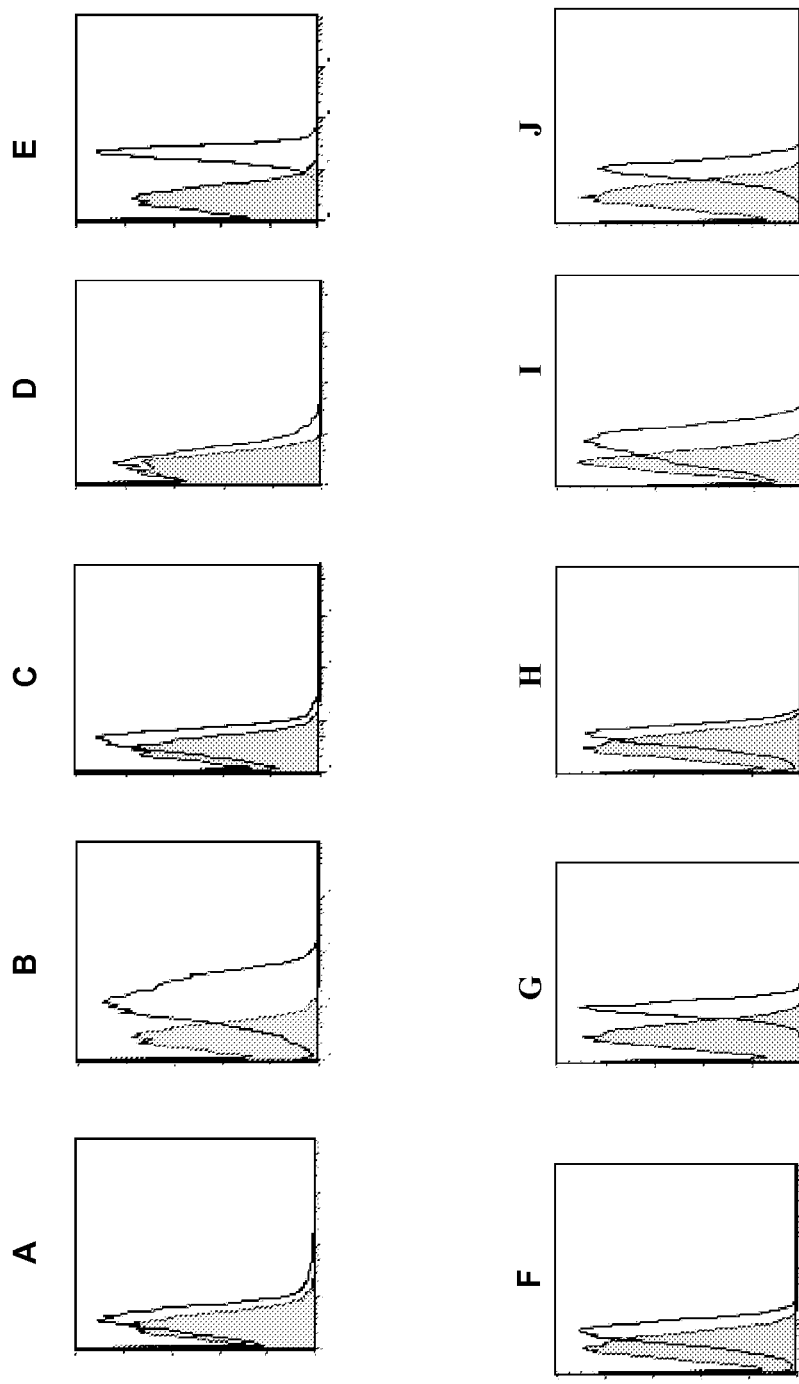

FIG. 4C: curve filled with grey: mock
Light grey unfilled curve: Xeno (SEQ ID NO: 10),
Dark grey unfilled curve: RD 114 (SEQ ID NO: 3).
FIG. 4D: curve filled with grey: mock
Light grey unfilled curve: BLV (SEQ ID NO: 30),
Dark grey unfilled curve: KoV (SEQ ID NO: 20).
FIG. 4E: FACS of B cells
FIG. 5A to 5E represent the RBD binding profile to CD19+ cells and the FACS of another healthy donor (healthy donor 2):
FIG. 5A: curve filled with grey: mock
Light grey unfilled curve: HTLV 2 (SEQ ID NO: 28),
Dark grey unfilled curve: HTLV 4 (SEQ ID NO: 31).
FIG. 5B: curve filled with grey: mock
Light grey unfilled curve: Perv B (SEQ ID NO: 22),
Dark grey unfilled curve: Ampho (SEQ ID NO: 1).
FIG. 5C: curve filled with grey: mock
Light grey unfilled curve: Xeno (SEQ ID NO: 10),
Dark grey unfilled curve: RD 114 (SEQ ID NO: 3).
FIG. 5D: curve filled with grey: mock
Light grey unfilled curve: BLV (SEQ ID NO: 30),
Dark grey unfilled curve: KoV (SEQ ID NO: 20).
FIG. 5E: FACS of B cells
FIG. 6A to 6E represent the RBD binding profile to CD19+ cells and the FACS of a patient with CLL (patient 1):
FIG. 6A: curve filled with grey: mock
Light grey unfilled curve: HTLV 2 (SEQ ID NO: 28),
Dark grey unfilled curve: HTLV 4 (SEQ ID NO: 31).
FIG. 6B: curve filled with grey: mock
Light grey unfilled curve: Perv B (SEQ ID NO: 22),
Dark grey unfilled curve: Ampho (SEQ ID NO: 1).
FIG. 6C: curve filled with grey: mock
Light grey unfilled curve: Xeno (SEQ ID NO: 10),
Dark grey unfilled curve: RD 114 (SEQ ID NO: 3).
FIG. 6D: curve filled with grey: mock
Light grey unfilled curve: BLV (SEQ ID NO: 30),
Dark grey unfilled curve: KoV (SEQ ID NO: 20).
FIG. 6E: FACS of B cells
FIG. 7A to 7E represent the RBD binding profile to CD19+ cells and the FACS of another patient with CLL (patient 2):
FIG. 7A: curve filled with grey: mock
Light grey unfilled curve: HTLV 2 (SEQ ID NO: 28),
Dark grey unfilled curve: HTLV 4 (SEQ ID NO: 31).
FIG. 7B: curve filled with grey: mock
Light grey unfilled curve: Perv B (SEQ ID NO: 22),
Dark grey unfilled curve: Ampho (SEQ ID NO: 1).
FIG. 7C: curve filled with grey: mock
Light grey unfilled curve: Xeno (SEQ ID NO: 10),
Dark grey unfilled curve: RD 114 (SEQ ID NO: 3).
FIG. 7D: curve filled with grey: mock
Light grey unfilled curve: BLV (SEQ ID NO: 30),
Dark grey unfilled curve: KoV (SEQ ID NO: 20).
FIG. 7E represents the FACS of B cells.
FIG. 8A to 8E represent the RBD binding profile to CD19+ cells and the FACS of another patient with CLL (patient 3):
FIG. 8A: curve filled with grey: mock
Light grey unfilled curve: HTLV 2 (SEQ ID NO: 28),
Dark grey unfilled curve: HTLV 4 (SEQ ID NO: 31).
FIG. 8B: curve filled with grey: mock
Light grey unfilled curve: Perv B (SEQ ID NO: 22),
Dark grey unfilled curve: Ampho (SEQ ID NO: 1).
FIG. 8C: curve filled with grey: mock
Light grey unfilled curve: Xeno (SEQ ID NO: 10),
Dark grey unfilled curve: RD 114 (SEQ ID NO: 3).
FIG. 8D: curve filled with grey: mock
Light grey unfilled curve: BLV (SEQ ID NO: 30),
Dark grey unfilled curve: KoV (SEQ ID NO: 20).
FIG. 8E: FACS of B cells.
FIGS. 9A to 9E represent the RBD binding profile to CD19+ cells and the FACS of another patient with CLL (patient 4):
FIG. 9A: curve filled with grey: mock
Light grey unfilled curve: HTLV 2 (SEQ ID NO: 28),
Dark grey unfilled curve: HTLV 4 (SEQ ID NO: 31).
FIG. 9B: curve filled with grey: mock
Light grey unfilled curve: Perv B (SEQ ID NO: 22),
Dark grey unfilled curve: Ampho (SEQ ID NO: 1).
FIG. 9C: curve filled with grey: mock
Light grey unfilled curve: Xeno (SEQ ID NO: 10),
Dark grey unfilled curve: RD 114 (SEQ ID NO: 3).
FIG. 9D: curve filled with grey: mock
Light grey unfilled curve: BLV (SEQ ID NO: 30),
Dark grey unfilled curve: KoV (SEQ ID NO: 20).
FIG. 9E: FACS of B cells.
FIG. 10A to 10K represent the RBD binding profile of various RBD on human red blood cell (RBC):
FIG. 10A: HTLV2 (SEQ ID NO: 28) tagged with a green fluorescent protein (GFP),
FIG. 10B: HTLV2 (SEQ ID NO: 28).
FIG. 10C: HTLV4 (SEQ ID NO: 31).
FIG. 10D: Ampho (SEQ ID NO: 1).
FIG. 10E: GALV (SEQ ID NO: 4).
FIG. 10F: RD114 (SEQ ID NO: 3).
FIG. 10G: BLV (SEQ ID NO: 30).
FIG. 10H: KoV (SEQ ID NO: 20.
FIG. 10I: Xeno (SEQ ID NO: 10).
FIG. 10J: FelV (SEQ ID NO: 19).
FIG. 10K: Perv B (SEQ ID NO: 22).
FIGS. 11A to 11L and 12A to 12J represent the RBD binding profile of various RBD on unstimulated or TCR-stimulated human T cells:
FIGS. 11A to 11F: unstimulated human T cells:
FIG. 11A: HTLV2 (SEQ ID NO: 28) tagged with a green fluorescent protein (GFP),
FIG. 11B: HTLV2 (SEQ ID NO: 28).
FIG. 11C: HTLV4 (SEQ ID NO: 31).
FIG. 11D: Ampho (SEQ ID NO: 1).
FIG. 11E: GALV (SEQ ID NO: 4).
FIG. 11F: RD114 (SEQ ID NO: 3).
FIGS. 11G to 11L: TCR-stimulated T cells:
FIG. 11G: HTLV2 (SEQ ID NO: 28) tagged with a green fluorescent protein (GFP),
FIG. 11H: HTLV2 (SEQ ID NO: 28).
FIG. 11I: HTLV4 (SEQ ID NO: 31).
FIG. 11J: Ampho (SEQ ID NO: 1).
FIG. 11K: GALV (SEQ ID NO: 4).
FIG. 11L: RD114 (SEQ ID NO: 3).
FIGS. 12A to 12E: Unstimulated T cells:
FIG. 12A: BLV (SEQ ID NO: 30),
FIG. 12B: KoV (SEQ ID NO: 20,
FIG. 12C: Xeno (SEQ ID NO: 10),
FIG. 12D: FelV (SEQ ID NO: 19),
FIG. 12E: Perv B (SEQ ID NO: 22).
FIGS. 12F to 12J: TCR-stimulated T cells:
FIG. 12F: BLV (SEQ ID NO: 30),
FIG. 12G: KoV (SEQ ID NO: 20,
FIG. 12H: Xeno (SEQ ID NO: 10),
FIG. 12I: FelV (SEQ ID NO: 19),
FIG. 12J: Perv B (SEQ ID NO: 22).
FIGS. 13A to 13O represent the RBD binding profile of various RBDs on murine T cells differentiated on Th0, Th1 and TH2 cells.

FIGS. 13A, 13B and 13C: Ampho (SEQ ID NO: 1).
FIGS. 13D, 13E and 13F: BLV (SEQ ID NO: 30),
FIGS. 13G, 13H, and 13I: HTLV1 (SEQ ID NO: 27).
FIGS. 13J, 13K and 13L: GALV (SEQ ID NO: 4).
FIGS. 13M, 13N and 13O: RD114 (SEQ ID NO: 3).

For each figure representing the RBD binding, the curves unfilled, from left to right, represent the mock and the RBD respectively.

FIGS. 14A to 14J represent the RBD binding profile of various RBDs on murine T cells differentiated on Th17 and iTreg cells.

FIGS. 14A and 14B: Ampho (SEQ ID NO: 1).
FIGS. 14C and 14D: BLV (SEQ ID NO: 30),
FIGS. 14E and 14F: HTLV1 (SEQ ID NO: 27).
FIGS. 14G and 14H: GALV (SEQ ID NO: 4).
FIGS. 14I and 14J: RD114 (SEQ ID NO: 3).

For each figure representing the RBD binding, the curves unfilled, from left to right, represent the mock and the RBD respectively.

FIGS. 15A to 15O represent the RBD binding profile BLV (SEQ ID NO:30) and GALV (SEQ ID NO:4) RBDs on CD34 progenitor cells at day 0, day 2, day 4 and day 6.

FIGS. 15A, 15D, 15H, 15L represent the FACS of CD34 cells.

FIGS. 15A, 15B and 15C represent day 0.
FIGS. 15D, 15E, 15F and 15G represent day 2.
FIGS. 15H, 15I, 15J and 15K represent day 4.
FIGS. 15L, 15M, 15N and 15O represent day 6.
FIGS. 15B, 15E, 15I and 15M represent the RBD binding on CD34+/CD38− cells.
FIGS. 15C, 15F, 15J and 15N represent the RBD binding on CD34+/CD38+ cells.
FIGS. 15G, 15K, 15O represent the RBD binding on CD34−/CD38+ cells.

For each figure representing the RBD binding, the curved filled with grey represents the mock and the curves unfilled, from left to right, represent GALV and BLV RBDs respectively.

FIG. 16A to 16F represent the RBD binding profile (BLV (SEQ ID NO:30), GALV (SEQ ID NO:4) and Ampho (SEQ ID NO: 1) RBDs) on CD34 progenitor cells cultured in two media.

FIGS. 16A to 16C: STEMPAN medium.
FIG. 16D to 16F: XVIVO15 medium.
FIG. 16A, 16D represent the FACS of CD 34 cells.
FIGS. 16B and 16E: CD34+/CD38− cells.
FIGS. 16C and 16E: CD34+/CD38+ cells.

For each figure representing the RBD binding, the curved filled with grey represents the mock and the curves unfilled, from left to right, represent Ampho, GALV and BLV RBDs respectively.

Figure 17:
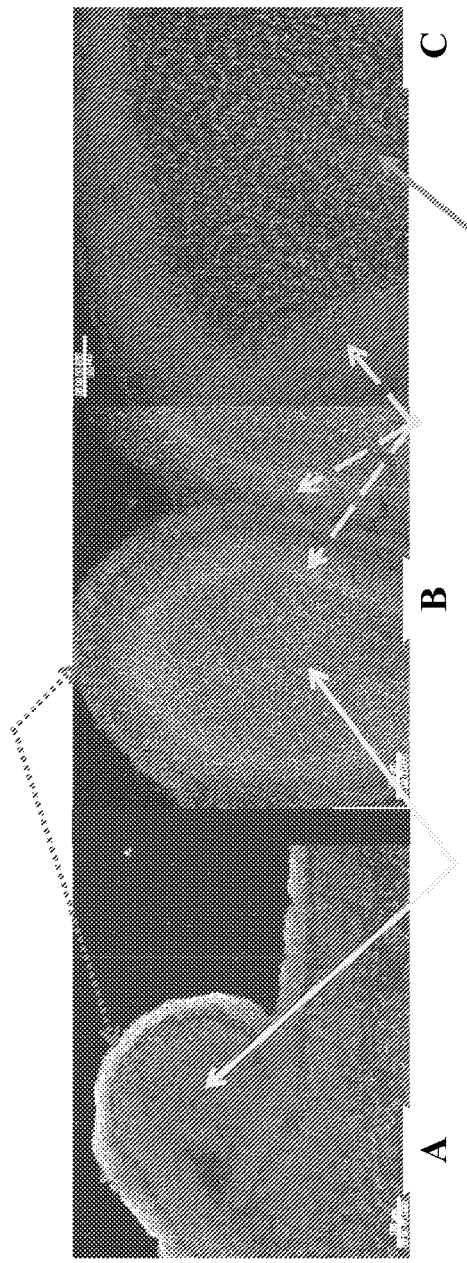

FIGS. 17A to 17C represent the morphological changes in the postnatal development of cerebral cortex from day 6 after birth to day 19 after birth.

Figure 18:
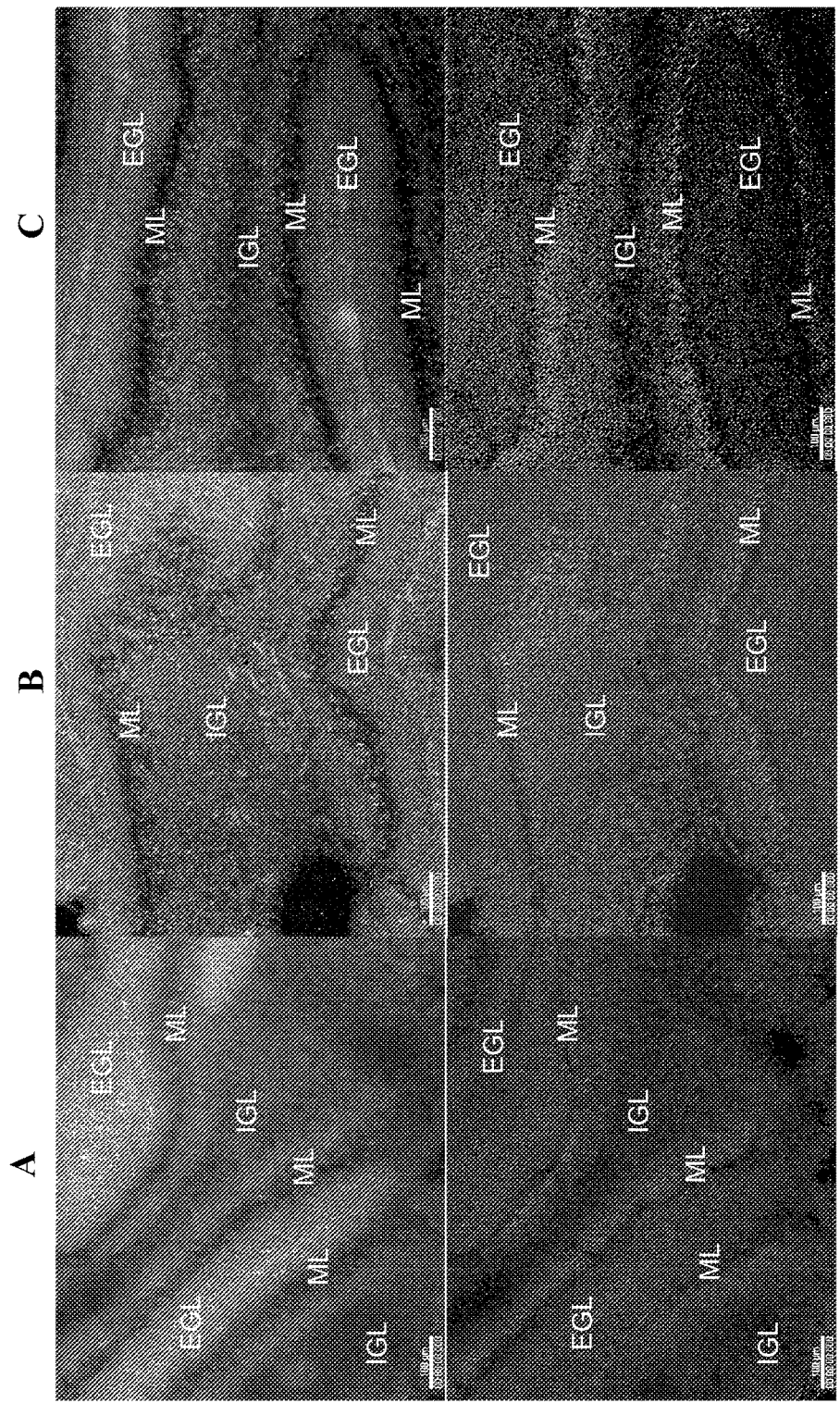

FIG. 17A: day 6 after birth.
Dashed arrow: external granular layer (EGL)
Full line arrow: internal granular layer (IGL)
FIG. 17B: day 12 after birth
Dashed arrow (small dots): external granular layer (EGL)
Full line arrow: internal granular layer (IGL)
Dashed arrow (large underscores): molecular layer (ML)
FIG. 17C: day 19 after birth
Dashed arrow (large underscores): molecular layer (ML)
Full line arrow: granular layer (GL)
FIG. 18A to 18F represent the expression of nutrient transporters in the different layers after day 6-7 (grey zones).
FIG. 18A: Hoechst+Alexa488 (Ampho/PiT2)

FIG. 18B: Hoechst+Alexa488 (GALV/PiT1)
FIG. 18C Hoechst+Alexa488 (HTLV1/GLUT1)
FIG. 18D: Hoechst+CellTrace BODIPY (Ampho/PiT2)
FIG. 18E: Hoechst+CellTrace BODIPY (GALV/PiT1)
FIG. 18F: Hoechst+CellTrace BODIPY (HTLV1/GLUT1)

The meaning of EGL, IGL and ML is the same as in FIG. 17A to 17C.

Frequencies at which the images showing these patterns of labeling with the corresponding probes are observed among all the images including both of the EGL and IGL are the following:

FIGS. 18A and 18D: 17/25 (68%)
FIGS. 18B and 18E: 19/24 (78.2%)
FIGS. 18C and 18F: 18/22 (81.8%)

Figure 19:
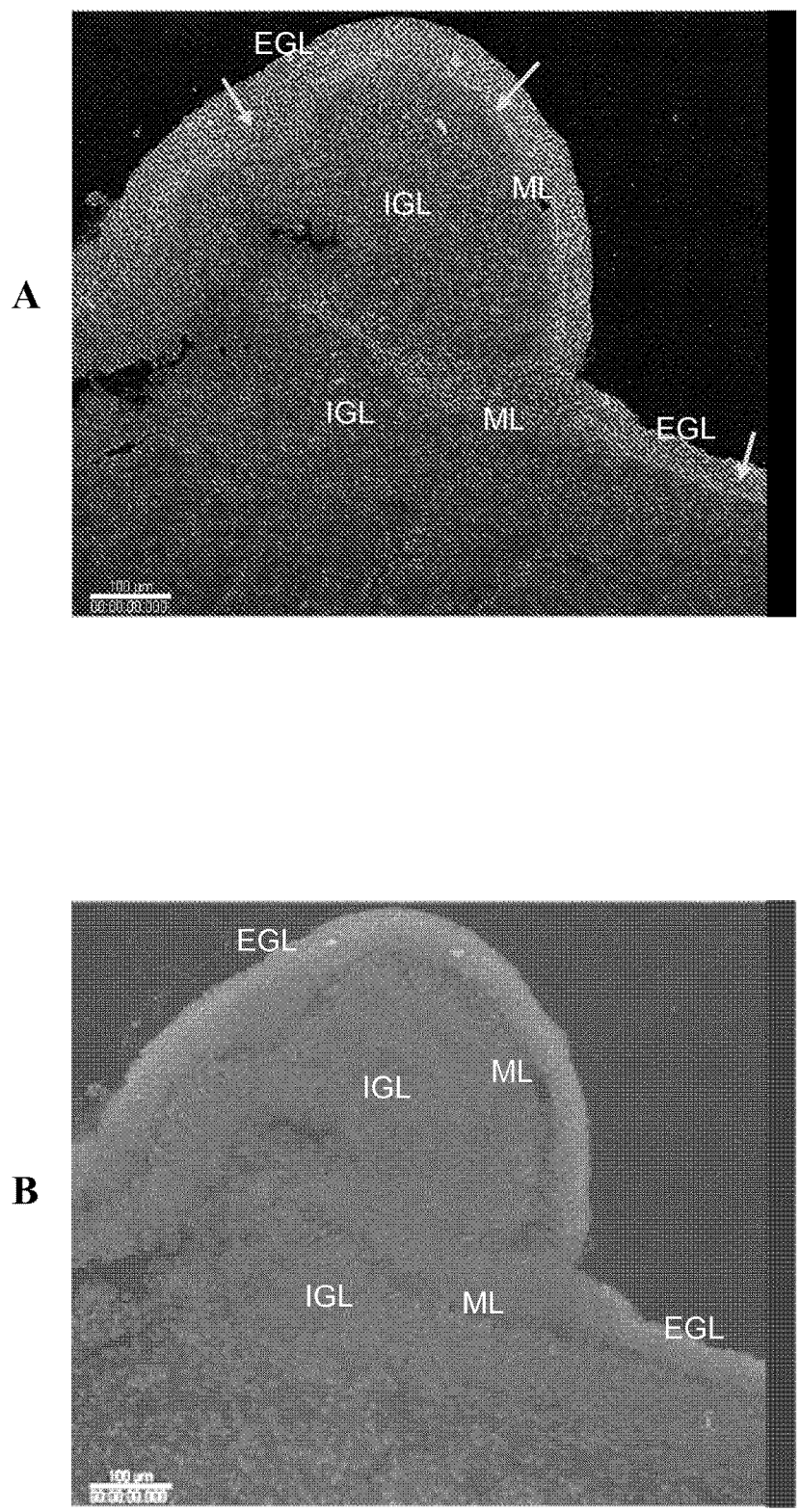

FIGS. 19A and 19B represent the expression of PiT2 in the different layers (arrows) after day 6-7.

FIG. 19A: Hoechst+Alexa488 (Ampho/PiT2)
FIG. 19B: Hoechst+CellTrace BODIPY

Frequencies at which the images with these patterns of labeling with Ampho are observed among all the images including both areas that face and do not face the forming fissures are the following: 11/19 (57.9%).

FIGS. 20A to 20D represent the expression of PiT1 in the different layers (arrows) after days 6-7 or days 12-14.

Figure 20:
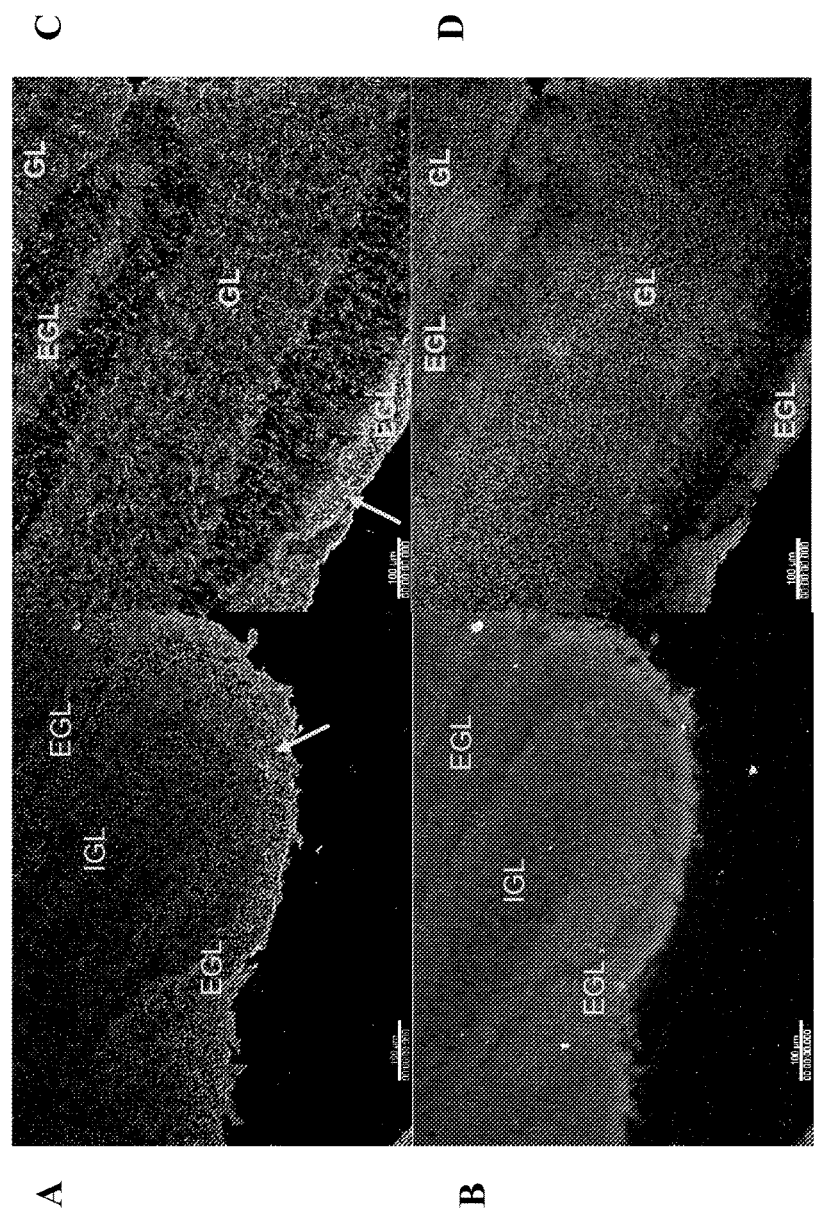

Day 6-7:
FIG. 20A: Hoechst+Alexa488 (GALV/PiT1)
FIG. 20B: Hoechst+CellTrace BODIPY
Days 12-14
FIG. 20C: Hoechst+Alexa488 (GALV/PiT1)
FIG. 20D: Hoechst+CellTrace BODIPY Frequencies at which the images with these patterns of labeling with GRBD are observed among all the images including both areas that face and do not face the forming fissures are the following:

FIGS. 20A and 20B: 3/13 (23.1%)
FIGS. 20C and 20D: 4/15 (26.7%)

FIGS. 21A to 21D represent the expression profiles of PiT1 in the cerebellar cortex of adult mice (16-22 days after birth).

Figure 21:
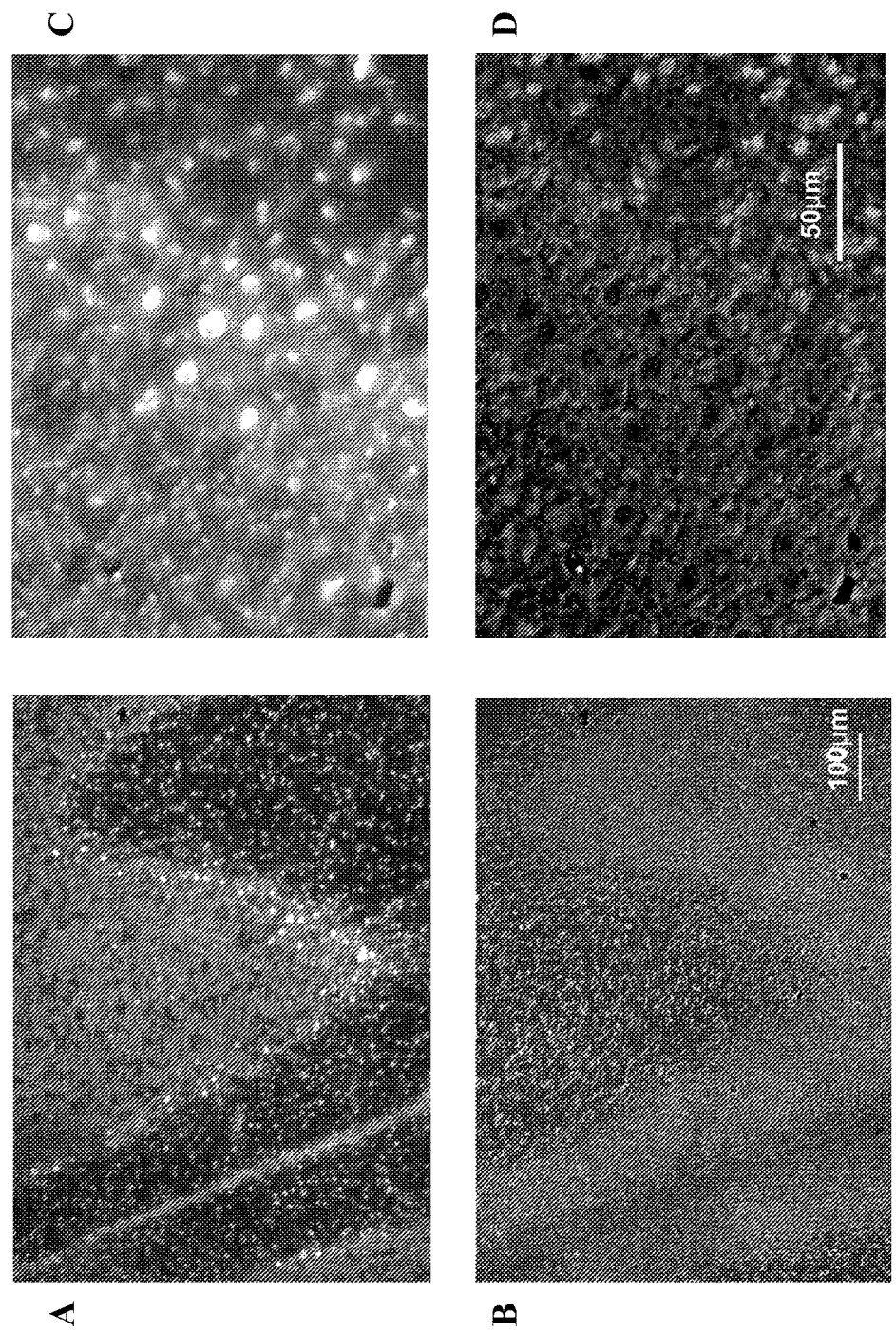

FIG. 21A: Hoechst+Alexa488 (GALV/PiT1)
FIGS. 21B and 21D: Hoechst+CellTrace BODIPY
FIG. 21C: FIGS. 21A, 21B and 21D merged FIGS. 22A to 22D represent the expression profiles of GLUT1 in the cerebellar cortex of adult mice (16-22 days after birth).

Figure 22:
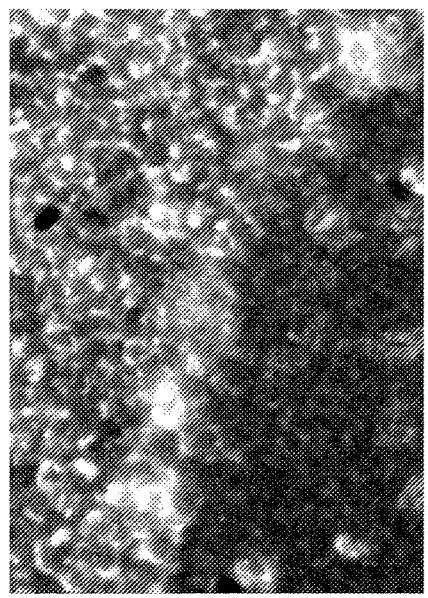
Figure 22:
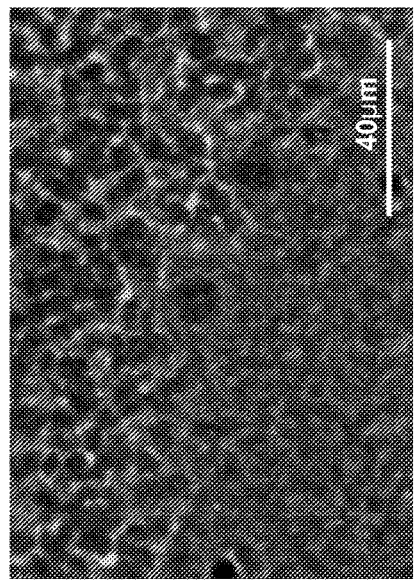
Figure 22:
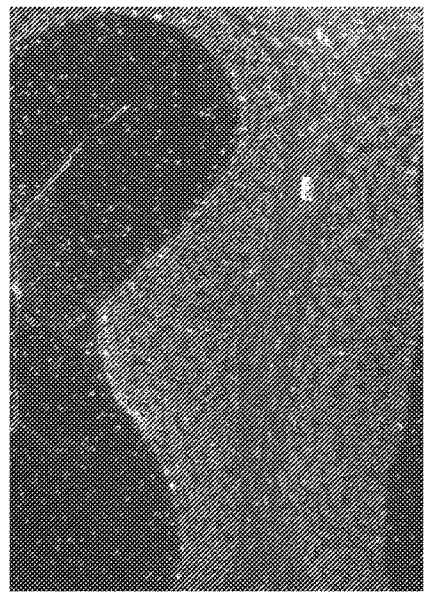
Figure 22:
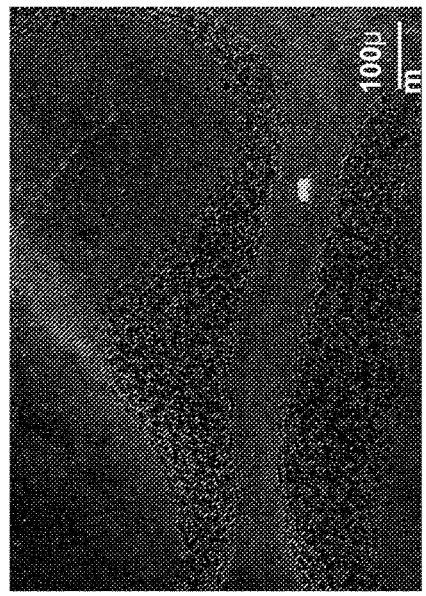

FIG. 22A: Hoechst+Alexa488 (HTLV1/GLUT1)
FIGS. 22B and 21D: Hoechst+CellTrace BODIPY
FIG. 22 C: FIGS. 22A, 22B and 22D merged

EXAMPLES

Example 1: General Method for the Production of Receptor Binding Ligands with 293T Cells Transfection At D-1: 293T Cells Spreading

| Plate type | 6 wells | 60 mm | 10 cm |
|---|---|---|---|
| Cell numbers | $3 \times 10^5$ | $10^6$ | $2 \times 10^6$ |

At D0: Transfection by Calcium Phosphate Precipitation

| Plate type | 6 wells | 60 mm | 10 cm |
|---|---|---|---|
| Volume (ml) | 3 ml | 5 ml | 10 ml |

1) Prepare the HBS+DNA of a receptor binding protein in an eppendorf tube (under hood):

| Plate type | 6 wells | 60 mm | 10 cm |
|---|---|---|---|
| DNA total quantity (µg) | 6 | 10 | 20 |
| PCSI | 6 | 10 | 20 |
| Vol. HBS (µl) | 150 | 250 | 500 |

2) Add CaCl2 2M (sterile) up to a final concentration=125 mM:

| Plate type | 6 wells | 60 mm | 10 cm |
|---|---|---|---|
| Vol. CaCl2 2M (µl) | 10 | 17 | 33 |

3) "Gently" Vortex for 10 sec,
4) Incubate 5 min at RT, a white precipitate is formed,
5) Gently add the precipitate on cells and homogenise,
6) Put the cells inside the incubator (37° C., 5% CO2).
At D1: Medium change:
The sooner the possible in the morning and gently (293T cells detach easily) with 10 ml of optipro SFM Medium (Gibco) without FBS-16H MAX,
Then incubate (32° C., 5% CO2).
After 48 h, i.e. at D3: Supernatant recovering and concentration
Recover the conditioned medium in 50 ml falcon tube
Spin at 1500 tr/min, 3 min, 4° C.
Filter the supernatant on 0.45 µm
Conserve the supernatant on ice
Add 20 ml of ultrapure water in the concentrators (Icon concentrator, 20 ml/9 k, PIERCE)
Spin at 3600 tr/min, 10 mM, (Swinging-bucket), 4° C.
Add 20 ml of filtered RBD sample
Spin at 3600 tr/min, 20 min, 4° C.
Add sample, centrifuge 20 min (100 ml max of RBD for each concentrator)
Spin until desired concentration factor is achieved (100×)
Recover concentrated sample, aliquot and stock at −80° C.

Example 2: General Method of FACS

The FACS assay of HRBD-EGFP (non antibody Glut1-ligand) is representative of the method for the receptors binding ligands:
Target cells: Any mammalian cell lines/human RBC/Human activated PBLs or any subpopulation/any primary or established cell type of interest.
For the binding assay: Entire binding assay should be performed on ice except for the actual binding step performed at 37° C.
RBD stored at −80° C.
Thaw RBD-containing conditioned medium and mock transfected conditioned medium. Avoid re-freezing the RBD preparation.

Single Assay in Eppendorf Tubes
  $1\text{-}2\times10^5$ cells per assay in 1.5 ml eppendorf tube
  Centrifuge 3 min at 3200 RPM.
  Aspirate supernatant gently.
  Gently resuspend pellet (tapping).
  Dilute the concentrated HRBD-EGFP 1/20 (v/v) dilution in PBS or medium
  Add 100 µl to 200 µl/tube of the dilution and resuspend gently.
  Incubate 30 min at 37° C. (no agitation is required).
  Keep cold during all the following steps
  Centrifuge 3 min at 3200 RPM 4° C., gently aspirate supernatant and gently tap pellet.
  Add 1 ml of cold PBA (PBS+2% FBS and 0.01% sodium azide) and gently tap pellet.
  Repeat last two steps, resuspend pellet with 500 µl of PBA and transfer to FACS tubes.
  FACS analysis
Multiple assays in 96 well-microplates (V bottom)
  $1\text{-}2\times10^5$ cells for each binding assay per well.
  Centrifuge 3 min at 1500 RPM.
  Discard the supernatant by quickly flipping the plate (over sink for instance).
  Place the plate upside down on absorbing paper to eliminate remaining droplets.
  Gently vortex the plate.
  Dilute the concentrated HRBD-EGFP preparation 1/20 (v/v) in PBS or medium
  Add 50 µl/well of the diluted preparation of HRBD-EGFP and resuspend gently.
  Incubate 30 min at 37° C. (no agitation is required).
  Transfer to 4° C. for all the following steps.
  Centrifuge 3 min at 1500 RPM at 4° C. and discard supernatant as previously.
  Wash pellet with 200 µl of cold PBA twice, with 3 min centrifuge at 1500 RPM.
  Resuspend pellet with 200 µl of PBA and transfer the mix to FACS tubes.
  FACS analysis
FIGS. 3B,C and 3E,F present the results obtained with the receptors binding ligands of SEQ ID NO:1 to SEQ ID NO:4.

Example 3: Expression of Nutrient Transporters on B-CLL Cells

As compared to healthy donors with CD19+/CD5− B cells, patients with B-CLL harbor blasts with a CD19+/CD5+ phenotype. Assessment of cell surface nutrient transporters, as assessed by binding to tagged retroviral envelope receptor domains (Env RBDs), shows increased expression of the receptors for bovine leukemia virus (BLV), Xeno and RD114 (ASCT2) Env in some patients.
It is also notable that binding of HTLV RBD to the HTLV Env receptor, the ubiquitous glucose transporter Glut1, is significantly decreased in all tested B-CLL patients as compared to healthy controls (Cf. FIGS. 4 to 9).
Thus, the panel of Env RBDs will allow us to determine the signature of nutrient transporters that is associated with good and poor prognostic B-CLL.

Example 4: Expression of Nutrient Transporters on Human RBCs and Human T Cells

Figure 10:
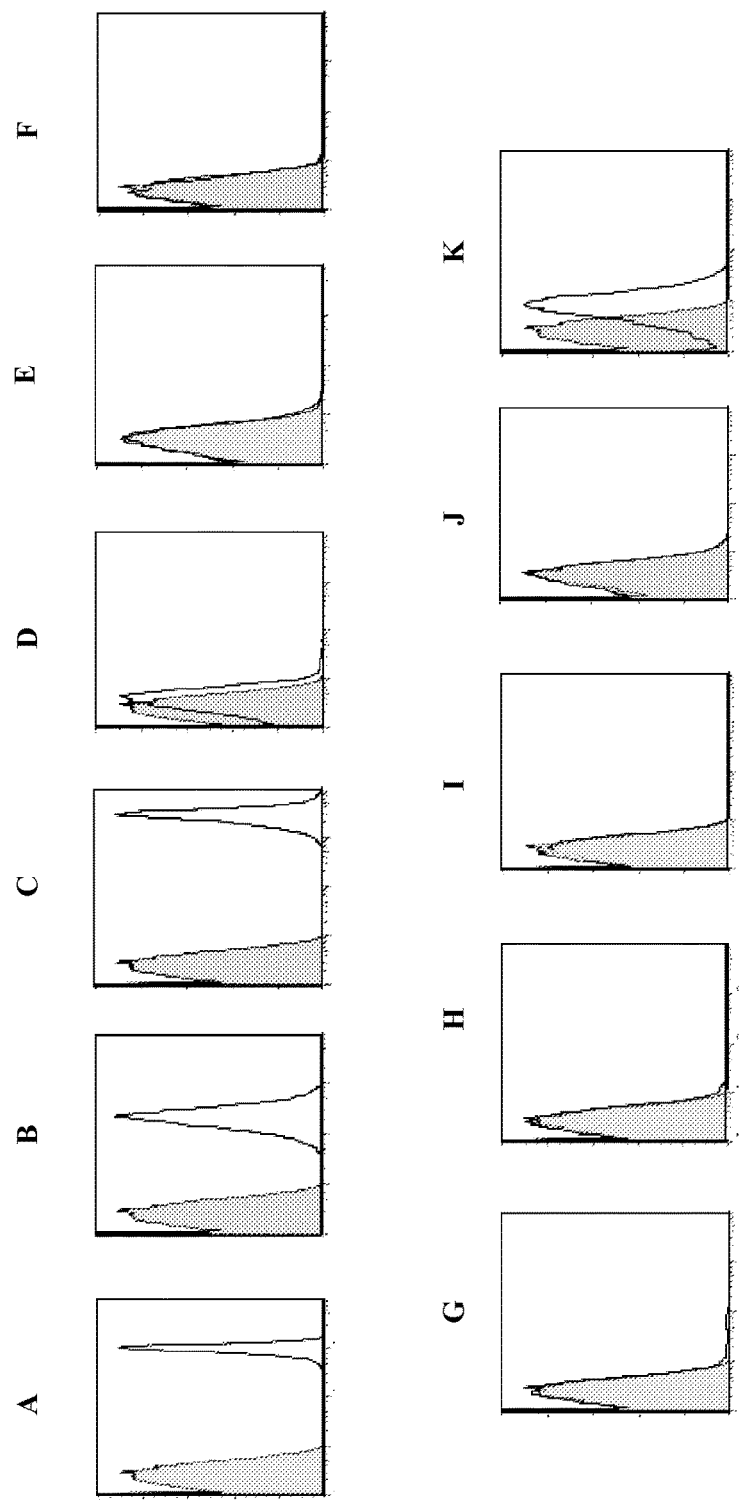

Extensive assessment of nutrient transporters on human RBC, using tagged retroviral Env RBDs, shows expression only of the HTLV and PervB Env receptors; the former identified as Glut1 whereas the latter has not yet been identified (FIG. 10).

Prior to activation, quiescent human T cells express only low levels of nutrient transporters serving as receptors for the HTLV2, GaLV, RD114, BLV, Xeno and FeLV envelopes. Receptors for all these envelopes, with the exception of Xeno, are upregulated following TCR stimulation. Interestingly, expression of the receptors binding the amphotropic and Koala RBDs (phosphate transporters) are highly expressed in quiescent cells and their levels decrease following TCR engagement (observed in some but not all experiments that we performed). Expression of the PervB receptor is not altered by TCR stimulation (FIGS. 12E and 12J).

Example 5: Use of Nutrient Transporter Expression to Track T Cell Activation and Polarization METHOD: Ligand binding on murine CD4+T cells upon Th1, 2, 17 or iTreg differentiation.

Th1 and Th17 cells are CD4+ T cell subsets characterized by the secretion of IFNg and IL-17 respectively and are involved in inflammatory processes: these subsets have been involved in many disorders such as autoimmune diseases (MS, arthritis . . . ), TB infection, skin lesions.

Th2 cells secrete IL-4, IL-5, IL-9, IL-10 . . . . These cells play a role in parasitic infections for example but are also implicated in allergy or asthma.

iTreg cells are a population of regulatory T cells, implicated in immune suppression.

This experiment was performed on murine naive CD4+T cells activated by anti-CD3/anti-CD28 and upon differentiation Th0: no polarizing cytokine added
Th1: IL-12 and anti-IL-4
Th2: IL-4 and anti-IFNg
Th17: IL-6 and TGFb
iTreg: TGFb Polarizing cytokines were added at day 0, after 2 days in culture, cells were diluted and IL-2 was added to the medium (except for Th17: IL-23 was used instead of IL-2) At day 4, binding assay was performed.

Figure 13:
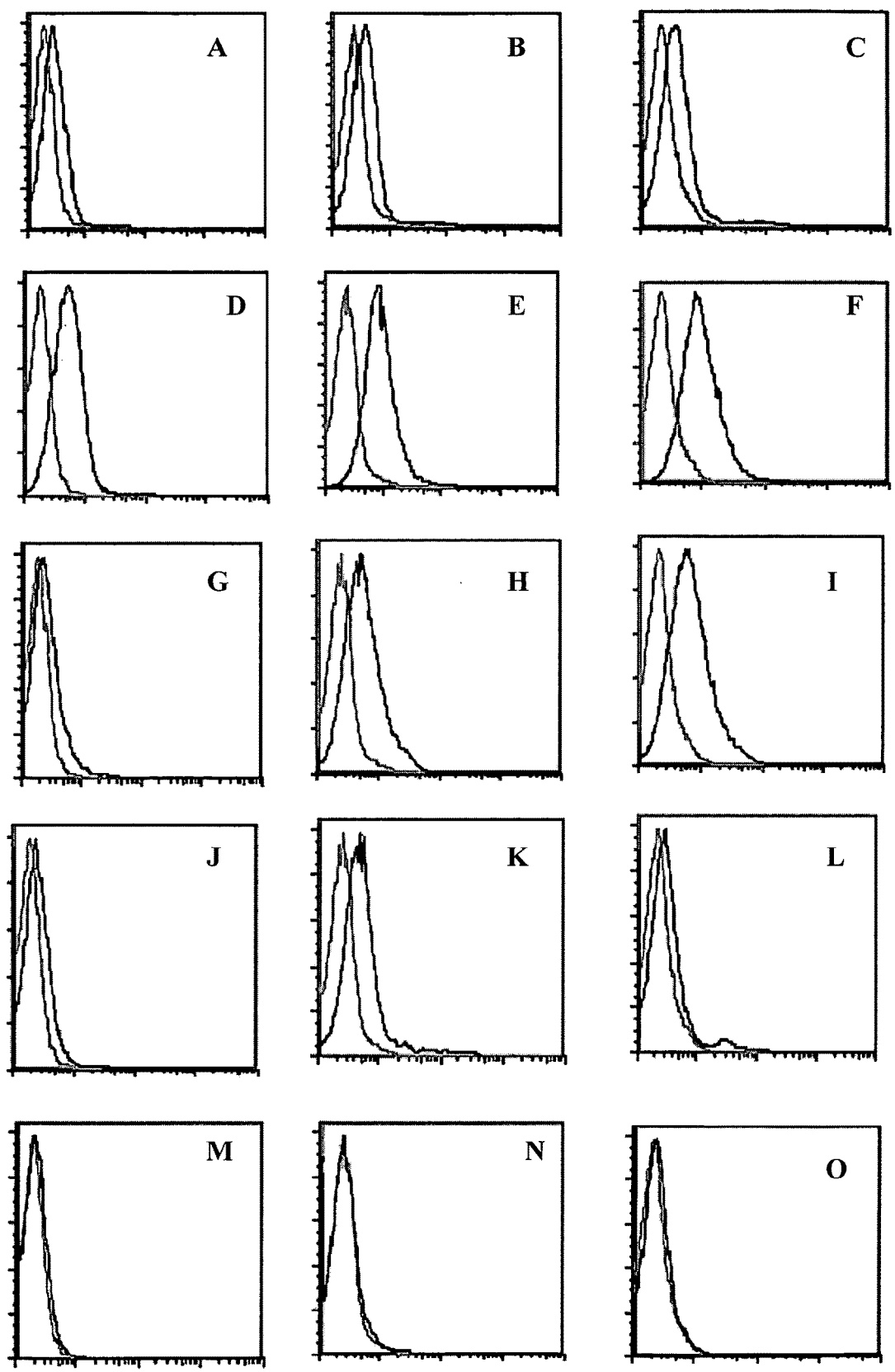
Figure 14:
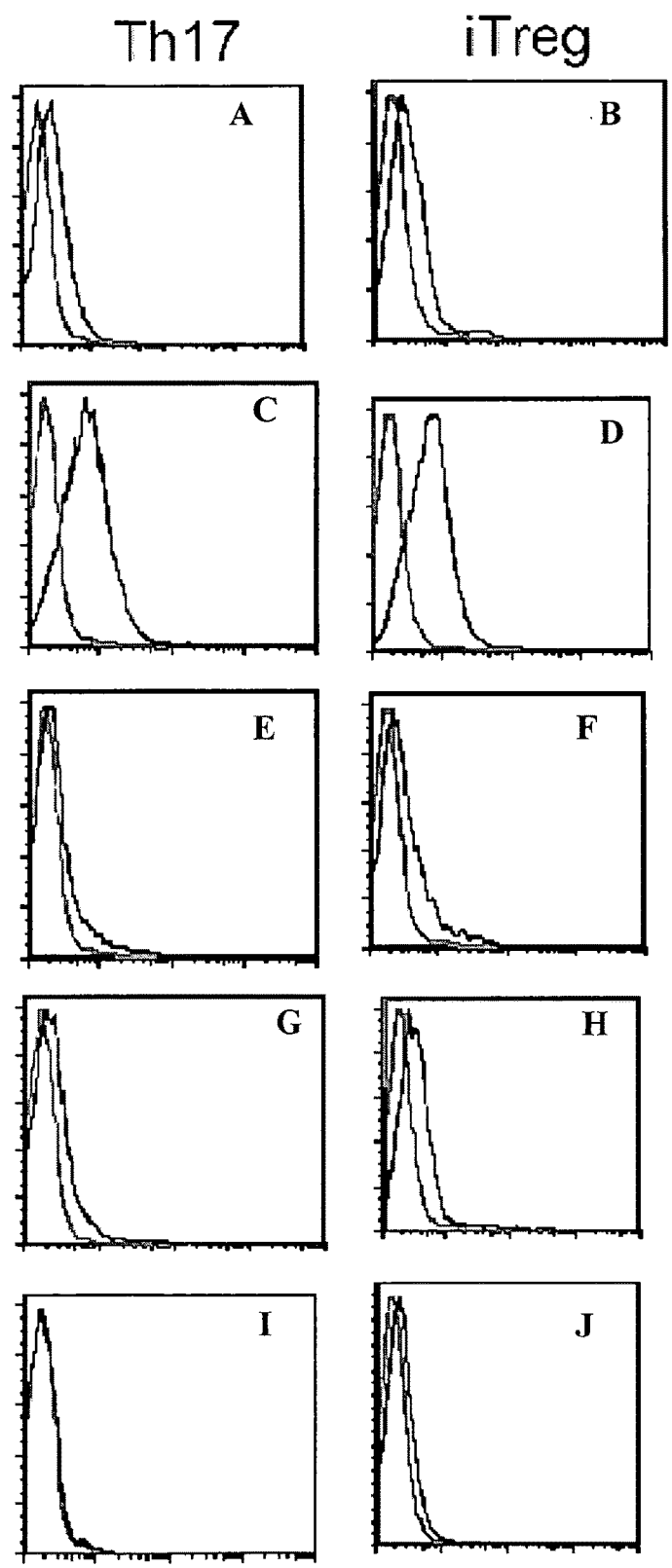

Results:

Upon stimulation of murine T cells under either non-polarizing (Th0) or polarizing conditions (towards Th1, Th2, Th17 or Treg fates), nutrient transporter expression was assessed. Of note, expression of Glut1, the receptor for the HTLV RBD, is significantly higher in Th1 and Th2 conditions than in either Th17 or Treg conditions. Moreover, the PiT1 phosphate transporter, as recognized by GaLV RBD, is expressed in T cells modulated towards a Th1 fate but is minimal under all other conditions (FIGS. 13 and 14).

Figure 15:
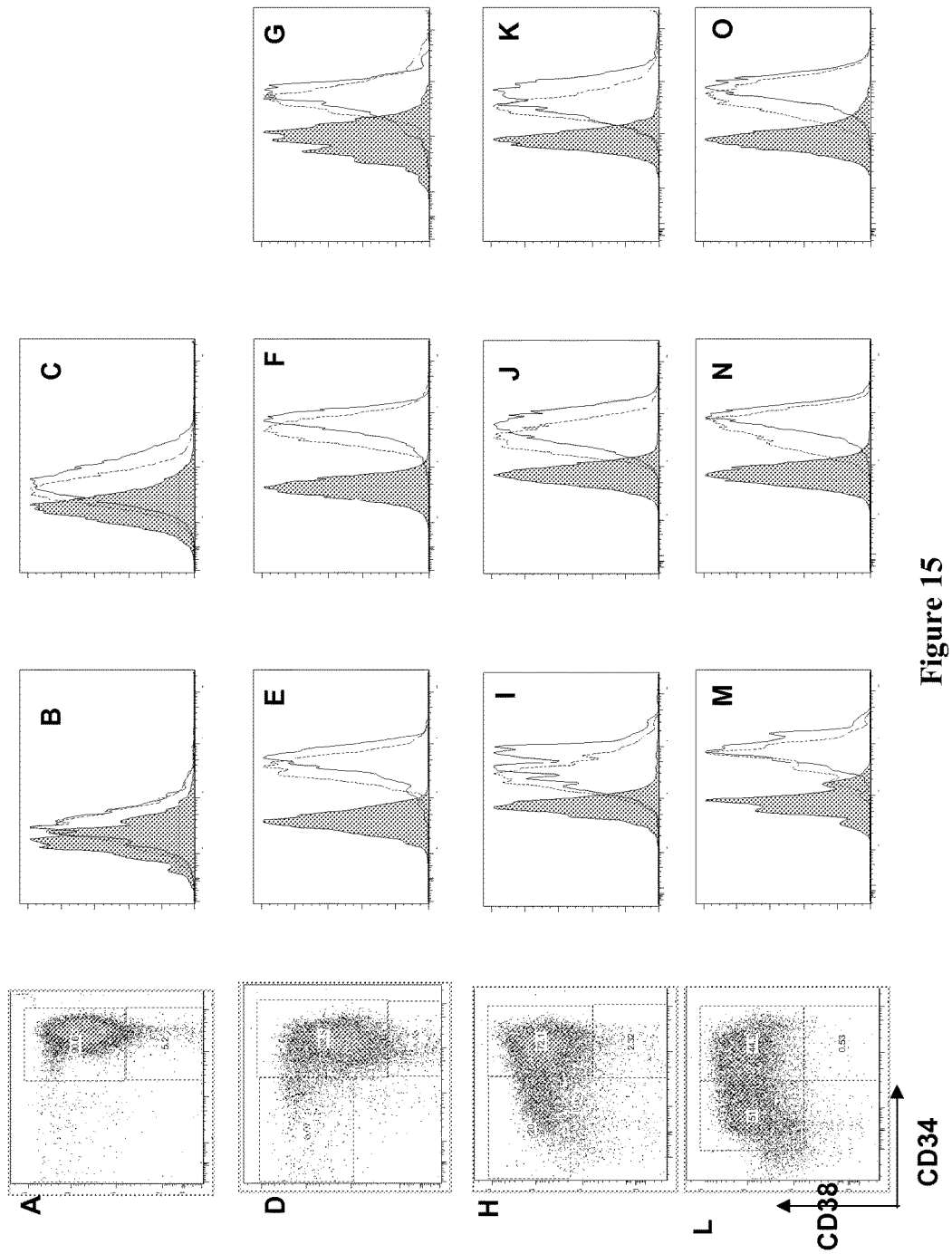

Example 6: Use of Nutrient Transporter Expression to Follow CD34 Progenitor Cell Activation and Differentiation Receptors for both BLV and GaLV RBDs were found to be expressed at significantly lower levels on primitive CD34+/CD38− progenitors as compared to more differentiated CD34+/CD38+ cells. Of note, ex vivo expansion (media/cytokines as used in the clinic) of these progenitors resulted in a significant upregulation of BLV and GaLV Env receptors, as early as 48 h post-stimulation and this upregulation was detected in primitive (CD34+/CD38−) as well as more differentiated subsets (CD34+ and CD34−) (FIG. 15).

Figure 16:
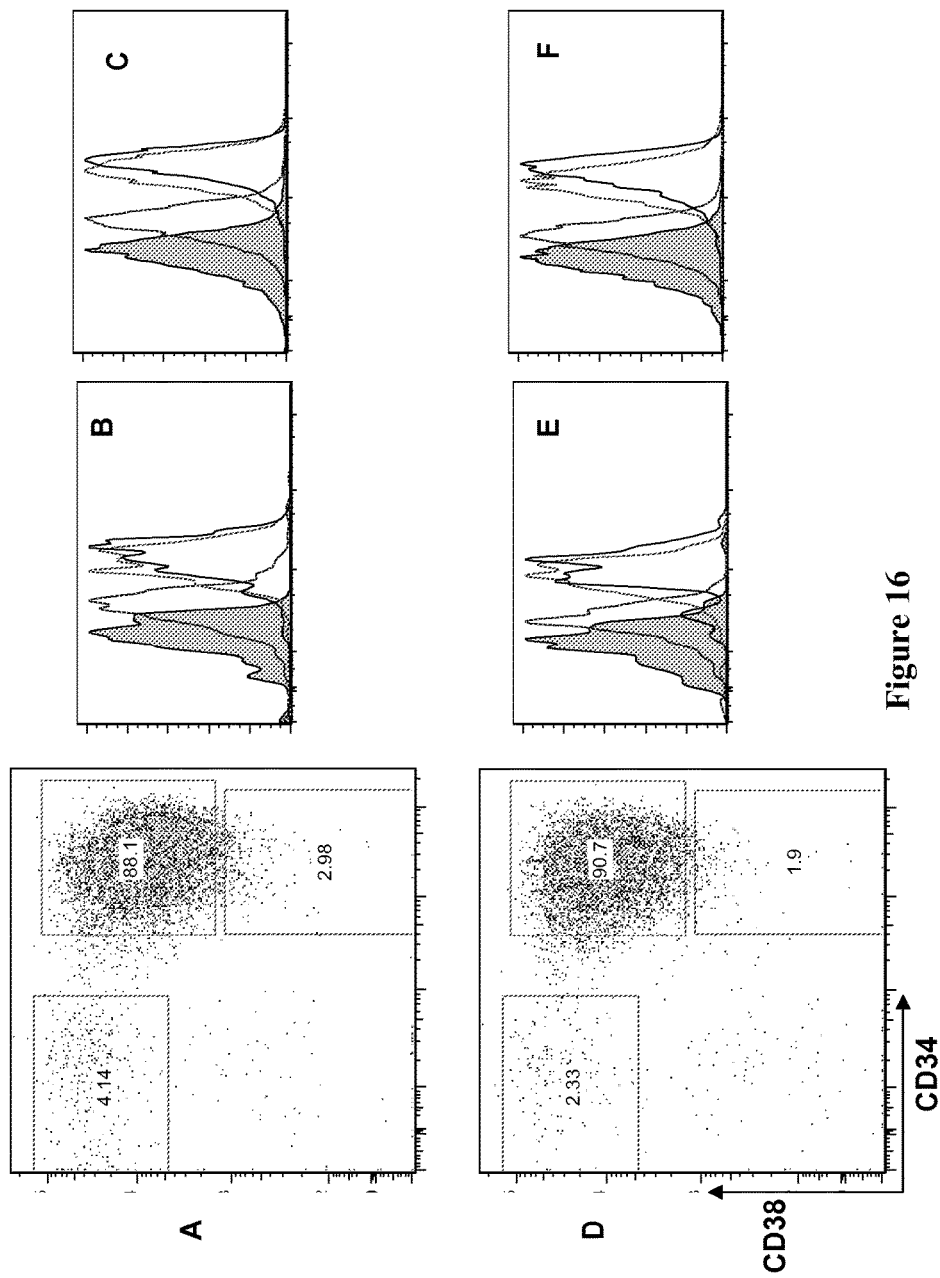

Finally, while both Stemspan and XVivo15 media are used for clinical use, expression of the PiT2 phosphate transporter, as assessed using the tagged ampho RBD, is higher in CD34+ cells (and particularly CD34+/CD38−) cultured in the former conditions. The significance of this change remains to be determined (FIG. 16).

Example 7: Distinct Expression of the Glucose (GLUT1) and Inorganic Phosphate (PiT1, PiT2) Transporters in the Developing Mouse Cerebellar Cortex Unveiled by New Ligands Based on Retrovirus Envelope Proteins HTLV 2 (SEQ ID NO: 28) for GLUT1, GALV (SEQ ID NO: 2) for PiT1, Ampho (SEQ ID NO: 1) for PiT2

All the mammalian cells uptake necessary nutrients such as glucose, amino acids, inorganic phosphate . . . via "Nutrient Transporters" on the cell surface leading to the survival of the cell (inhibition of apoptosis, inhibition of autophag, proliferation . . . ).

Using the novel probes based on the envelope proteins of retroviruses GALV (SEQ ID NO: 2), HTLV 2 (SEQ ID NO:28) and Ampho (SEQ ID NO: 1), the changes of expression profiles of some nutrient transporters during the postnatal development of cerebellar cortex of mice were deciphered.

It must be noted that HTLV 1 (SEQ ID NO: 27) or HTLV 4 (SEQ ID NO: 31) could have been used instead of HTLV 2 as said RBDs are also GLUT1 ligands.

Methods:
a) Unfixed cerebellum from 6-7, 12-14 and 16-22 day old mice,
b) Cryosectioning at 20 μm thickness,
c) Fixation with 100% ethanol at room temperature,
d) Blocking with normal serum and an endogenous biotin blocking reagent,
e) Incubation with either of the soluble RBD-rFc fusion protein, 30 min. at 37° C.: HTLV-RBD (HRBD, SEQ ID NO:27) or SEQ ID NO: 28), ligand for GLUT1; Gibbon ape Leukemia Virus-RBD (GRBD, (SEQ ID NO: 2), ligand for PiT1 Amphotropic MLV-SU (ASU, (SEQ ID NO: 1), ligand for PiT2,
f) Incubation with biotinylated anti-rabbit IgG 1 hr at room temperature,
g) Incubation with Streptavidin-Alexa488 (transporter ligand),
h) Counterstaining with Hoechst (cell nucleus) and Cell-Trace BODIPY (intracellular membranes),
i) Z-series image acquisition of the three emissions at 3 μm distance (7 slices),
j) Image restoration using Huygens professional software (Montpellier RIO Imaging),
k) Creating the final images by the Maximum Intensity Projection method using Imaris 5.7.0.

Results:
RESULTS 1: Characteristic expression profiles of GLUT1, PiT1 and PiT2 during the postnatal development of cerebellar cortex of mice The postnatal development of cerebellar cortex is accompanied by drastic morphological changes (FIGS. 17A, 17B and 17C.).

At the 6-7 days after birth, all the three nutrient transporters were shown to be expressed in larger amount in the EGL than in the IGL nearby. This is not obvious at the 12-14 days after birth (FIGS. 18A to 18F).

At the 6-7 days after birth, in the EGL that do not face the forming fissures, PiT2 was revealed to be expressed in larger amount in the deeper layer of the EGL. In this deeper area of the EGL, it is well known that postmitotic granule cells are migrating toward the ML and IGL, changing their morphologies at this stage of postnatal development (FIGS. 19A and 19B). This is observed less frequently in the cases of the other two transporters.

At the 6-7 and 12-14 days after birth, PiT1 were revealed to be preferentially localized in the areas that do not face the forming fissures (FIGS. 20A to 20D). This is not the case with the expression of PiT2 and GLUT1.

RESULTS 2: Characteristic expression profiles of GLUT1, PiT1 and PiT2 in the cerebellar cortex of adult mice (16-22 days after birth).

All the three transporters were shown to be localized in the GL and the Purkinje Layer (PL). It is worth noting that the expression of the transporters in the Purkinje cells is irregular in intensity.

---

The invention claimed is:

1. A method for determining a physiological state of target cells taking place at a given time or during a given time interval, comprising:

contacting the target cells with at least two soluble receptor binding ligands comprising the totality of the receptor binding domains (RBD) of at least two glycoproteins of at least two enveloped viruses that interacts with a cellular cognate receptor, each of said at least two receptor binding ligands having a tag, detectable molecule or label coupled thereto, each of said at least two soluble receptor binding ligands containing the totality of one of the RBD of said glycoprotein, wherein said RBD does not comprise a transmembrane domain; and, wherein complexes are formed between each of said at least two soluble receptor binding ligands and each of at least two distinct membrane receptors, and the complexes are detectable by the tag, the detectable molecule or the label coupled to each of said at least two receptor binding ligands, wherein all receptor binding ligands contacting the cells contain the totality of RBD of said glycoprotein, and said all receptor binding ligands do not comprise a transmembrane domain, and wherein said at least two glycoproteins belong to viruses selected from the group consisting of: Amphotropic MLV (ampho, SEQ ID NO:1), Gibbon Ape Leukemia virus (GALV, SEQ ID NO:2), Feline endogenous virus (RD114, SEQ ID NO:3), vesicular stomatitis virus (VSV, SEQ ID NO:4), Xenotropic Murine Leukaemia Virus (NZB, Xeno, SEQ ID NO: 10), Feline Leukaemia Virus C (FeLV, SEQ ID NO: 19), Env Koala Retrovirus (KoV, SEQ ID NO: 20), Env Porcine Endogeneous Retrovirus-B (Perv B, SEQ ID NO: 22), Human T Leukaemia Virus-1 (HTLV1, SEQ ID NO:27), Human T Leukaemia Virus-2 (HTLV2, SEQ ID NO:28), Human T Leukaemia Virus-4 (HTLV4, SEQ ID NO: 31), and Env Bovine Leukaemia Virus (BLV, SEQ ID NO: 30).

2. The method according to claim 1, wherein said membrane receptors are selected from the group consisting of CAT1, PiT2, XPR1, SMIT1, PiT1, ASCT1/ASCT2, FLVCR, PAR1, PAR2, and GLUT1.

3. The method according to claim 1, wherein said target cells are animal stem cells.

4. The method according to claim 3, wherein said animal stem cells are human stem cells or cancer stem cells.

5. The method according to claim 3, wherein said target cells are haematopoietic stem cells or B or T cells.

6. The method according to claim 1, wherein said at least two soluble receptor binding ligands is a set of three to twelve soluble receptor binding ligands isolated from glycoproteins belonging to viruses selected from the group consisting of: Amphotropic MLV (ampho, SEQ ID NO:1), Gibbon Ape Leukemia virus (GALV, SEQ ID NO:2), Feline endogenous virus (RD114, SEQ ID NO:3), vesicular stomatitis virus (VSV, SEQ ID NO:4), Xenotropic Murine Leukaemia Virus (NZB, Xeno, SEQ ID NO: 10), Feline Leukaemia Virus C (FeLV, SEQ ID NO: 19), Env Koala Retrovirus (KoV, SEQ ID NO: 20), Env Porcine Endogeneous Retrovirus-B (Perv B, SEQ ID NO: 22), Human T Leukaemia Virus-1 (HTLV1, SEQ ID NO:27), Human T Leukaemia Virus-2 (HTLV2, SEQ ID NO:28), Human T Leukaemia Virus-4 (HTLV4, SEQ ID NO: 31), and Env Bovine Leukaemia Virus (BLV, SEQ ID NO: 30).

7. The method according to claim 1, wherein said soluble receptor binding ligand is a set of ten receptor binding ligands wherein the RBD of glycoproteins are selected from glycoproteins belonging to viruses selected from the group consisting of: Amphotropic MLV (ampho), Feline endogenous virus (RD114), Gibbon Ape Leukemia virus (GALV), Xenotropic Murine Leukaemia Virus (NZB, Xeno), Env Koala Retrovirus (KoV), Env Porcine Endogeneous Retrovirus-B (Perv B), Human T Leukaemia Virus-2 (HTLV2), Human T Leukaemia Virus-4 (HTLV4), Env Bovine Leukaemia Virus (BLV), and Env Feline Leukaemia Virus C (FeLV).

8. The method according to claim 1, wherein said soluble receptor binding ligand is a set of eight receptor binding ligands wherein the RBD of glycoproteins are selected from glycoproteins belonging to viruses selected from the group consisting of: Amphotropic MLV (ampho, SEQ ID NO:1), Gibbon Ape Leukemia virus (GALV, SEQ ID NO:2), Feline endogenous virus (RD114, SEQ ID NO:3), vesicular stomatitis virus (VSV, SEQ ID NO:4), Xenotropic Murine Leukaemia Virus (NZB, Xeno, SEQ ID NO: 10), Feline Leukaemia Virus C (FeLV, SEQ ID NO: 19), Env Koala Retrovirus (KoV, SEQ ID NO: 20), Env Porcine Endogeneous Retrovirus-B (Perv B, SEQ ID NO: 22), Human T Leukaemia Virus-1 (HTLV1, SEQ ID NO:27), Human T Leukaemia Virus-2 (HTLV2, SEQ ID NO:28), Human T Leukaemia Virus-4 (HTLV4, SEQ ID NO: 31), and Env Bovine Leukaemia Virus (BLV, SEQ ID NO: 30).

9. The method according to claim 1, wherein said RBD of glycoproteins belong to viruses selected from the group consisting of: Amphotropic MLV (ampho), Feline endogenous virus (RD114), Xenotropic Murine Leukaemia Virus (NZB, Xeno), Env Koala Retrovirus (KoV), Env Porcine Endogeneous Retrovirus-B (Perv B), Human T Leukaemia Virus-2 (HTLV2), Human T Leukaemia Virus-4 (HTLV4), and Env Bovine Leukaemia Virus (BLV).

10. The method according to claim 1, wherein said at least two soluble receptor binding ligands is a set of four soluble receptor binding ligands isolated from glycoproteins belonging to viruses selected from the group consisting of: Amphotropic MLV (ampho, SEQ ID NO:1), Gibbon Ape Leukemia virus (GALV, SEQ ID NO:2), Feline endogenous virus (RD114, SEQ ID NO:3), vesicular stomatitis virus (VSV, SEQ ID NO:4), Xenotropic Murine Leukaemia Virus (NZB, Xeno, SEQ ID NO: 10), Feline Leukaemia Virus C (FeLV, SEQ ID NO: 19), Env Koala Retrovirus (KoV, SEQ ID NO: 20), Env Porcine Endogeneous Retrovirus-B (Perv B, SEQ ID NO: 22), Human T Leukaemia Virus-1 (HTLV1, SEQ ID NO:27), Human T Leukaemia Virus-2 (HTLV2, SEQ ID NO:28), Human T Leukaemia Virus-4 (HTLV4, SEQ ID NO: 31), and Env Bovine Leukaemia Virus (BLV, SEQ ID NO: 30).

11. The method according to claim 1, for the implementation of a selection process of target cells, having a defined physiological state.

12. The method according to claim 11, wherein said target cells are stem cells sub-population expressing said at least two membrane receptors.

13. A process of identification and quantification of the expression of membrane receptors to a glycoprotein RBD of target cells comprising the following steps:
   a. contacting at least two soluble receptor binding ligands, as defined in claim 1, optionally marked with a tag, with a target cell to form at least two complexes, each complex being constituted by one said receptor binding ligand and one said membrane receptor of said target cell,
   b. identifying each complex formed,
   c. quantifying the expression of each membrane receptor of said target cell able to form said complex,
   d. optionally, distinguishing receptors expressed to the surface of the membrane of the target cell from the total receptors expressed within the target cell.

14. The process according to claim 13, wherein said target cells are animal stem cells.

15. The process according to claim 14, wherein said animal stem cells are human stem cells.

16. The process according to claim 14, wherein said target cells are haematopoietic stem cells or B cells or T cells.

17. A process of selection of target cells expressing at least one particular membrane receptor to a glycoprotein RBD in a given amount of expression, comprising the following steps:
   a. contacting at least two soluble receptor binding ligands, as defined in claim 1, optionally marked with a tag, with a target cell to form at least two complexes, each complex being constituted by one said receptor binding ligand and one said membrane receptor of said target cell,
   b. detecting each complex formed and quantifying said each complex formed at an instant T1,
   c. detecting and quantifying said each complex formed at a second instant T2, T2 being higher than T1,
   d. selecting at T2 said target cells presenting a variation in the expression of at least one particular membrane receptor having formed said complex.

18. The process of selection according to claim 17, wherein said target cells are animal stem cells.

19. The process according to claim 18, wherein said animal stem cells are human stem cells.

20. The process of selection according to claim 18, wherein said target cells are haematopoietic stem cells or B cells or T cells.

21. A process of amplification of target cells expressing at least one particular membrane receptor to a glycoprotein RBD in a given amount of expression, comprising the following steps:
   a. contacting at least two soluble receptor binding ligands, as defined in claim 1, optionally marked with a tag, with a target cell to form at least two complexes, each complex being constituted by one said receptor binding ligand and one said membrane receptor of said target cell,
   b. detecting each complex formed and quantifying said each complex formed at an instant T1,
   c. detecting and quantifying said each complex formed at a second instant T2, T2 being higher than T1,
   d. selecting at T2 said target cells presenting a variation in the expression of at least one particular membrane receptor having formed said complex,
   e. sorting out and amplifying said selected target cells.

22. The process of amplification according to claim 21, wherein said target cells are animal stem cells.

23. The process according to claim 22, wherein said animal stem cells are human stem cells.

24. The process of amplification according to claim 21, wherein said target cells are haematopoietic stem cells or B cells or T cells.

* * * * *